(12) United States Patent
Dubey et al.

(10) Patent No.: US 10,960,100 B2
(45) Date of Patent: *Mar. 30, 2021

(54) HEMOSTATIC DEVICES

(71) Applicant: Z-Medica, LLC, Wallingford, CT (US)

(72) Inventors: Dina Dubey, Fairfield, NJ (US); Denny Lo, Bethlehem, CT (US)

(73) Assignee: Z-Medica, LLC, Wallingford, CT (US)

( * ) Notice: Subject to any disclaimer, the term of this patent is extended or adjusted under 35 U.S.C. 154(b) by 72 days.

This patent is subject to a terminal disclaimer.

(21) Appl. No.: 15/429,935

(22) Filed: Feb. 10, 2017

(65) Prior Publication Data

US 2017/0151365 A1  Jun. 1, 2017

Related U.S. Application Data

(63) Continuation of application No. 15/071,520, filed on Mar. 16, 2016, now Pat. No. 9,603,964, which is a continuation of application No. 14/720,142, filed on May 22, 2015, now Pat. No. 9,352,066, which is a continuation of application No. 13/922,115, filed on Jun. 19, 2013, now Pat. No. 9,072,806.

(60) Provisional application No. 61/754,129, filed on Jan. 18, 2013, provisional application No. 61/663,412, filed on Jun. 22, 2012.

(51) Int. Cl.

| | | |
|---|---|---|
| *A61L 15/16* | (2006.01) | |
| *A61L 15/28* | (2006.01) | |
| *A61L 15/44* | (2006.01) | |
| *A61L 15/46* | (2006.01) | |
| *A61L 15/18* | (2006.01) | |

(52) U.S. Cl.
CPC ............ *A61L 15/28* (2013.01); *A61L 15/18* (2013.01); *A61L 15/44* (2013.01); *A61L 15/46* (2013.01); *A61L 2300/102* (2013.01); *A61L 2300/104* (2013.01); *A61L 2300/402* (2013.01); *A61L 2300/404* (2013.01); *A61L 2300/406* (2013.01); *A61L 2300/41* (2013.01); *A61L 2300/418* (2013.01); *A61L 2300/432* (2013.01); *A61L 2400/04* (2013.01); *A61L 2420/02* (2013.01); *A61L 2420/04* (2013.01); *A61L 2420/08* (2013.01)

(58) Field of Classification Search
CPC .......... A61L 15/28; A61L 15/44; A61L 15/46; A61L 15/18; A61L 2300/104; A61L 2300/402; A61L 2300/404; A61L 2300/406; A61L 2300/41; A61L 2300/432; A61L 2420/08; A61L 2300/102; A61L 2300/418; A61L 2420/02; A61L 2420/04; A61L 2400/04; A61L 2/0005; C08L 5/04

See application file for complete search history.

(56) References Cited

U.S. PATENT DOCUMENTS

| | | |
|---|---|---|
| 2,688,586 A | 9/1954 | Eberl et al. |
| 2,922,719 A | 1/1960 | Robinson |
| 2,969,145 A | 1/1961 | Hannuer, Jr. |
| 3,122,140 A | 2/1964 | Crowe et al. |
| 3,181,231 A | 5/1965 | Breck |
| 3,189,227 A | 6/1965 | Hobbs et al. |
| 3,366,578 A | 1/1968 | Michalko |
| 3,386,802 A | 6/1968 | Michalko |
| 3,538,508 A | 11/1970 | Young |
| 3,550,593 A | 12/1970 | Kaufman |
| 3,608,070 A | 9/1971 | Nouvel |
| 3,658,984 A | 4/1972 | Kamp |
| 3,698,392 A | 10/1972 | Vogt et al. |
| 3,723,352 A | 3/1973 | Warner et al. |
| 3,763,900 A | 10/1973 | Solms-Baruth et al. |
| 3,979,335 A | 9/1976 | Golovko et al. |
| 4,373,519 A | 2/1983 | Errede et al. |
| 4,374,044 A | 2/1983 | Schaefer et al. |
| 4,379,143 A | 4/1983 | Sherry et al. |
| 4,435,512 A | 3/1984 | Ito et al. |
| 4,460,642 A | 7/1984 | Errede et al. |
| 4,514,510 A | 4/1985 | Alexander |

(Continued)

FOREIGN PATENT DOCUMENTS

| | | |
|---|---|---|
| CA | 1 223 208 | 6/1987 |
| CN | 101104080 | 1/2008 |

(Continued)

OTHER PUBLICATIONS

"Mastering the Art of Innovative Thinking," (color brochure) FMC BioPolymer, 2001 FMC Corporation.

(Continued)

*Primary Examiner* — Hasan S Ahmed
(74) *Attorney, Agent, or Firm* — Knobbe, Martens, Olson & Bear, LLP

(57) ABSTRACT

Hemostatic devices for promoting blood clotting can include a substrate (e.g., gauze, textile, sponge, sponge matrix, one or more fibers, etc.), a hemostatic material disposed thereon such as kaolin clay, and a binder material such as crosslinked calcium alginate with a high guluronate monomer molar percentage disposed on the substrate to substantially retain the hemostatic material. When the device is used to treat a bleeding wound, at least a portion of the clay material comes into contact with blood to accelerate clotting. Moreover, when exposed to blood, the binder has low solubility and retains a majority of the clay material on the gauze. A bandage that can be applied to a bleeding wound to promote blood clotting includes a flexible substrate and a gauze substrate mounted thereon.

19 Claims, 13 Drawing Sheets

(56) References Cited

U.S. PATENT DOCUMENTS

| | | |
|---|---|---|
| 4,524,064 A | 6/1985 | Nambu |
| 4,525,410 A | 6/1985 | Hagiwara et al. |
| 4,569,343 A | 2/1986 | Kimura et al. |
| 4,626,550 A | 12/1986 | Hertzenberg |
| 4,631,845 A | 12/1986 | Samuel et al. |
| 4,651,725 A | 3/1987 | Kifune et al. |
| 4,717,735 A | 1/1988 | Stem |
| 4,728,323 A | 3/1988 | Matson |
| 4,748,978 A | 6/1988 | Kamp |
| 4,822,349 A | 4/1989 | Hursey et al. |
| 4,828,081 A | 5/1989 | Nordstrom et al. |
| 4,828,832 A | 5/1989 | DeCuellar et al. |
| 4,911,898 A | 3/1990 | Hagiwara et al. |
| 4,938,958 A | 7/1990 | Niira et al. |
| 4,956,350 A | 9/1990 | Mosbey |
| 5,140,949 A | 8/1992 | Chu et al. |
| 5,144,016 A | 9/1992 | Skjak-Braek et al. |
| 5,146,932 A | 9/1992 | McCabe |
| 5,474,545 A | 12/1995 | Chikazawa |
| 5,482,932 A | 1/1996 | Thompson |
| 5,486,195 A | 1/1996 | Myers et al. |
| 5,502,042 A | 3/1996 | Gruskin et al. |
| 5,538,500 A | 7/1996 | Peterson |
| 5,556,699 A | 9/1996 | Niira et al. |
| 5,575,995 A | 11/1996 | Giovanoni |
| 5,578,022 A | 11/1996 | Scherson et al. |
| 5,597,581 A | 1/1997 | Kaessmann et al. |
| 5,599,578 A | 2/1997 | Butland |
| D386,002 S | 11/1997 | Hinkle |
| 5,696,101 A | 12/1997 | Wu et al. |
| 5,716,337 A | 2/1998 | McCabe et al. |
| 5,725,551 A | 3/1998 | Myers et al. |
| 5,728,451 A | 3/1998 | Langley et al. |
| 5,766,715 A | 6/1998 | Garconnet |
| 5,788,682 A | 8/1998 | Maget |
| 5,801,116 A | 9/1998 | Cottrell et al. |
| 5,826,543 A | 10/1998 | Raymond et al. |
| 5,855,570 A | 1/1999 | Scherson et al. |
| 5,891,074 A | 4/1999 | Cerarczyk |
| 5,916,511 A | 6/1999 | Kotani et al. |
| 5,941,897 A | 8/1999 | Myers |
| 5,964,239 A | 10/1999 | Loux et al. |
| 5,964,349 A | 10/1999 | Odagiri |
| 5,981,052 A | 11/1999 | Siguyama |
| 5,993,964 A | 11/1999 | Nakajima |
| 6,037,280 A | 3/2000 | Edwards et al. |
| 6,060,461 A | 5/2000 | Drake |
| 6,086,970 A | 7/2000 | Ren |
| 6,123,925 A | 9/2000 | Barry et al. |
| 6,159,232 A | 12/2000 | Nowakowski |
| 6,187,347 B1 | 2/2001 | Patterson et al. |
| 6,203,512 B1 | 3/2001 | Farris et al. |
| 6,251,423 B1 | 6/2001 | Brandford |
| 6,372,333 B1 | 4/2002 | Sugiyama et al. |
| 6,428,800 B2 | 8/2002 | Greenspan et al. |
| 6,450,537 B2 | 9/2002 | Norris |
| 6,475,470 B1 | 11/2002 | Kayane et al. |
| 6,481,134 B1 | 11/2002 | Aledo |
| 6,486,285 B2 | 11/2002 | Fujita |
| 6,495,367 B1 | 12/2002 | Isogawa et al. |
| 6,523,778 B2 | 2/2003 | Key et al. |
| 6,573,419 B2 | 6/2003 | Naimer |
| 6,590,337 B1 | 7/2003 | Nishikawa et al. |
| 6,622,856 B2 | 9/2003 | Gallo et al. |
| 6,630,140 B1 | 10/2003 | Grunstein |
| 6,638,073 B1 | 10/2003 | Kazimirov et al. |
| 6,685,227 B2 | 2/2004 | Merry et al. |
| 6,700,032 B1 | 3/2004 | Gray |
| 6,701,649 B1 | 3/2004 | Brosi |
| 6,745,720 B2 | 6/2004 | Rasner et al. |
| 6,805,961 B1 | 10/2004 | Watanabe et al. |
| 6,890,177 B2 | 5/2005 | Dragan |
| 6,998,510 B2 | 2/2006 | Buckman et al. |
| 7,125,821 B2 | 10/2006 | Xu et al. |
| 7,303,759 B2 | 12/2007 | Mershon |
| 7,322,976 B2 | 1/2008 | Yassinzadeh |
| 7,371,403 B2 | 5/2008 | McCarthy et al. |
| 7,429,252 B2 | 9/2008 | Sarangapani |
| 7,572,274 B2 | 8/2009 | Yassinzadeh |
| 7,595,429 B2 | 9/2009 | Hursey |
| 7,604,819 B2 | 10/2009 | Huey et al. |
| 7,691,127 B2 | 4/2010 | Yassinzadeh |
| 7,815,640 B2 | 10/2010 | Yassinzadeh |
| 7,825,133 B2 | 11/2010 | Yi |
| 7,858,123 B2 | 12/2010 | Stucky |
| 7,968,114 B2 | 6/2011 | Huey et al. |
| 7,993,366 B2 | 8/2011 | Yassinzadeh et al. |
| 8,063,264 B2 | 11/2011 | Spearman et al. |
| 8,114,433 B2 | 2/2012 | Huey et al. |
| 8,118,777 B2 | 2/2012 | Ducharme et al. |
| 8,202,532 B2 | 6/2012 | Huey et al. |
| 8,252,318 B2 | 8/2012 | Huey et al. |
| 8,252,344 B2 | 8/2012 | Hursey |
| 8,257,731 B2 | 9/2012 | Horn et al. |
| 8,257,732 B2 | 9/2012 | Huey et al. |
| 8,277,837 B2 | 10/2012 | Fischer et al. |
| 8,323,305 B2 | 12/2012 | Epstein et al. |
| 8,343,537 B2 | 1/2013 | Huey et al. |
| 8,361,054 B2 | 1/2013 | Ducharme et al. |
| 8,383,148 B2 | 2/2013 | Huey et al. |
| 8,439,944 B2 | 5/2013 | Yassinzadeh |
| 8,444,671 B2 | 5/2013 | Yassinzadeh |
| 8,460,699 B2 | 6/2013 | Huey et al. |
| 8,497,408 B2 | 7/2013 | Whek et al. |
| 8,512,743 B2 | 8/2013 | Horn et al. |
| 8,535,709 B2 | 9/2013 | Kennedy et al. |
| 8,557,278 B2 | 10/2013 | Huey et al. |
| 8,595,429 B2 | 11/2013 | Gu et al. |
| 8,703,634 B2 | 4/2014 | Baker et al. |
| 8,747,435 B2 | 6/2014 | Yassinzadeh |
| 8,784,876 B2 | 7/2014 | Huey et al. |
| 8,846,076 B2 | 9/2014 | Huey et al. |
| 8,858,969 B2 | 10/2014 | Pahari et al. |
| 8,911,472 B2 | 12/2014 | Yassinzadeh et al. |
| 8,938,898 B2 | 1/2015 | Lo et al. |
| 9,017,374 B2 | 4/2015 | Yassinzadeh |
| 9,072,806 B2 * | 7/2015 | Lo .............. A61L 15/18 |
| 9,078,782 B2 | 7/2015 | Huey et al. |
| 9,179,897 B2 | 11/2015 | Yassinzadeh et al. |
| 9,352,066 B2 * | 5/2016 | Dubey ............ A61L 15/18 |
| 9,370,347 B2 | 6/2016 | Yassinzadeh |
| 9,427,221 B2 | 8/2016 | Yassinzadeh |
| 9,439,637 B2 | 9/2016 | Yassinzadeh et al. |
| 9,597,066 B2 | 3/2017 | Yassinzadeh et al. |
| 9,603,964 B2 * | 3/2017 | Dubey ............ A61L 15/18 |
| 9,839,772 B2 | 12/2017 | Ducharme |
| 9,867,931 B2 | 1/2018 | Gittard |
| 10,086,106 B2 | 10/2018 | Huey et al. |
| 10,130,347 B2 | 11/2018 | Yassinzadeh |
| 2002/0077653 A1 | 6/2002 | Hudson et al. |
| 2002/0141964 A1 | 10/2002 | Patterson et al. |
| 2002/0197302 A1 | 12/2002 | Cochrum et al. |
| 2003/0018357 A1 | 1/2003 | Luthra et al. |
| 2003/0133990 A1 | 7/2003 | Hursey et al. |
| 2003/0165560 A1 | 9/2003 | Otsuka et al. |
| 2003/0175333 A1 | 9/2003 | Shefer et al. |
| 2003/0176828 A1 | 9/2003 | Buckman et al. |
| 2003/0199922 A1 | 10/2003 | Buckman |
| 2003/0208150 A1 | 11/2003 | Bruder et al. |
| 2003/0212357 A1 | 11/2003 | Pace |
| 2004/0005350 A1 | 1/2004 | Looney et al. |
| 2004/0013715 A1 | 1/2004 | Wnek et al. |
| 2004/0038893 A1 | 2/2004 | Ladner et al. |
| 2004/0121027 A1 | 6/2004 | Pushpangadan et al. |
| 2004/0121438 A1 | 6/2004 | Quirk |
| 2004/0131820 A1 | 7/2004 | Turner et al. |
| 2004/0166172 A1 | 8/2004 | Rosati et al. |
| 2004/0166758 A1 | 8/2004 | Reichmann et al. |
| 2004/0169033 A1 | 9/2004 | Kuibira et al. |
| 2004/0243043 A1 | 12/2004 | McCarthy et al. |
| 2005/0023956 A1 | 2/2005 | Kwak et al. |
| 2005/0058721 A1 | 3/2005 | Hursey |
| 2005/0070693 A1 | 3/2005 | Hansen et al. |
| 2005/0074505 A1 | 4/2005 | Hursey |

(56) References Cited

U.S. PATENT DOCUMENTS

| | | |
|---|---|---|
| 2005/0107826 A1 | 5/2005 | Zhu et al. |
| 2005/0118230 A1 | 6/2005 | Hill et al. |
| 2005/0119112 A1 | 6/2005 | Pfenninger et al. |
| 2005/0137512 A1 | 6/2005 | Campbell et al. |
| 2005/0143689 A1 | 6/2005 | Ramsey, III |
| 2005/0147656 A1 | 7/2005 | McCarthy et al. |
| 2005/0226911 A1 | 10/2005 | Bringley et al. |
| 2005/0246009 A1 | 11/2005 | Toner et al. |
| 2005/0248270 A1 | 11/2005 | Ghosh et al. |
| 2005/0249899 A1 | 11/2005 | Bonutti |
| 2005/0287239 A1 | 12/2005 | Joo et al. |
| 2006/0034935 A1 | 2/2006 | Pronovost et al. |
| 2006/0078628 A1 | 4/2006 | Koman et al. |
| 2006/0116635 A1 | 6/2006 | Van Heughten |
| 2006/0121101 A1 | 6/2006 | Ladizinsky |
| 2006/0127437 A1 | 6/2006 | Kennedy et al. |
| 2006/0141018 A1 | 6/2006 | Cochrum et al. |
| 2006/0141060 A1 | 6/2006 | Hursey et al. |
| 2006/0159733 A1 | 7/2006 | Pendharkar et al. |
| 2006/0172000 A1 | 8/2006 | Cullen et al. |
| 2006/0178609 A1 | 8/2006 | Horn et al. |
| 2006/0193905 A1 | 8/2006 | Ehringer et al. |
| 2006/0211965 A1 | 9/2006 | Horn et al. |
| 2006/0211971 A1 | 9/2006 | Horn et al. |
| 2006/0271094 A1 | 11/2006 | Hudson et al. |
| 2006/0282046 A1 | 12/2006 | Horn et al. |
| 2007/0004995 A1 | 1/2007 | Horn et al. |
| 2007/0016152 A1 | 1/2007 | Karpowicz et al. |
| 2007/0031515 A1 | 2/2007 | Stucky et al. |
| 2007/0065491 A1 | 3/2007 | Huey et al. |
| 2007/0104768 A1 | 5/2007 | Huey et al. |
| 2007/0104792 A1 | 5/2007 | Jenkins |
| 2007/0134293 A1 | 6/2007 | Huey et al. |
| 2007/0142783 A1 | 6/2007 | Huey et al. |
| 2007/0154509 A1 | 7/2007 | Wilcher et al. |
| 2007/0154510 A1 | 7/2007 | Wilcher et al. |
| 2007/0154564 A1 | 7/2007 | Stucky et al. |
| 2007/0160638 A1 | 7/2007 | Mentkow et al. |
| 2007/0160653 A1 | 7/2007 | Fischer et al. |
| 2007/0167971 A1 | 7/2007 | Huey et al. |
| 2007/0251849 A1 | 11/2007 | Lo et al. |
| 2007/0264315 A1 | 11/2007 | Fournie et al. |
| 2007/0275073 A1 | 11/2007 | Huey et al. |
| 2007/0276308 A1 | 11/2007 | Huey et al. |
| 2007/0276345 A1 | 11/2007 | Huey et al. |
| 2007/0281011 A1 | 12/2007 | Jenkins et al. |
| 2008/0027365 A1 | 1/2008 | Huey |
| 2008/0085300 A1 | 4/2008 | Huey et al. |
| 2008/0097271 A1 | 4/2008 | Lo et al. |
| 2008/0125686 A1 | 5/2008 | Lo |
| 2008/0131855 A1 | 6/2008 | Eggert et al. |
| 2008/0145455 A1 | 6/2008 | Bedard |
| 2008/0146984 A1 | 6/2008 | Campbell et al. |
| 2008/0154303 A1 | 6/2008 | Yassinzadeh |
| 2008/0199539 A1 | 8/2008 | Baker et al. |
| 2008/0206134 A1 | 8/2008 | Lo et al. |
| 2008/0254146 A1 | 10/2008 | Huey et al. |
| 2008/0254147 A1 | 10/2008 | Huey et al. |
| 2008/0269658 A1 | 10/2008 | Vinton et al. |
| 2008/0299226 A1 | 12/2008 | Mentkow et al. |
| 2008/0317831 A1 | 12/2008 | Lo |
| 2008/0319476 A1 | 12/2008 | Ward et al. |
| 2009/0008261 A1 | 1/2009 | Kotzeva et al. |
| 2009/0011394 A1 | 1/2009 | Meglan et al. |
| 2009/0018479 A1 | 1/2009 | McCarthy et al. |
| 2009/0043268 A1 | 2/2009 | Eddy et al. |
| 2009/0047366 A1 | 2/2009 | Bedard et al. |
| 2009/0053288 A1 | 2/2009 | Eskridge, Jr. et al. |
| 2009/0074880 A1 | 3/2009 | Ladizinsky |
| 2009/0076475 A1 | 3/2009 | Ross et al. |
| 2009/0112170 A1 | 4/2009 | Wells et al. |
| 2009/0123525 A1 | 5/2009 | Bedard |
| 2009/0155342 A1 | 6/2009 | Diegelmann et al. |
| 2009/0162406 A1 | 6/2009 | Basadonna et al. |
| 2009/0186013 A1 | 7/2009 | Stucky |
| 2009/0186071 A1 | 7/2009 | Huey et al. |
| 2009/0232902 A1 | 9/2009 | Liu et al. |
| 2009/0274769 A1 | 11/2009 | Fregonese |
| 2009/0299253 A1 | 12/2009 | Hursey |
| 2010/0035045 A1 | 2/2010 | McAmish |
| 2010/0047352 A1 | 2/2010 | Pronovost et al. |
| 2010/0079395 A1 | 4/2010 | Kim et al. |
| 2010/0121244 A1 | 5/2010 | Horn et al. |
| 2010/0158989 A1 | 6/2010 | Mentkow et al. |
| 2010/0168767 A1 | 7/2010 | Yassinzadeh |
| 2010/0172958 A1 | 7/2010 | Lucchesi et al. |
| 2010/0184348 A1 | 7/2010 | McAmish |
| 2010/0209531 A2 | 8/2010 | Stucky et al. |
| 2010/0228174 A1 | 9/2010 | Huey et al. |
| 2010/0233248 A1 | 9/2010 | Huey et al. |
| 2010/0292624 A1 | 11/2010 | Diegelmann et al. |
| 2010/0324464 A1 | 12/2010 | Kamakura et al. |
| 2011/0015565 A1 | 1/2011 | Hursey |
| 2011/0059287 A1 | 3/2011 | McAmish |
| 2011/0064785 A1 | 3/2011 | Daniels |
| 2011/0150973 A1 | 6/2011 | Bowlin et al. |
| 2011/0229849 A1 | 9/2011 | Maurer et al. |
| 2011/0237994 A1 | 9/2011 | Russ et al. |
| 2011/0268784 A1 | 11/2011 | Huey |
| 2012/0004636 A1 | 1/2012 | Lo |
| 2012/0045742 A1 | 2/2012 | Meglan et al. |
| 2012/0070470 A1 | 3/2012 | Pahari |
| 2012/0130296 A1 | 5/2012 | Huey |
| 2012/0259262 A1 | 10/2012 | Huey |
| 2013/0041332 A1 | 2/2013 | Huey |
| 2013/0060279 A1 | 3/2013 | Yassinzadeh |
| 2013/0079695 A1 | 3/2013 | Huey |
| 2013/0178778 A1 | 7/2013 | Huey |
| 2013/0267923 A1 | 10/2013 | Huey |
| 2013/0344131 A1 | 12/2013 | Lo |
| 2014/0171848 A1 | 6/2014 | Huey et al. |
| 2014/0377362 A1 | 12/2014 | Pahari |
| 2015/0141301 A1 | 5/2015 | Rovison, Jr. et al. |
| 2015/0209019 A1 | 7/2015 | Yassinzadeh |
| 2015/0221238 A1 | 8/2015 | Huebner |
| 2015/0250918 A1 | 9/2015 | Dubey |
| 2016/0120901 A1 | 5/2016 | Basadonna |
| 2016/0141018 A1 | 5/2016 | Lin et al. |
| 2016/0193380 A1 | 7/2016 | Dubey |
| 2016/0213808 A1 | 7/2016 | Huey |
| 2016/0256142 A1 | 9/2016 | Yassinzadeh |
| 2016/0345946 A1 | 12/2016 | Yassinzadeh et al. |
| 2017/0202546 A1 | 7/2017 | Yassinzadeh et al. |
| 2017/0296579 A1 | 10/2017 | Basadonna |
| 2018/0104378 A1 | 4/2018 | Huey |
| 2018/0221006 A1 | 8/2018 | Yassinzadeh |
| 2018/0228934 A1 | 8/2018 | Huey |
| 2018/0271898 A1 | 9/2018 | Basadonna |
| 2019/0167241 A1 | 6/2019 | Yassinzadeh et al. |

FOREIGN PATENT DOCUMENTS

| | | |
|---|---|---|
| CN | 201920992 U | 8/2011 |
| EP | 0 107 051 | 9/1983 |
| EP | 0 296 324 | 12/1988 |
| EP | 0 353 710 | 2/1990 |
| EP | 0 826 822 | 3/1998 |
| EP | 0 888 783 A1 | 7/1999 |
| EP | 1 159 972 A2 | 5/2001 |
| EP | 1 714 642 | 10/2006 |
| EP | 2 446 867 | 5/2012 |
| EP | 2 863 961 | 8/2018 |
| EP | 3 412 320 | 12/2018 |
| GB | 548046 | 9/1942 |
| GB | 2 175 889 | 12/1986 |
| GB | 2 259 858 | 3/1993 |
| GB | 2 314 842 | 1/1998 |
| JP | S59-62050 | 9/1984 |
| JP | 61145120 | 7/1986 |
| JP | 01-096558 | 10/1987 |
| JP | 2-45040 | 2/1990 |
| JP | 9-504719 | 5/1997 |
| JP | 2777279 B2 | 7/1998 |
| JP | 10-337302 | 12/1998 |

(56) References Cited

FOREIGN PATENT DOCUMENTS

| | | |
|---|---|---|
| JP | 11-071228 | 3/1999 |
| JP | 11-178912 | 7/1999 |
| JP | 11-332909 A1 | 7/1999 |
| JP | 2002-530157 | 9/2002 |
| JP | 2002-331024 | 11/2002 |
| JP | 2003-66045 | 3/2003 |
| JP | 2003-305079 | 10/2003 |
| JP | 2005-015537 | 1/2005 |
| JP | 2004123651 | 7/2006 |
| WO | WO 1992/19802 | 11/1992 |
| WO | WO 95/05445 | 2/1995 |
| WO | WO 95/12371 | 5/1995 |
| WO | WO 96/40285 | 12/1996 |
| WO | WO 99/13918 | 3/1999 |
| WO | WO 00/30694 | 6/2000 |
| WO | WO 00/66086 | 11/2000 |
| WO | WO 01/082896 | 8/2001 |
| WO | WO 01/097826 | 12/2001 |
| WO | WO 02/030479 | 4/2002 |
| WO | WO 02/060367 | 8/2002 |
| WO | WO 02/074325 | 9/2002 |
| WO | WO 03/057072 | 7/2003 |
| WO | WO 03/074566 | 9/2003 |
| WO | WO 05/012493 | 2/2005 |
| WO | WO 05/030279 | 4/2005 |
| WO | WO 05/087280 | 9/2005 |
| WO | WO 05/123170 | 12/2005 |
| WO | WO 06/006140 | 1/2006 |
| WO | WO 06/012218 | 2/2006 |
| WO | WO 06/088912 | 8/2006 |
| WO | WO 06/110393 | 10/2006 |
| WO | WO 07/120342 | 10/2007 |
| WO | WO 08/036225 | 3/2008 |
| WO | WO 08/054566 | 5/2008 |
| WO | WO 08/109160 | 9/2008 |
| WO | WO 08/127497 | 10/2008 |
| WO | WO 09/109194 | 9/2009 |
| WO | WO 14/047436 | 3/2014 |

OTHER PUBLICATIONS

Alam, et al., Application of a Zeolite Hemostatic Agent Achieves 100% Survival in a Lethal Model of Complex Groin Injury in Swine, May 2004, The Journal of Trauma Injury, Infection, and Critical Care, vol. 56, pp. 974-983.

Alam, et al., Comparative Analysis of Hemostatic Agents in a Swine Model of Lethal Groin Injury, Jun. 2003, The Journal of Trauma Injury, Infection, and Critical Care, vol. 54, No. 6, pp. 1077-1082.

Aldrich—Handbook of Fine Chemicals and Laboratory Equipment, 2000-2001, pp. 1177-1178.

Analgesics and Anti-inflammatory agents 2004, retrieved from the internet on May 26, 2010, URL: http://web.archive.org/web/20040904151322/http://faculty.weber.edu/ewalker/Medicinal_Chemistry/topics/Analgesia_antiinflam/Analgesics_anti-inflammatory.htm.

Angeloni, V., M.D.: "How to care for your wound.", Heartland Dermatology & Skin Cancer P. C., copyright 2001, V. Angeloni MD.

Army halts use of new first aid item to study more, Seattle PI, Dec. 24, 2008.

Army halts use of WoundStat, http://stripes.com, Apr. 23, 2009.

Army pulls anti clotting agent after Fort Sam study finds threat, MySanAntonio Military, Dec. 24, 2008.

Baker, Sarah E. et al., Controlling Bioprocesses with Inorganic Surfaces: Layered Clay Hemostatic Agents, Department of Chemistry and Biochemistry, University of California, Santa Barbara, American Chemical Association 2007, 19, pp. 4390-4392 (3 pages total).

Basadonna, G., et al.: "A novel kaolin coated surgical gauze improves hemostasis both in vitro and in vivo", Journal of Surgical Research, vol. 144, No. 2, Feb. 2008, p. 440, XP002534658, abstract.

Bethesda, MD, TraumaCure, Life-saving News for Battlefield Soldiers & Wounded Civilians FDA Clears Product to Stop Severe Bleeding, Sep. 10, 2007.

Butenas—Mechanism of factor VIIa-dependent coagulation in hemophilia blood, Hemostasis, Thrombosis, and Vascular Biology, BLOOD, Feb. 1, 2002—vol. 99, No. 3.

CALOPLAST (Kaolin Poultrice), South African Electronic Package Inserts, Information presented by Malahide Information Systems, Copyright 1996-1998, printed from home.intekom.com/pharm/allied/caloplst.html#INDICATIONS, two pages.

Carraway, et al., Comparison of a new mineral based hemostatic agent to a commercially available granular zeolite agent for hemostasis in a swine model of lethal extremity arterial hemorrhage, Resuscitation vol. 78, Issue 2, Aug. 2008.

Clay makers (raw materials) retrieved from the internet on Mar. 15, 2010, URL: http://web.archive.org/web/20020609175053/http://www.claymaker.com/ceramic_central/info/raw_clays.htm (year 2002, pp. 104).

Comparative Testing of Hemostatic Dressings in a Severe Groin Hemorrhage, Trauma & Resuscitative Medicine Department, NMRC, Aug. 2008 (Part 2 of 3, pp. 10-19).

Comparative Testing of Hemostatic Dressings in a Severe Groin Hemorrhage, Trauma & Resuscitative Medicine Department, NMRC, Aug. 2008 (Part 3 of 3, pp. 20-29).

Comparative Testing of Hemostatic Dressings in a Severe Groin Hemorrhage, Trauma &Resuscitative Medicine Department, NMRC Aug. 2008 (Part 1 of 3, pp. 1-9).

Connor, William E.: "The Acceleration of Thrombus Formatin by Certain Fatty Acids," Journal of Clinical Investigation, vol. 41, No. 6, 1962.

Curasorb Calcium Alginate Dressings information page, http://www.kendallhq.com/kendallhealthcare/pageBuilder.aspx?webPageID=0&topicID=70966&xsl=xsl/productPagePrint.xsl (last accessed May 22, 2012).

Davis et al., 1H—NMR Study of Na Alginates Extracted from *Sargassum* spp. in Relation to Metal Biosorption, 110 Applied Biochemistry and Biotechnology 75 (2003).

Dictionary of Traditional Chinese Medicine, "Astringents and Haemostatices," The Commercial Press, LTD., Apr. 1984 [ISBN 962 07 3051 8], pp. 216-217, total 4 pages.

Dyer, A. et al. "Diffusion in heteroionic zeolites: part 1. Diffusion of water in heteroionics natrolites." Microporous and Mesoporous Materials. 1998. pp. 27-38. vol. 21.

European, Extended Search Report, re Application No. 10190569.3, dated Jan. 25, 2011.

Fruijtier-Polloth, "The safety of synthetic zeolites used in detergents", Arch Toxicol (2009) 83:23-25.

Galan, et al.: "Technical properties of compound kaolin sample from griva (Macedonia, Greece)", Applied Clay Science 1996 10:477-490.

Gibbar-Clements, et al.: "The Challenge of Warfarin Therapy", JSTOR: The American Journal of Nursing,vol. 100, No. 3 (Mar. 2000), pp. 38-40.

Gielen, M., Solid State Organometallic Chemistry: Methods and Applications Physical Organometallic Chemistry, 1999, New York John Wiley & Sons, Ltd. (UK), V. 2, p. 156.

Griffin, John H., Role of surface in surface-dependent activation of Hageman factor (blood coagulation Factor XII), Proc. Natl. Acad. Sci. USA, vol. 75, No. 4, Apr. 1978, pp. 1998-2002 (5 pages total).

Hahn, Lynn: "High temperature 1H NMR to determine the relative amounts of guluronate and mannuronate in the sodium alginate sample", Intertek, ASA, Analytical Report, Report No. 60665 v 1, dated May 6, 2012.

Handbook of textile fibre structure, First Published 2009, p. 276, Par. 1. (1 page).

HemCon Medical Technologies Inc. 501(k) Summary, ChitoGauze, Mar. 20, 2009.

Hempen, et al., A Materia Medica for Chinese Medicine, Plants minerals and animal products, Churchill Livingston Elsevier, 2009, [ISBN 978 0 443 10094 9], pp. 832-833 (Halloysitum rubrum, Chi shi zi), total 5 pages.

Hollister Wound Care Restore Calcium Alginate Dressing, Silver instruction manual and information booklet, available at http://

(56) References Cited

OTHER PUBLICATIONS hollisterwoundcare.com/files/pdfs/ifus/Restore907814B407ColorBreak. pdf (last accessed May 22, 2012).
Hsu, et al. Orintal Materia Medica—a concise guide, pp. 310-311, 612-613, 32-34, total 12 pages. Oriental Healing Arts Institute, 1986. [ISBN 0 941 942 22 8].
Huang, Pharmacology of Chinese Herbs, Second Edition, p. 243 (Antidiarrheal Herbs), total 3 pages. CRC Press 1999. [ISBN 0 8493 1665 0].
Hubbard, et al.: "Ionic charges of glass surfaces and other materials, and their possible role in the coagulation of blood," Journal of Applied Physiology, Mar. 1, 1960, vol. 15, No. 2, pp. 265-270.
IMA-EU, Kaolin, Oct. 2006, p. 1-2.
International Preliminary Report and Written Opinion for Application No. PCT/US2007/023265, dated Sep. 29, 2009.
International Preliminary Report and Written Opinion for PCT/US2004/029809, dated Mar. 13, 2006.
International Preliminary Report and Written Opinion re PCT/US2006/004594, dated Aug. 14, 2007.
International Preliminary Report and Written Opinion re PCT/US2008/006517, dated Nov. 24, 2009.
International Preliminary Report and Written Opinion Report for Application No. PCT/US2008/060177, dated Oct. 13, 2009.
International Preliminary Report on Patentability and Written Opinion, re PCT Application No. PCT/US2013/060915, dated Mar. 24, 2015.
International Report on Patentability and Written Opinion for Application No. PCT/US2008/003082, dated Sep. 29, 2009.
International Search Report and Written Opinion re PCT Application No. PCT/US2013/041659, dated Aug. 15, 2013.
International Search Report for Application No. PCT/US2004/029812, dated Jun. 14, 2005.
International Search Report for Application No. PCT/US2006/004594, dated Nov. 3, 2006.
International Search Report for Application No. PCT/US2006/012487, dated Sep. 12, 2006.
International Search Report for Application No. PCT/US2007/016509, dated Feb. 8, 2008.
International Search Report for Application No. PCT/US2007/023265, dated Sep. 17, 2009.
International Search Report for Application No. PCT/US2008/003082, dated Sep. 24, 2009.
International Search Report for Application No. PCT/US2008/060177, dated Jun. 22, 2009.
International Search Report for Application No. PCT/US2008/075191, dated Oct. 6, 2008.
International Search Report for PCT/US2004/029809, dated Feb. 24, 2005.
International Search Report for PCT/US2005/046700, dated Jul. 6, 2006.
James, "Silver Copper Zeolite Guinea Pig Sensitization Study—Buehler Method", Data Evaluation Report dated Oct. 3, 1989.
Kheirabadi, Army Assessment of New Hemostatic Products Suitable for Treating Combat Wounds, US Army Institute of Surgical Research, Aug. 11, 2008.
Kheirabadi, et al., Session IV-B, Paper 28, 8:20 a.m., Comparison of New Hemostatic Dressings with Currently Deployed Hemcon Bandage in a Model of Extremity Arterial Hemorrhage in Swine, Jan. 2009.
Kheirabadi, et al., The Journal of TRAUMA Injury, Infection, and Critical Care, Comparison of New Hemostatic Granules/Powders with Currently Deployed Hemostatic Products in a Lethal model of Extremity Arterial Hemorrhage in Swine, Feb. 2009, pp. 316-328.
Kheirabadi, Final Report, Title: Assessment of Efficacy of New Hemostatic Agents in a Model of Extremity Arterial Hemorrhage in Swine, U.S. Army Institute of Surgical Research, Ft. Sam Houston, TX 78234, Mar. 4, 2008.
Kovzun, I. G., et al.: "Application of nanosize clay-mineral systems in the complex therapy for hemophilia "A" patients", Database HCAPLUS [online], XP002534657, retrieved from STN Database accession No. 2009:502758 abstract & Nanosistemi, Nanomateriali, Nanotekhnologii, vol. 6, No. 2, 2008.
Le Van Mao, Raymond et al. "Mesoporous Aluminosilicates prepared from Zeolites by Treatment with Ammonium Fluorosilicate." J. Mater. Chem. 1993. pp. 679-683. vol. 3, No. 6.
Li, et al. Chinese Materia Medica—Combinations and Applications, Donica Publishing Ltd., 2002, [ISBN 1 901149 02 1], p. 622 (Ch. 18 Herbs for Promoting Astriction), total 5 pages.
Lin et al., Synthesis of Hybridized Polyacrylic Acid-Kaolin Material and Its Superwater Absorbent Performance, J. Huaqiao Univ. (Nat. Sci.) Mar. 2000.
Long et al., Synthesis of Bentonite-superabsorbent Composite, J. Guilin Inst. Tech., Feb. 2004.
Macrina, VCU's Research Enterprise, Structure and Resources, Oct. 23, 2008.
Manugel® GMB alginate, FMC BioPolymer, Know how. It works. sm Product Specifications, 2011 FMC Corporation.
Margolis, "Initiation of Blood Coagulation By Glass and Related Surfaces", J. Physiol. (1957) 137, 95-109.
Margolis, J., The Kaolin Clotting Time: A Rapid One-Stage Method for Diagnosis of Coagulation Defects, J. Clin. Pathol 1958, 11, pp. 406-409 (5 pages total).
Medline Maxorb Extra AG Silver Alginate, http://www.medicaldepartmentstore.com/Medline-Maxorb-p/1560.htm (last accessed May 22, 2012).
Miyajima, C., General Information on Alginates and its Applications, Sen'i Gakkaishi (Fibers and Industry), 2009, pp. 444-448, vol. 65, No. 12.
Okada, et al.: "Preparation of zeolite-coated cordierite honeycombs prepared by an in situ crystallization method", Science and Technology of Advanced Materials 2004 5:479-484.
O'Reilly et al.: "Studies on Coumarin Anticoagulant Drugs—Initiation of Warfarin Therapy Without a Loading Dose", Circulation by the American Heart Association, http://circ.ahajournals.org, 1968, 38, 169-177.
Ore-Medix, Traumastat Hemostatic Bandage, Aug. 7, 2008.
Permanent suspension of Woundstat use, https://email.z-medica.com, Apr. 17, 2009.
Reprinted related contents of U.S. Abstract regarding QuikClot Combat Gauze, Apr. 2009.
Reprinted related contents of US Abstract regarding QuikClot CombatGauze, Sep. 2008.
Ross, et al., "The Kaolin Minerals," J. Amer. Ceramic Soc., vol. 13, issue 3, pp. 151 to 160, Mar. 1930.
Sadler et al.: "Biochemistry and Genetics of Van Willebrand Factor", Annual Review of Biochemistry; 1998. 67:395-424.
Scott Sackinger's Medical Devices Professional Summary dated Mar. 2009.
Sinter. (2004). In The New Penguin Dictionary of Science. London: Penguin. Retrieved May 7, 2009, from http://www.credoreference.com/entry/7463549/.
Soine et al., Roger's Inorganic Pharmaceutical Chemistry, Lea & Febiger 1967, p. 462-463 (Aluminum and Aluminum Compounds), [QV744 S683r 1967] total 5 pages.
Tactical Combat Casualty Care Guidelines, Feb. 2009.
The Merck Index; 1989, pp. 1596-1597, abstract 10021.
Top, Ayben et al. "Silver, zinc, and copper exchange in a Na-clinoptilolite and resulting effect on antibacterial activity." Applied Clay Science. 2004. pp. 13-19. vol. 27.
TraumaCure, Innovative Wound Care Products for Wound Care Solutions, Apr. 24, 2009.
U.S. Appl. No. 12/352,513, filed Jan. 12, 2009 including prosecution history.
U.S. Appl. No. 15/071,520, filed Mar. 16, 2016, including prosecution history.
U.S. Appl. No. 10/939,687, filed Sep. 13, 2004 including prosecution history.
U.S. Appl. No. 10/939,869, filed Sep. 13, 2004 including prosecution history.
U.S. Appl. No. 11/023,869, filed Dec. 27, 2004 including prosecution history.
U.S. Appl. No. 11/054,918, filed Feb. 9, 2005 including prosecution history.

(56) References Cited

OTHER PUBLICATIONS

U.S. Appl. No. 11/082,716, filed Mar. 16, 2005 including prosecution history.
U.S. Appl. No. 11/303,607, filed Dec. 16, 2005 including prosecution history.
U.S. Appl. No. 11/404,126, filed Apr. 13, 2006 including prosecution history.
U.S. Appl. No. 11/544,238, filed Oct. 6, 2006 including prosecution history.
U.S. Appl. No. 11/584,079, filed Oct. 20, 2006 including prosecution history.
U.S. Appl. No. 11/586,968, filed Oct. 25, 2006 including prosecution history.
U.S. Appl. No. 11/590,427, filed Oct. 30, 2006 including prosecution history.
U.S. Appl. No. 11/592,477, filed Nov. 2, 2006 including prosecution history.
U.S. Appl. No. 11/606,617, filed Nov. 29, 2006 including prosecution history.
U.S. Appl. No. 11/633,687, filed Dec. 4, 2006 including prosecution history.
U.S. Appl. No. 11/634,531, filed Dec. 6, 2006 including prosecution history.
U.S. Appl. No. 11/634,673, filed Dec. 5, 2006 including prosecution history.
U.S. Appl. No. 11/654,409, filed Jan. 17, 2007, including prosecution history.
U.S. Appl. No. 11/710,106, filed Feb. 22, 2007 including prosecution history.
U.S. Appl. No. 11/715,057, filed Mar. 6, 2007 including prosecution history.
U.S. Appl. No. 12/101,336, filed Apr. 11, 2008 including prosecution history.
U.S. Appl. No. 12/101,346, filed Apr. 11, 2008 including prosecution history.
U.S. Appl. No. 12/140,356, filed Jun. 17, 2008 including prosecution history.
U.S. Appl. No. 12/204,129, filed Sep. 4, 2008 including prosecution history.
U.S. Appl. No. 12/417,802, filed Apr. 3, 2009 including prosecution history.
U.S. Appl. No. 12/503,481, filed Jul. 15, 2009 including prosecution history.
U.S. Appl. No. 12/510,203, filed Jul. 27, 2009 including prosecution history.
U.S. Appl. No. 12/555,876, filed Sep. 9, 2009, including prosecution history.
U.S. Appl. No. 12/581,782, filed Oct. 19, 2009 including prosecution history.
U.S. Appl. No. 12/611,830, filed Nov. 3, 2009, including prosecution history.
U.S. Appl. No. 13/115,699, filed May 25, 2011 including prosecution history.
U.S. Appl. No. 13/175,380, filed Jul. 1, 2011, including prosecution history.
U.S. Appl. No. 13/240,795, filed Sep. 22, 2011, including prosecution history.
U.S. Appl. No. 13/526,431, filed Jun. 18, 2012 including prosecution history.
U.S. Appl. No. 13/593,310, filed Aug. 23, 2012, including prosecution history.
U.S. Appl. No. 13/595,932, filed Aug. 27, 2012, including prosecution history.
U.S. Appl. No. 13/598,381, filed Aug. 29, 2012, including prosecution history.
U.S. Appl. No. 13/682,085, filed Nov. 20, 2012, including prosecution history.
U.S. Appl. No. 13/759,963, filed Feb. 5, 2013, including prosecution history.
U.S. Appl. No. 13/911,616, filed Jun. 6, 2013, including prosecution history.
U.S. Appl. No. 13/922,115, filed Jun. 19, 2013, including prosecution history.
U.S. Appl. No. 14/479,214, filed Sep. 5, 2014 including prosecution history.
U.S. Appl. No. 14/643,689, filed Mar. 10, 2015, including prosecution history.
U.S. Appl. No. 15/090,072, filed on Apr. 4, 2016 including prosecution history.
U.S. Appl. No. 60/668,022, filed Apr. 4, 2005, including prosecution history.
U.S. Appl. No. 60/708,206, filed Aug. 15, 2005, including prosecution history.
U.S. Appl. No. 60/902,738, filed Feb. 21, 2007, including prosecution history.
U.S. Appl. No. 60/955,854, filed Aug. 14, 2007, including prosecution history.
Vitrify—(2001). In Chambers 21st Century Dictionary. London. Chambers Harrap. Retrieved May 7, 2009, from http://www.credoreference.com/entry/1236485/.
Vlok, Marie E.: "Kaolin poultice", Manual of Nursing, vol. 1, Basic Nursing, revised ninth edition, p. 269. Copyright Juta & Co, Ltd., Lansdowne, South Africa, first published 1962.
Voet, Donald & Judith: "Molecular Physiology", Biochemistry, p. 1087-1096, vol. 64, 1990, John Wiley & Sons.
Wagner, Holly, "Topical Oxygen Helps Hard-To-Heal Wounds Heal Faster and Better," Jan. 28, 2003, obtained from http://researchnews.osu.edu/archive/oxywound.htm.
Ward, et al., The Journal of TRAUMA Injury, Infection, and Critical Care, Comparison of a New Hemostatic Agent to Current Combat Hemostatic Agents in a Swine Model of Lethal Extremity Arterial Hemorrhage, Aug. 2007, pp. 276-284.
Webster's Dictionary definition of "expose" (1993).
Wound Stat, http://shadowspear.com/vb/showthread.php?t=16586 dated Dec. 22, 2008, last accessed Apr. 16, 2009.
WoundStat found to be potentially hazardous, Army News, news from Iraq . . . , http://armytimes.com/news/2009/04/army_woundstat_042009w/, posted Apr. 20, 2009, last accessed Apr. 20, 2009.
Wright, J. Barry et al.: "Wound management in an era of increasing bacterial antibiotic resistance: A role for topical silver treatment", American Journal of Infection Control, vol. 26 (6), 1998, pp. 572-577.
Wright, J.K. et al. "Thermal Injury Resulting from Application of a GranularMineral Hemostatic Agent." The Journal of Trauma Injury, Infection, and Critical Care. 2004. pp. 224-230. vol. 57, No. 2.
Wu, Jing-Nuan, "An Illustrated Chinese Materia Medica," Oxford University Press, Inc. 2005 (13 pages).
Xinrong, Traditional Chinese Medicine, A Manual from A-Z, Symptoms, Therapy and Herbal Remedies, [ISBN 3 540 42846 1], p. 470 (total 3 pages), Springer-Verlag Berlin Heidelberg 2003.
Yanchi, The Essential Book of Traditional Chinese Medicine, vol. 2: Clinical Practice, p. 155-157 (Traditional Chinese Prescriptions), 142-143 (Chinese Medicinal Herbs) total 8 pages. [ISBN 0 231 06518 3 9v.2] 1988.
Z-Medica Corporation 510(k) Summary, QuikClot eX, Oct. 4, 2007.
Acheson, et al.: "Comparison of Hemorrage Control Agents Applied to Lethal Extremity Arterial Hemorrages in Swine," The Journal of TRAUMA, Injury, Infection, and Critical Care, 2005:59 865-875.
Dubick et al.: "New Technologies for Treating Severe Bleeding in Far-Forward Combat Areas," RTO-MP-HFM-182, 21-1 to 21-12. NATO/OTAN, US Army Institute of Surgical Research.
European Exam Report, re EP Application No. 13806931.5, dated Jul. 13, 2017.
Pusateri, et al.: "Application of a Granular Mineral-Based Hemostatic Agent (QuickClot) to Reduce Blood Loss After Grade V Liver Injury in Swine," The Journal of TRAUMA, Injuary, Infection, and Critical Care, 2004:57 555-562.
Pusateri, et al.: "Effect of a Chitosan-Based Hemostatic Dressing on Blood Loss and Survival in a Model of Sever Henous Hemorrage and Hepatic Injury in Swine," The Journal of TRAUMA , Injury, Infection, and Critical Care, 2003: 54 177-182.
Stasilon, Wikipedia—definiation 2011.

(56) References Cited

OTHER PUBLICATIONS

Traditional Chinese Medicine, A Manual from A-Z. Symptoms, Therapy and Herbal Remedies. Springer-Verlag Berlin Heidelberg 2003.
U.S. Appl. No. 14/995,592, filed Jan. 14, 2016 including prosecution history.
U.S. Appl. No. 15/641,999 filed Jul. 5, 2017 including prosecution history.
Ward, Declaration and CV, signed Jul. 19, 2012.
Yanchi, Liu: "Drug Forms: Their Administration and Actions," The Essential Book of Traditional Chinese Medicine 7, vol. 2: Clinical Practice. 1988.
Segal, H. C. et al., The Effects of Alginate and Non-Alginate Wound Dressings on Blood Coagulation and Platelet Activation, Journal of Biomaterials Applications, Jan. 1998, vol. 12, No. 3, pp. 249-257.
U.S. Appl. No. 15/950,832, filed Apr. 11, 2018 including prosecution history.
U.S. Appl. No. 15/995,672, filed Jun. 1, 2018 including prosecution history.
Oh, Seung-Taek et al.: "The Preparation of Plyurethane Foam Combined with pH-sensitive Alginate/Bentonite Hydrogel for Wound Dressings," Fibers and Polymers 2011, vol. 12. No. 2, 159-165.
Revised Pharmaceutical Product Additive Handbook, Yakuji Hosha Inc., Feb. 28, 2007, first printing, p. 41-44 (publication showing well-known technology).
U.S. Appl. No. 12/568,561, filed Sep. 28, 2009 including prosecution history.
Le et al.: "Recent development in fibres and materials for wound management," Indian Journal of Fibre & Textile Research, 1997.
U.S. Appl. No. 15/841,843, filed Dec. 14, 2017, including prosecution history.
Kamala, K., et al. "Extraction and Characterization of Water Soluble Chitosan from Parapeneopsis Stylifera Shrimp Shell Waste and its Antibacterial Activity," Int. J. Sci. Res. Pub., 3(4), 2013, 1-8.
Cease and Desist Letter from Z-Medica, LLC to Protégé Biomedical, LLC, dated Oct. 10, 2018.
Plaintiff Protégé Biomedical, LLC's Complaint, dated Nov. 19, 2018 ("Complaint"), filed against Defendant Z-Medica, LLC, in Case No. 0:18-cv-03227.
Plaintiff Protégé Biomedical, LLC's First Amended Complaint (and Exhibits A and B), dated Jan. 25, 2019 ("First Amended Complaint"), in Case No. 0:18-cv-03227.
Defendant Z-Medica, LLC's Motion to Dismiss Plaintiff's First Amended Complaint, dated Feb. 7, 2019 in Case No. 0:18-cv-03227.
Defendant Z-Medica, LLC's Memorandum of Law in Support of Defendant's Motion to Dismiss Plaintiff's First Amended Complaint, dated Feb. 7, 2019 in Case No. 0:18-cv-03227.
Declaration of Dina Dubey submitted with Memorandum of Law in Support of Defendant's Motion to Dismiss Plaintiff's First Amended Complaint, dated Feb. 7, 2019 in Case No. 0:18-cv-03227.
Plaintiff Protégé Biomedical, LLC's Response Memorandum of Law in Opposition to Defendant's Motion to Dismiss Under Fed. R. Civ. P. 12(6)(2) and 12(6)(6), dated Feb. 28, 2019, in Case No. 0:18-cv-03227.
Defendant Z-Medica, LLC's Reply in Support of Defendant's Motion to Dismiss Plaintiff's First Amended Complaint, dated Mar. 14, 2019 in Case No. 0:18-cv-03227.
Declaration of Dina Dubey submitted with Reply in Support of Defendant's Motion to Dismiss Plaintiff's First Amended Complaint, dated Mar. 14, 2019 in Case No. 0:18-cv-03227.
Plaintiff Protégé Biomedical, LLC's Motion for Injunctive Relief and Expedited Handling of the Case, dated Dec. 12, 2018, in Case No. 0:18-cv-03227.
Plaintiff Protégé Biomedical, LLC's Memorandum of Law in Support of Protege Biomedical's Motion for Injunctive Relief and Expedited Handling of the Case, dated Dec. 12, 2018, in Case No. 0:18-cv-03227.
Declaration of Susan Wuollett submitted with Memorandum of Law in Support of Protege Biomedical's Motion for Injunctive Relief and Expedited Handling of the Case, dated Dec. 12, 2018, in Case No. 0:18-cv-03227.
Plaintiff Protégé Biomedical, LLC's Notice of Withdrawal of Plaintiff's Motion for Injunctive Relief Filed Dec. 12, 2018 Without Prejudice, dated Jan. 14, 2019, in Case No. 0:18-cv-03227.
A Rule 26(f) Pretrial Conference Report and its Exhibits, dated Feb. 26, 2019, in Case No. 0:18-cv-03227.
A Docket Report from Mar. 21, 2019, in Case No. 0:18-cv-03227.
Calcium Alginate, definition—Prepared at the 49th JECFA (1997), published in FNP 52 Add 5 (1997) superseding specifications prepared at the 44th JECFA (1995), published in FNP52, Add 3 (1995). An ADI 'not specified' was established at the 39th JECFA (1992).
European Extended Search Report, re EP Application No. 18183513. 3, dated Nov. 7, 2018.
Qin, et al.: "Water-solubility of chitosan and its antimicrobial activity," Carbohydrate Polymers 63 (2006) 367-374.
Pretrial Scheduling Order, Dated Filed Mar. 26, 2019 in Case 0:18-cv-03227-JRT-HB; pp. 1-19.
Defendant Z-Medica, LLC's Memorandum in Support of D's First Motion to Compel, dated Apr. 22, 2019, in Case No. 0:18-cv-03227 (32 pages).
Dec of Charles Nauen in Support of Defendant Z-Medica, LLC's Memorandum in Support of D's First Motion to Compel, dated Apr. 22, 2019, in Case No. 0:18-cv-03227 (2 pages).
Exhibits A-C for Dec of Charles Nauen in Support of Defendant Z-Medica, LLC's Memorandum in Support of D's First Motion to Compel, dated Apr. 22, 2019, in Case No. 0:18-cv-03227 (73 pages).
Exhibit D for Dec of Charles Nauen in Support of Defendant Z-Medica, LLC's Memorandum in Support of D's First Motion to Compel, dated Apr. 22, 2019, in Case No. 0:18-cv-03227 (31 pages).
Exhibit E for Dec of Charles Nauen in Support of Defendant Z-Medica, LLC's Memorandum in Support of D's First Motion to Compel, dated Apr. 22, 2019, in Case No. 0:18-cv-03227 (6 pages).
Exhibit F for Dec of Charles Nauen in Support of Defendant Z-Medica, LLC's Memorandum in Support of D's First Motion to Compel, dated Apr. 22, 2019, in Case No. 0:18-cv-03227 (16 pages).
Exhibit G for Dec of Charles Nauen in Support of Defendant Z-Medica, LLC's Memorandum in Support of D's First Motion to Compel, dated Apr. 22, 2019, in Case No. 0:18-cv-03227 (55 pages).
Plaintiff Protégé Biomedical, LLC's Motion to Compel, dated Apr. 22, 2019, in Case No. 0:18-cv-03227 (21 pages).
Dec of Laura Conley in Support of Plaintiff Protégé Biomedical, LLC's Motion to Compel, dated Apr. 22, 2019, in Case No. 0:18-cv-03227 (3 pages).
Exhibit C for Dec of Laura Conley in Support of Plaintiff Protégé Biomedical, LLC's Motion to Compel, dated Apr. 22, 2019, in Case No. 0:18-cv-03227 (7 pages).
Exhibit D for Dec of Laura Conley in Support of Plaintiff Protégé Biomedical, LLC's Motion to Compel, dated Apr. 22, 2019, in Case No. 0:18-cv-03227 (31 pages).
Exhibit E for Dec of Laura Conley in Support of Plaintiff Protégé Biomedical, LLC's Motion to Compel, dated Apr. 22, 2019, in Case No. 0:18-cv-03227 (30 pages).
Exhibit F for Dec of Laura Conley in Support of Plaintiff Protégé Biomedical, LLC's Motion to Compel, dated Apr. 22, 2019, in Case No. 0:18-cv-03227 (20 pages).
Exhibit I for Dec of Laura Conley in Support of Plaintiff Protégé Biomedical, LLC's Motion to Compel, dated Apr. 22, 2019, in Case No. 0:18-cv-03227 (3 pages).
Exhibit J for Dec of Laura Conley in Support of Plaintiff Protégé Biomedical, LLC's Motion to Compel, dated Apr. 22, 2019, in Case No. 0:18-cv-03227 (3 pages).
Exhibit K for Dec of Laura Conley in Support of Plaintiff Protégé Biomedical, LLC's Motion to Compel, dated Apr. 22, 2019, in Case No. 0:18-cv-03227 (16 pages).

(56) References Cited

OTHER PUBLICATIONS

Exhibit L for Dec of Laura Conley in Support of Plaintiff Protégé Biomedical, LLC's Motion to Compel, dated Apr. 22, 2019, in Case No. 0:18-cv-03227 (6 pages).
Exhibit N For Dec of Laura Conley in Support of Plaintiff Protégé Biomedical, LLC's Motion to Compel, dated Apr. 22, 2019, in Case No. 0:18-cv-03227 (5 pages).
Defendant Z-Medica, LLC's Opposition to Plaintiff's Motion to Compel, dated Apr. 23, 2019, in Case No. 0:18-cv-03227 (3 pages).
Plaintiff Protégé Biomedical, LLC's Combined Response Reply Brief on Motions to Compel, dated Apr. 30, 2019, in Case No. 0:18-cv-03227 (15 pages).
Plaintiff Protégé Biomedical, LLC's Interrogatory Responses, dated Apr. 30, 2019, in Case No. 0:18-cv-03227 (51 pages).
Plaintiff Protégé Biomedical, LLC's Memorandum in Support of Leave to Amend Complaint, dated May 3, 2019, in Case No. 0:18-cv-03227 (6 pages).
Dec of Joseph Balthazor for in Support of Plaintiff Protégé Biomedical, LLC's Memorandum in Support of Leave to Amend Complaint, dated May 3, 2019, in Case No. 0:18-cv-03227 (3 pages).
Plaintiff Protégé Biomedical, LLC's Second Amended Complaint, dated May 3, 2019, in Case No. 0:18-cv-03227 (48 pages).
Order Approving Stipulation to Stay Pending Ruling on Motion to Dismiss, dated May 27, 2019, in Case No. 0:18-cv-03227 (1 page).
Opinion and Order Regarding Defendant Z-Medica's Motion to Dismiss, dated Jul. 24, 2019, in Case No. 0:18 cv-03227 (29 pages).
Defendant Z-Medica LLC's Answer to Amended Complaint, dated Aug. 21, 2019, in Case No. 0:18 cv-03227 (67 pages).
Plaintiff Protege Biomedical, LLC's Reply and Affirmative Defenses, dated Sep. 11, 2019, in Case No. 0:18-cv-03227 (8 pages).
Settlement Conference Minutes, dated Sep. 18, 2019, in Case No. 0:18-cv-03227 (2 pages).
Protégé Biomedica, Llc Invalidity Contentions of Z-Medica, LLC U.S. Patent No. 10,086,106, in Case No. 0:18-cv-03227, dated Oct. 11, 2019 (363 pages).
Defendant Z-Medica LLC's Motion for Leave to Amend Initial Infringement Claim Charts date Nov. 8, 2019, in Case No. 0:18 cv-03227 (2 pages).
Defendant Z-Medica LLC's Response to Protégé Biomedical, LLC's Invalidity Contentions Regarding U.S. Patent No. 10,086,106, in Case No. 0:18-cv-03227, (251 pages).
Joint Claim Construction Statement, dated Nov. 13, 2019, in Case No. 0:18-cv-03227 and Exhibits A-F thereof (28 pages).
Plaintiff Protege Biomedical, LLC's Response Memorandum in Opposition to Z-Medica, LLC's Motion for Leave to Amend Initial Infringement Claim Charts, dated Nov. 15, 2019, in Case No. 0:18-cv-03227 (8 pages).
Declaration of Andrew S. Dosdall in Support of Defendant's Motion for Leave to Amend initial Infringement Claim Charts, dated Nov. 15, 2019 (2 pages).
Statement Regarding Exhibit a Accompanying Declaration of Andrew S. Dosdall, dated Nov. 15, 2019 (2 pages).
A Docket Report from Dec. 16, 2019, in Case No. 0:18-cv-03227 (25 pages).
Joint Claim Construction Statement, dated Jan. 15, 2020, in Case No. 0:18-cv-03227 (11 pages).
Counterclaim Plaintiff Z-Medica, LLC's Opening Claim Construction Brief, dated Jan. 27, 2020, in Case No. 0:18-cv-03227 (17 pages).
Declaration of Ali Razai and Exhibits in Support of Counterclaim Plaintiff Z-Medica, LLC's Claim Construction Brief, dated Jan. 27, 2020, in Case No. 0:18-cv-03227 (167 pages).
Declaration of Douglas Loy and Exhibits in Support of Counterclaim Plaintiff Z-Medica, LLC's Claim Construction Brief, dated Jan. 27, 2020, in Case No. 0:18-cv-03227 (44 pages).
Plaintiff Protégé Biomedical, LLC's Opening Claim Construction Brief, dated Jan. 27, 2020, in Case No. 0:18-cv-03227 (39 pages).
Declaration of Andrew Dosdall and Exhibits in Support of Plaintiff Protégé Biomedical, LLC's Opening Claim Construction Brief, dated Jan. 27, 2020, in Case No. 0:18-cv-03227 (88 pages).
Plaintiff Protégé Biomedical, LLC's Motion to Compel, dated Jan. 30, 2020, in Case No. 0:18-cv-03227 (2 pages).
Plaintiff Protégé Biomedical, LLC's Memorandum in Support of Motion to Compel, dated Jan. 30, 2020, in Case No. 0:18-cv-03227 (20 pages).
Declaration of Balthazor and Exhibits in Support of Plaintiff Protégé Biomedical, LLC's Motion to Compel, dated Jan. 30, 2020, in Case No. 0:18-cv-03227 (25 pages).
Defendant Z-Medica, LLC's Motion to Compel, dated Jan. 31, 2020, in Case No. 0:18-cv-03227 (2 pages).
Defendant Z-Medica, LLC's Memorandum in Support of Motion to Compel, dated Jan. 30, 2020, in Case No. 0:18-cv-03227 (35 pages).
Declaration of Charles Nauen and Exhibits in Support of Defendant Z-Medica, LLC's Motion to Compel, dated Jan. 30, 2020, in Case No. 0:18-cv-03227 (25 pages).
Defendant Z-Medica, LLC's Opposition to P's Motion to Compel, dated Feb. 6, 2020, in Case No. 0:18-cv-03227 (48 pages).
Plaintiff Protégé Biomedical, LLC's Opposition to D's Motion to Compel, dated Feb. 7, 2020, in Case No. 0:18-cv-03227 (26 pages).
Exhibit for Plaintiff Protégé Biomedical, LLC's Opposition to D's Motion to Compel, dated Feb. 7, 2020, in Case No. 0:18-cv-03227 (26 pages).
Plaintiff Protégé Biomedical, LLC's Responsive Claim Construction Brief, dated Feb. 10, 2020, in Case No. 0:18-cv-03227 (10 pages).
Counterclaim Plaintiff Z-Medica, LLC's Responsive Claim Construction Brief, dated Feb. 10, 2020, in Case No. 0:18-cv-03227 (35 pages).
Second Declaration of Ali Razai in Support of Counterclaim Plaintiff Z-Medica, LLC's Responsive Claim Construction Brief, dated Feb. 10, 2020, in Case No. 0:18-cv-03227 (4 pages).
Declaration of Andrew Dosdall and Exhibits in Opposition of Defendant Z-Medica, LLC's Second Motion to Compel, dated Feb. 18, 2020, in Case No. 0:18-cv-03227 (12 pages).
Letter to Magistrate Judge Regarding Defendant Z-Medica, LLC's Second Motion to Compel dated Feb. 21, 2020, in Case No. 0:18-cv-03227 (3 pages).
Third Amended pretrial Case Management Order, dated Feb. 21, 2020, in Case No. 0:18-cv-03227 (22 pages).
Plaintiff Protégé Biomedical, LLC's Memorandum of Law in Support of Leave to Amend First Amended Complaint, dated Mar. 2, 2020, in Case No. 0:18-cv-03227 (15 pages).
Declaration Balthazor of in Support of Plaintiff Protégé Biomedical, LLC's Memorandum of Law in Support of Leave to Amend First Amended Complaint dated Mar. 2, 2020, in Case No. 0:18-cv-03227 (187 pages).
Exhibit A to Balthazor Declaration for Plaintiff Protégé Biomedical, LLC's Second Amended Complaint, dated Mar. 3, 2020, in Case No. 0:18-cv-03227 (183 pages).
A Docket Report from Mar. 13, 2020, in Case No. 0:18-cv-03227 (33 pages).
Defendant Z-Medica, LLC's Partial Opposition to P's Motion for Leave to Amend, dated Mar. 20, 2020, in Case No. 0:18-cv-03227 (36 pages).
Declaration of Charles N. Nauen and Exhibits in Support of Defendant Z-Medica, LLC's Partial Opposition to P's Motion for Leave to Amend, dated Mar. 20, 2020, in Case No. 0:18-cv-03227 (15 pages).
Redacted Exhibit C of Declaration of Charles N. Nauen in Support of Defendant Z-Medica, LLC's Partial Opposition to P's Motion for Leave to Amend, dated Mar. 20, 2020, in Case No. 0:18-cv-03227 (8 pages).
Stipulation to Amend Schedule, dated Mar. 27, 2020, in Case No. 0:18-cv-03227 (4 pages).
Amended Joint Claim Construction Statement, dated Mar. 27, 2020, in Case No. 0:18-cv-03227 (5 pages).
Joint Claim Construction Letter, dated Mar. 27, 2020, in Case No. 0:18-cv-03227 (2 pages).
Order to Amend Schedule, dated Mar. 30, 2020, in Case No. 0:18-cv-03227 (2 pages).

(56) References Cited

OTHER PUBLICATIONS

Plaintiff Protégé Biomedical, LLC's Objections to the Magistrate Judge's Mar. 17, 2020 Order on Its Motion to Compel the Production of Privileged Documents, dated Mar. 31, 2020, in Case No. 0:18-cv-03227 (16 pages).
Declaration of Laura Conley and Exhibits in Support of Plaintiff Protégé Biomedical, LLC's Objections to the Magistrate Judge's Mar. 17, 2020 Order on Its Motion to Compel the Production of Privileged Documents, dated Mar. 31, 2020, in Case No. 0:18-cv-03227 (19 pages).
Declaration of Philip O'Beirne and Exhibits in Support of Defendant Z-Medica, LLC's Submission for Attorneys' Fees, dated Mar. 31, 2020, in Case No. 0:18-cv-03227 (10 pages).
Plaintiff Protégé Biomedical, LLC's Reply Memorandum in Support of Leave to Amend, dated Apr. 2, 2020, in Case No. 0:18-cv-03227 (35 pages).
Order Regarding Payment of D's Attorney Fees, dated Apr. 6, 2020, in Case No. 0:18-cv-03227 (2 pages).
Defendant Z-Medica, LLC's Sur-Reply in Support Partial Opposition to P's Motion for Leave to Amend, dated Apr. 6, 2020, in Case No. 0:18-cv-03227 (18 pages).
Declaration of Charles N. Nauen and Exhibits in Support of Defendant Z-Medica, LLC's Sur-Reply, dated Apr. 6, 2020, in Case No. 0:18-cv-03227 (1 page).
A Docket Report from Apr. 10, 2020, in Case No. 0:18-cv-03227 (32).
Order denying Plaintiff's Motion to Compel Discovery, and granting Defendant's request for sanctions as to the cost of Z-Medica's reasonable fees and expenses incurred in opposing the motion, but denied as to any further relief, dated Mar. 17, 2020, in Case No. 0:18-cv-03227 (13 pages).
Declaration of Jack Y. Perry in Support of Plaintiff Protégé Biomedical, LLC's in Support of P's Motion for Leave to Amend First Amended Complaint, dated Apr. 13, 2020, in Case No. 0:18-cv-03227 (1 page).
Declaration of Philip O'Beirne in Support of Defendant Z-Medica, LLC's Opposition to P's Motion for Leave to Amend, dated Apr. 14, 2020, in Case No. 0:18-cv-03227 (3 pages).
Redacted Response by Defendant Z-Medica, LLC's in Response to P's Motions of Mar. 17, 2020, dated Apr. 14, 2020, in Case No. 0:18-cv-03227 (17 pages).
Supplemental Declaration of Jack Y. Perry in Support of Plaintiff Protégé Biomedical, LLC's in Support of P's Motion for Leave to Amend First Amended Complaint, dated Apr. 15, 2020, in Case No. 0:18-cv-03227 (3 pages).
Plaintiff Protégé Biomedical, LLC's Request for Oral Hearing, dated Apr. 17, 2020, in Case No. 0:18-cv-03227 (2 pages).
Stipulation re 183 Scheduling Order, by Z-Medica, LLC. Jointly Signed by Protege Biomedical, Llc., dated Jun. 3, 2020, in Case No. 0:18-cv-03227 (3 pages).
Declaration of Laura Conley in Support of Plaintiff's Third Motion to Compel (and exhibits), dated Jun. 8, 2020, in Case No. 0:18-cv-03227 (77 pages).
Declaration of Charles N. Nauen (and Exhibits) in Support of Defendant's Opposition to Protégé's Third Motion to Compel, dated Jun. 15, 2020, in Case No. 0:18-cv-03227 (42 pages).
Defendant Z-Medica's Response to Protégé's Objections to the Magistrate Judge's Order on Its Motion to for leave to Amend its First Amended Complaint, dated Jun. 23, 2020, in Case No. 0:18-cv-03227 (15 pages).
Memorandum Opinion and Order Affirming Magistrate Judge Order and overruling 316 Objection by Protege Biomedical, LLC, dated Jul. 6, 2020, in Case No. 0:18-cv-03227 (8 pages).
A Docket Report from Jul. 20, 2020, in Case No. 0:18-cv-03227 (37 pages).
Final Consent Judgment and Permanent Injunction, dated Aug. 13, 2020, in Case No. 0:18-cv-03227 (4 pages).
A Docket Report from Sep. 9, 2020, in Case No. 0:18-cv-03227 (38 pages).
Statement of Charles Nauen for Defendant Z-Medica, LLC that Entire Documents are Confidential or Impracticable to Redact, dated Mar. 20 2020, in Case No. 0:18-cv-03227 (2 pages).
Proposed Order Denying P's Motion to Leave to Amend, dated Mar. 20, 2020, in Case No. 0:18-cv-03227 (15 pages).
Plaintiff Protégé Biomedical, LLC's Objections to the Magistrate Judge's May 26, 2020 Order on Its Motion to for leave to Amend its First Amended Complaint, dated Jun. 9, 2020, in Case No. 0:18-cv-03227 (16 pages).
Order on Stipulation to Amend Case Schedule, dated Jun. 8, 2020, in Case No. 0:18-cv-03227 (2 pages).

* cited by examiner

HEMOSTATIC DEVICES

CROSS REFERENCE TO RELATED APPLICATIONS

This application is a continuation of U.S. patent application Ser. No. 15/071,520, filed Mar. 16, 2016, entitled "Hemostatic Devices", which is a continuation of U.S. patent application Ser. No. 14/720,142, filed May 22, 2015, entitled "Hemostatic Devices", which is a continuation of U.S. patent application Ser. No. 13/922,115, filed Jun. 19, 2013, entitled "Hemostatic Devices," which claims the benefit, under 35 U.S.C. § 119(e), of U.S. Provisional Patent Application Ser. No. 61/663,412, filed Jun. 22, 2012, entitled "Hemostatic Devices" and U.S. Provisional Patent Application Ser. No. 61/754,129, filed Jan. 18, 2013, entitled "Hemostatic Devices." The contents of all of the above-referenced applications are incorporated herein by reference in their entireties.

FIELD OF THE INVENTION

The present invention relates generally to agents and devices for promoting hemostasis, and more particularly, to hemostatic bandages and wound dressings.

DESCRIPTION OF THE RELATED ART

Blood is a liquid tissue that includes red cells, white cells, corpuscles, and platelets dispersed in a liquid phase. The liquid phase is plasma, which includes acids, lipids, solubilized electrolytes, and proteins. The proteins are suspended in the liquid phase and can be separated out of the liquid phase by any of a variety of methods such as filtration, centrifugation, electrophoresis, and immunochemical techniques. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can be wounded. Often bleeding is associated with such wounds. In some circumstances, the wound and the bleeding are minor, and normal blood clotting functions in addition to the application of simple first aid are all that is required. Unfortunately, in other circumstances substantial bleeding can occur. These situations usually require specialized equipment and materials as well as personnel trained to administer appropriate aid. If such aid is not readily available, excessive blood loss can occur. When bleeding is severe, sometimes the immediate availability of equipment and trained personnel is still insufficient to stanch the flow of blood in a timely manner.

Moreover, severe wounds can often be inflicted in remote areas or in situations such as on a battlefield, where adequate medical assistance is not immediately available. In these instances, it can be useful to stop bleeding, even in less severe wounds, long enough to allow the injured person or animal to receive medical attention.

In an effort to address the above-described problems, materials have been developed for controlling excessive bleeding in situations where conventional aid is unavailable or less than optimally effective. Although these materials have been shown to be somewhat successful, they are sometimes not effective enough for traumatic wounds and tend to be expensive. Furthermore, these materials are sometimes ineffective in some situations, unstable at high temperatures, and can be difficult to apply as well as remove from a wound.

Similarly, other available hemostatic products or devices may include a binder material to bind a hemostatic material to the device. This configuration can be used to successfully deliver the hemostatic material to a wound; however, the blood or exudate from the wound can dissolve a substantial portion of the binder material, thereby potentially allowing a significant portion of the hemostatic agent to be separated from the device.

Bleeding can also be a problem during surgical procedures. Bleeding is sometimes addressed by suturing or stapling an incision or an internally bleeding area, as well as by using a gauze, sponge, or other material to exert pressure against the bleed site or absorb the blood. However, when the bleeding becomes excessive, these measures may not be sufficient to stop the blood flow as quickly as desired.

SUMMARY OF THE INVENTION

According to some embodiments, a hemostatic device comprises a substrate (such as a gauze substrate or a sponge substrate), at least one type of hemostatic material disposed on and/or in the substrate, and a binder such as a cross-linked material (e.g., calcium alginate or the like) disposed on and/or in the substrate to bind the hemostatic material to the substrate in a manner that is resistant to solubility in fluids such as body fluids, blood, fluids at physiological pH and salt such as Earle's balanced salt solution, saline, and/or water. The hemostatic material can be applied to the substrate in a hemostatically effective amount and in a hemostatically effective form. In some embodiments, the binder can be formed from an alginate, such as sodium alginate, that is cross-linked with a salt, such as calcium chloride, in the presence of a hemostatic material, such as a clay (e.g., kaolin), on a gauze or a sponge to thereby substantially entrap or bind the clay material to the gauze. In some embodiments, such as those in which the alginate comprises a high concentration of guluronate monomers (e.g., a guluronate to mannuronate ratio of greater than or equal to about 50%), the binder can be resistant to solubility in fluids such as saline or blood. The binder may itself be a hemostatic agent which may or may not be used in combination with other hemostatic agents such as clay material.

In some embodiments, when the hemostatic device is used to treat a bleeding wound, it is configured so that the hemostatic device contacts the surface of a bleeding wound and at least a portion of the hemostatic material on and/or in the substrate comes into direct contact with blood emanating from the wound surface to initiate or accelerate the clotting process, and the binder substantially retains the hemostatic material on and/or in the substrate even when exposed to fluids such as blood.

According to some embodiments, the use of a suitable binder in conjunction with a hemostatic agent can substantially retain the hemostatic agent on or within the substrate of a hemostatic device. Such retention may be advantageous during manufacturing, packaging, and transport of a hemostatic device, and may also help during application and removal of the device from a wound. For example, the use of an appropriate binder material can reduce the amount of hemostatic agent that separates from or sloughs off the device when exposed to fluids such as blood or that is dissolved by the blood or other fluids. This feature can enable a care giver to know how much hemostatic material is being applied to a wound.

In some embodiments, a desirable binder can be: (a) biocompatible, in that it is regarded as safe to use in medical applications; (b) convenient and cost-effective for manufacturing, in that it is available in steady supply, at reasonable cost, and can be processed relatively inexpensively and does not require the use of toxic or otherwise undesirable or expensive chemicals for processing; (c) resistant to solubility in saline and/or body fluids; and (d) highly flexible and conformable when applied in a hemostatically effective amount in and/or on a substrate so that the resulting hemostatic device is not excessively stiff and can readily conform to, be packed within, and/or wrapped around a wound surface or wound cavity without producing significant bulges, gaps, or voids; and/or (e) can provide a carrier in which a hemostatic agent can freely interface directly with blood, such as by providing a porous surface that permits entry of blood through the binder directly to the hemostatic agent or by providing a surface on which the hemostatic agent is externally protruding so as to directly contact blood.

In some embodiments, the devices and agents are easily applied to open wounds. Particularly when the hemostatic agent is retained in a mesh or similar device, or when it is incorporated into a woven or non-woven structure to form a gauze, the device can be readily packaged in and removed from a sterilized container and placed, packed into, or held directly at the points from which blood emanates to cause clotting.

In some embodiments, an advantage in using a cross-linked binder, such as calcium alginate, in conjunction with a hemostatic agent is that the undesirable adhesion of a hemostatic device to the wound may be reduced. In some embodiments, the device can be easily removed from a wound while maintaining the scab surface generally intact and without breaking a newly formed blood clot or inducing significant new bleeding. Moreover, in some embodiments, the use of devices according to the present disclosure can aid in the overall healing process of a wound. Such features in a hemostatic device of the present disclosure can be enhanced through the selection of appropriate hemostatic agents (e.g., kaolin) and/or binders (e.g., calcium alginate).

In some embodiments, a sponge (e.g., in the form of a sponge matrix) can be used that comprises a medium with regularly or irregularly shaped open and/or closed cells, such as a foamed plastic polymer. A sponge can be highly absorbent, which can permit high loading of a hemostatic agent and associated binder, and high absorption of blood, exudate, or other fluids. In some embodiments, the preparation of a hemostatic device including a sponge comprises one or more steps that are the same as or similar to those employed in the preparation of a gauze, such as any of those described herein. In some embodiments, methods of preparing a sponge matrix include additional or alternative steps to enhance the resulting hemostatic device, such as compressing and permitting expansion of the sponge matrix while applying one or more binders and/or hemostatic agents to improve the absorption thereof into the sponge matrix. Additionally, enhanced methods of absorption can be replaced with or combined with other application processes or techniques, such as a spraying or slot-die method. In some embodiments, spraying or a slot-die method can be used to apply a material such as a hemostatic agent or a release agent to only one surface of the sponge (e.g., a bottom surface or a top surface).

DETAILED DESCRIPTION

Figure 1:
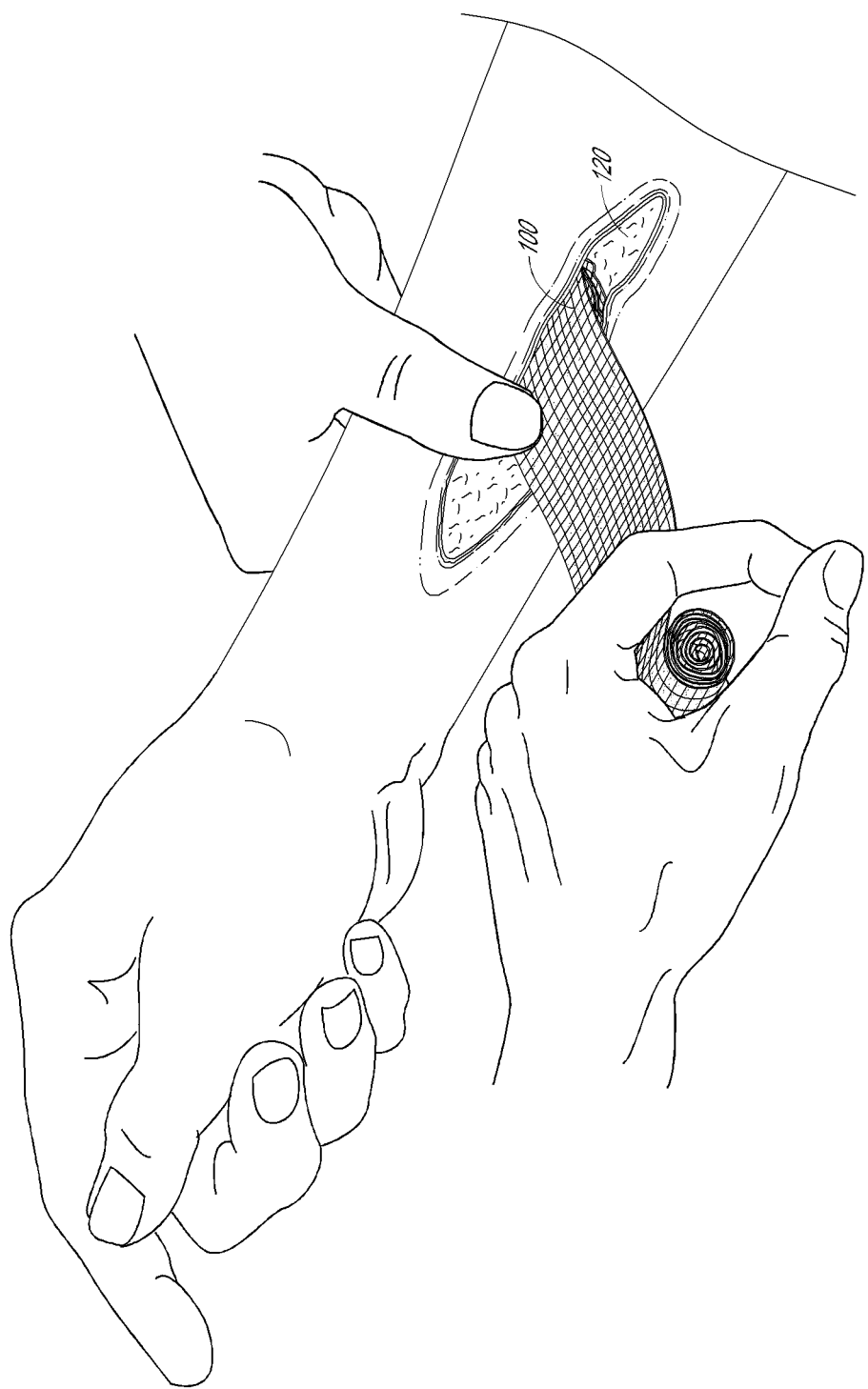
FIG. 1 is a perspective view of a hemostatic device being applied to a wound.

Disclosed herein are hemostatic devices, hemostatic agents, and binding materials that are applicable to bleeding wounds to promote hemostasis and wound healing. It will be understood that any features described herein may be used in combination with one or more of any other disclosed features. Moreover, the specific embodiments disclosed herein are merely preferred embodiments of the present disclosure. No features are essential or indispensable.

In some embodiments of the hemostatic devices disclosed herein, the hemostatic devices are specifically configured for use in the treatment of a bleeding wound by providing a hemostatic effect. The hemostatic agents generally include clay materials or other silica-based materials that, when brought into contact with a bleeding wound, can facilitate clotting. The present invention is not limited to clay, however, as other hemostatic materials such as bioactive glasses, biological hemostats, molecular sieve materials, diatomaceous earth, calcium alginate, chitosan, thrombin, combinations of the foregoing, and the like are within the scope of the present disclosure and can be used in conjunction with the clay or separately as a hemostatic agent. In some embodiments, a suitable hemostatic material may be bio-inert, inexpensive, in steady supply, and easily processed.

The binding materials can include cross-linked materials, such as alginates (e.g., calcium alginate), or similar materials that are capable of substantially retaining a hemostatic agent in or on a hemostatic device even when exposed to a liquid such as blood. In some embodiments, the binder is not substantially dissolved by the liquid with which it is intended to be in contact.

Some suitable binding materials are created from two or more chemical agents that may themselves be formed from two or more chemical constituents. The agents can be brought together in a manner that induces chemical bonding (e.g., ionic, covalent, etc.) between at least two of the more fundamental chemical constituents. For example, an alginate, such as sodium alginate, can be combined with a salt that may form ions of calcium, zinc, barium, aluminum, iron, or zirconium, in combination with chlorine, another halogen, or sulfates. Many other potential crosslinking chemical agents can be used with binders and/or hemostatic agents, including but not limited to: (1) 1-ethyl-3-(3-dimethylaminopropyl) carbodiimide—commonly known as EDC (it is in the carbodiimide family and crosslinks carboxyl to amine groups forming amide bonds); (2) EDC+NHS (N-Hydroxysuccinimide) or EDC+Sulfo-NHS (adding NHS or sulfo-NHS creates more stable amide bonds); (3) Genipin; and/or (4) Glutaraldehyde.

As used in this disclosure, the term "clay" is used in accordance with its ordinary meaning in this field and includes a crystalline form of hydrated aluminum silicate. The crystals of clay are generally irregularly shaped and insoluble in water. The combination of some types of clay with water may produce a mass having some degree of plasticity. Depending upon the type of clay, the combination thereof with water may produce a colloidal gel having thixotropic properties.

In some embodiments, the clay material is kaolin, which includes the mineral "kaolinite." Although the term "kaolin" is used hereinafter to describe some embodiments, it should be understood that kaolinite may also be used in conjunction with or in place of kaolin. The present invention is not limited with regard to kaolin or kaolinite. Many other suitable clay materials can be used, including but not limited to attapulgite, bentonite, phyllosilicates other than kaolinite such as montmorillonite, silicates other than phyllosilicates such as tectosilicates, combinations of the foregoing, combinations of the foregoing with kaolin and/or diatomaceous earth, and the like.

Examples of silicate minerals include nesosilicates or orthosilicates, sorosilicates, cyclosilicates, inosilicates, phyllosilicates, and tectosilicates. Examples of phyllosilicates include members of the serpentine group such as antigorite, chrysotile, and lizardite; members of the clay mineral group such as halloysite, illite, vermiculite, talc, palygorskite, and pryophylilite; mica group minerals such as biotite, muscovite, phlogopite, lepidolite, margarite, glauconite; and the chlorite group minerals. Examples of tectosilicates include members of the quartz group, the feldspar family, the feldspathoid family, the scapolite group, and the zeolite group as well as petalite and analcime.

As used herein, the term "kaolin" is used in accordance with its ordinary meaning in this field. In some embodiments, kaolin includes a soft, earthy aluminosilicate clay (and, more specifically, a dioctahedral phyllosilicate clay) having the chemical formula $Al_2Si_2O_5(OH)_4$. In some embodiments, kaolin is a naturally occurring layered silicate mineral having alternating tetrahedral sheets and octahedral sheets of alumina octahedra linked via the oxygen atoms of hydroxyl groups. In some forms, kaolin can comprise about 50% alumina, about 50% silica, and trace impurities.

One type of kaolin is Edgar's plastic kaolin, which is a water-washed kaolin clay that is mined and processed in and near Edgar, Fla. Edgar's plastic kaolin has desirable plasticity characteristics, is castable, and can produce a thixotropic slurry when mixed with a liquid such as water.

The clay or other hemostatic material of some embodiments may be mixed with or otherwise used in conjunction with other materials to provide additional clotting functions and/or improved efficacy. Such materials include, but are not limited to, magnesium sulfate, sodium metaphosphate, calcium chloride, dextrin, combinations of the foregoing materials, and hydrates of the foregoing materials.

In some embodiments, various materials may be mixed with, associated with, or incorporated into the kaolin or other hemostatic agent to maintain an antiseptic environment at the wound site or to provide functions that are supplemental to the clotting functions of the clay. Exemplary materials that can be used include, but are not limited to, pharmaceutically-active compositions such as antibiotics, antifungal agents, antimicrobial agents, anti-inflammatory agents, analgesics, antihistamines (e.g., cimetidine, chlorpheniramine maleate, diphenhydramine hydrochloride, and promethazine hydrochloride), compounds containing silver or copper ions, combinations of the foregoing, and the like. Other materials that can be incorporated to provide additional hemostatic functions include ascorbic acid, tranexamic acid, rutin, and thrombin. Botanical agents having desirable effects on the wound site may also be added.

For use in some embodiments, the kaolin (or other clay material or diatomaceous earth) can be in particle form. As used herein, "particles" include beads, pellets, granules, rods, or any other surface morphology or combination of surface morphologies. Irrespective of the surface morphology, in some embodiments the particles are about 0.2 mm (millimeters) to about 10 mm, preferably about 0.5 mm to about 5 mm, and more preferably about 1 mm to about 2 mm in average effective diameter. The present invention is not limited in this regard, however, and other particle sizes (e.g., less than about 0.2 mm) are also within the scope of the present disclosure. In some embodiments, the particle size of the kaolin (or other clay material or diatomaceous earth) may be so small so as to be considered powder. If the particle size is considered to be powder, the powder may be impalpable (i.e., tactilely undetectable).

The clay particles can be produced by any of several various methods. Such methods include mixing, extrusion, spheronizing, and the like. Equipment that can be utilized for the mixing, extruding, or spheronizing of the clay is available from Caleva Process Solutions Ltd. in Dorset, United Kingdom. Other methods include the use of a fluid bed or a pelletizing apparatus. Fluid beds for the production of clay particles are available from Glatt Air Technologies in Ramsey, N.J. Disk pelletizers for the production of clay particles are available from Feeco International, Inc., in Green Bay, Wis. Preferably, the clay is extruded through a suitable pelletizing device. The present invention is not limited in this regard, however, as other devices and methods for producing particlized clay are within the scope of the present disclosure.

In some embodiments, the clay material can be particlized, dried, and fired to about 600° C. (degrees Celsius). In order to achieve a suitably homogenous mixture of the clay material to form the particles, a relatively high shear is applied to a mass of the clay material using a suitable mixing apparatus. Prior to shearing, the water content of the clay is measured and adjusted to be about 20% by weight to give a sufficiently workable mixture for extrusion and subsequent handling.

In some embodiments, during the firing of the clay material to about 600C.°, the material is vitrified. Vitrification is effected via repeated melting and cooling cycles to allow the EPK (or other clay material) to be converted into a glassy substance. With increasing numbers of cycles, the crystalline structure is broken down to result in an amorphous composition. According to some embodiments, the amorphous nature of the clay material allows it to maintain its structural integrity when subsequently wetted. As a result, the clay material maintains its structural integrity when wetted during use, for example, when applied to blood. The present invention is not limited to the use of vitrified clays; however, as clay material that has not been vitrified can be used, as well as many other types of hemostatic agents. In particular, unvitrified clay can still be applied to a bleeding wound to provide hemostasis.

Without being limited to any particular theory, it is believed that the cellular clotting mechanism of clay activates certain contact factors when applied to blood. More specifically, kaolin promotes activation of Factor XII and platelet-associated Factor XI thereby accelerating the clotting cascade.

In some embodiments, one or more binders are used in conjunction with one or more hemostatic agents. A binder can substantially retain the hemostatic agent on and/or in a given substrate, and a binder may also aid the hemostatic agent in the blood clotting and/or wound healing process. Moreover, in some embodiments, a suitable binder serves as a release agent allowing a hemostatic device to be more easily removed from a wound when desired.

Many different types of substrates and different combinations of substrates can be used. A substrate can be fibrous, composed of one or more fibers such as string or thread; woven or non-woven; tightly woven textile; mesh; gauze; sponge; sponge matrix; absorbent or non-absorbent; and/or solid or porous. In some fibrous embodiments, the one or more hemostatic agents can be coated onto a pre-existing fiber and/or included in the constituents that comprise the fundamental structure of the fiber during the manufacturing process of the fiber itself. In some embodiments, one or more fibers comprise multiple components, such as a first generally linearly continuous component that has high structural strength and integrity, and one or more additional generally linearly continuous components that comprise additives or alternative constituents with one or more hemostatic or other therapeutic agents that may have low structural strength or integrity. In some embodiments, combination or compound substrates can be used, such as a gauze and a sponge matrix; or a gauze formed of hemostatically integrated fibers; or a tightly woven textile (e.g., formed of hemostatically integrated fibers) and a gauze and/or a sponge, etc. The components of the combination or compound substrates can be attached to or integrated with each other in many different ways. For example, the components can be adhered, glued, thermally bonded, chemically bonded, stitched, stapled, cross-linked, and/or woven together. Any reference in this disclosure to the use of any particular type or example of a substrate should be understood to include and apply to all suitable substrates generally.

In some embodiments, the use of a binder substantially suppresses or substantially mitigates dust that could result from or accompany a hemostatic material, retaining substantially all of the hemostatic material on the substrate. This provides more hemostatic material for blood clotting purposes. It also produces a cleaner, easier-to-use, and more therapeutically effective product when a user or caregiver pulls the hemostatic device from its packaging for application to a wound.

A biocompatible crosslinked material, such as calcium alginate, can be used as a binder. In some embodiments, calcium alginate is a water-insoluble substance that can be created through the addition of aqueous calcium chloride to aqueous sodium alginate. "Alginate" is used in its ordinary sense and includes algin, the salts of alginic acid, and the derivatives of alginic acid and alginic acid itself. In some embodiments, alginate can be obtained from the cell walls of brown algae as the calcium, magnesium, and sodium salts of alginic acid. Some commercial varieties of alginate can be extracted from seaweed. Sodium alginate is a natural polyanionic copolymer that can be extracted from brown seaweed and can comprise guluronic and mannuronic acid components. In some embodiments, sodium, potassium, ammonium, and magnesium alginates are water soluble. Calcium chloride can be used to crosslink sodium alginate to form a stable, and in some cases water-insoluble material, namely calcium alginate.

Alginate is a copolymer of guluronate (G) and mannuronate (M) monomers. The G and M units are usually joined together as GG, MM, and MG/GM blocks. The proportion, distribution, and length of these blocks determine the chemical and physical properties of alginate molecules. In some embodiments, an alginate high in G and GG contents can form more stable and less saline-soluble and blood-soluble binders than those high in M and MM contents. In some embodiments of "high-G alginate," there are more guluronate monomers present than other types of monomers or there are more guluronate monomers present than mannuronate monomers. For example, a high-G alginate can include at least about 50% or at least about 65% of the alginate monomers as guluronate (e.g., in a GG or GM formation) by molar percentage or by weight percentage.

In some embodiments, the highest levels of GG fractions are produced from the stems of brown algae. Guluronate monomers can react with calcium to create an "egg-box" like structure enabling the alginate to form a strong, generally water insoluble bond. High-G alginates are available from multiple sources.

Regions of guluronate monomers, G-blocks, in one alginate molecule can be linked to a similar region in another alginate molecule by means of calcium ions or other multivalent cations. The divalent calcium cation, $Ca^{2+}$, can fit into the guluronate block structure. This can bind the alginate polymers together by forming junction zones, resulting in the gelation of the solution. An alginate having a higher G content generally produces a more stable alginate that is less likely to dissolve in fluids particularly blood or saline. When used in a wound or on a hemostatic device placed in or on a wound, this dressing allows easier removal of the device from the wound and minimizes or reduces tissue trauma and discomfort in some embodiments.

Some forms of alginate used in the hemostatic devices disclosed herein may be considered to be partly in a solid and partly in a solution state, the junction zones representing the solid state. After crosslinking, water, one or more hemostatic agents, or other materials can become physically entrapped within the alginate matrix. In some embodiments, a hemostatic device can comprise a coating on the substrate formed by applying during the manufacturing stage kaolin, sodium alginate, and a biomaterial selected from the group comprising collagen, acid soluble collagen, gelatin, chitosan, carboxymethylcellulose, and hyaluronan. In some embodiments, a hemostatic coating on the substrate is bound to the substrate by forming ionic or covalent bonds between the coating and the substrate or between at least two agents that are applied to the substrate. In some embodiments, a coating on the substrate formed by crosslinking at least two agents and generally entrapping or generally immobilizing another agent from the group comprising a hemostatic agent, a wound healing agent, and an anesthetic agent.

Some alginates are cold soluble in water and develop into gels when exposed to calcium ions. Unlike most gelling agents, alginates typically do not require a heating and cooling process to form a gel. By adjusting formulations, alginate gels offer a range of structures, from firm and brittle to solid and pliable to soft and gelatinous. In some cases, there are three basic components in forming a typical alginate gel: alginate, calcium salt, and a sequestrant, though some processes do not use or require a sequestrant. In this case, alginate, calcium, and the sequestering agent control the gelling system structure and the rate at which the gel forms. The grade of alginate, calcium source, and sequestering agents can be altered to produce the desired properties in the final product.

The calcium binding ability of a high-G alginate can be stronger than that of another alginate with a low proportion of G-blocks ("low-G"). A high-G hemostatic dressing may have low ion exchange (compared to a dressing with low-G alginate) between the calcium alginate and blood/wound exudates. Less ion exchange means that the calcium alginate and kaolin will stay on the dressing to a greater degree compared to a dressing with low-G alginate in which the calcium alginate converts more readily to sodium alginate which dissolves readily in blood/wound exudates. When sodium alginate dissolves, kaolin can be separated from the hemostatic device. However, in some embodiments, a high-G content may not be as desirable or may even be undesirable.

In some embodiments, alginate dressings can be used to maintain a physiologically moist microenvironment on a wound that promotes healing and the formation of granulation tissue. Certain alginates can be rinsed away with saline irrigation, so removal of the dressing does not interfere with healing granulation tissue. This can diminish the pain and damage caused by removing the bandage. Alginate dressings can be very useful for moderate to heavily exudating wounds.

In some embodiments, a method of manufacturing a hemostatic device with a hemostatic agent bound to a flexible substrate (e.g., gauze) by a cross-linked binder can be produced as follows. A binding agent, such as sodium alginate, can be dissolved in water. A hemostatic agent, such as kaolin, can be added to the alginate/water solution to form a slurry. The slurry is applied to a substrate such as a gauze or sponge. The slurry-coated substrate is then sprayed with or dipped in a calcium chloride solution, which causes the calcium to bind to the alginate, thereby sequestering the kaolin on the substrate surface and/or within the substrate. During the crosslinking step, at least some of the sodium ions are replaced by calcium ions. See Example 6 below for more information on the extent to which calcium ions replace sodium ions in at least one embodiment of the present disclosure. The duration of the crosslinking step can depend on the level of crosslinking that is desired. The substrate is then washed with water to remove some of the un-crosslinked alginate, excess calcium chloride, and sodium chloride. At least some of the unbound hemostatic agent can also be removed during a washing step.

The substrate can be subjected to a drying process that may occur before the substrate is treated in any way, immediately before the slurry is applied, after the slurry is applied to the substrate, after the crosslinked product is washed, or as a final step before or during packaging, and/or between any of these steps or after all of these steps. The drying process can be performed in many ways. In some embodiments, the drying process involves elevating the heat of the air surrounding the substrate, such as to a level that is approximately equal to or higher than the boiling point of water. In some embodiments, the drying process involves elevating the heat of the substrate itself, such as by exposing it to heated air (e.g., approximately equal to or higher than 200 degrees F.) and/or radiation, such as radio-frequency radiation, or another form of heating. In some embodiments, the drying process can include applying a vacuum or removing moisture from the air surrounding the substrate during the drying process and/or continuously replacing the air surrounding the substrate with lower-humidity air. In some embodiments, the drying process can include lyophilization or "freeze drying" of one or more components of the hemostatic device or the completed hemostatic device (e.g., including the one or more hemostatic agents and/or binders).

In some embodiments, the temperature, duration, vacuum level, and/or pressure during the drying process can be adjusted and/or monitored to produce a substantially dry hemostatic device with very low, if any, water content (e.g., less than or equal to: about 15%, about 10%, about 5%, or about 3% water by weight). In some embodiments, the drying process merely removes some amount of water such that the hemostatic device has a lower water content than when the binder and hemostatic agent were initially applied. In some embodiments, the hemostatic device is not saturated with water. The resulting hemostatic device may be sterilized and/or packaged in a sterilized container.

Without being tied to any particular theory, it is believed that the binding step is the result of the electrostatic interaction between calcium cations from the calcium chloride solution and the alginate anions. When the two ions are brought into proximity, a crosslinked compound is formed because the negatively charged alginate is electrostatically attracted to the positive calcium ions. This results in a crosslinking between alginate polymer chains through the calcium cation. This crosslinking results in the kaolin or other hemostatic agent being bound or trapped in the substrate so as to be substantially retained on or in the substrate even when exposed to water or a liquid such as blood.

Cross-links are bonds that link one polymer chain to another (e.g., by covalent bonds or ionic bonds). In some embodiments, polymers capable of crosslinking generally exhibit branches off a main chain. In the presence of a crosslinking agent, such as a calcium cation, the negatively charged branches from the same or different chains are attracted to the positive cation. The branch joining chains together is referred to as a "crosslink."

Crosslinking can produce gelation, which may occur at some point during a polymerization process. At this point, termed the "gel point," an insoluble polymer fraction is first visible. This insoluble material can be referred to as a "gel." Alternatively, the gel point refers to the point at which a system loses fluidity as measured by the inability of an air bubble to rise in it. The resulting material is insoluble in all solvents at elevated temperatures under conditions where polymer degradation does not occur.

When polymer chains are linked together by crosslinks, they may lose some of their ability to move as individual polymer chains. For example, a liquid polymer (where the chains are freely flowing) can be turned into a "solid" or "gel" by crosslinking the chains together. This description applies when an alginate such as sodium alginate is crosslinked with calcium chloride. The sodium alginate is able to be sustained in a solution, but the addition of calcium chloride causes the alginate chains to congregate or crosslink with the calcium cations, thereby forming an immobilized product. The generally immobilized product may also generally immobilize other materials that may be present such as hemostatic particles or materials and fibers or components of a substrate such as gauze. Thus, even without chemical bonds, either covalent or ionic, between the resulting immobilized product and either the hemostatic particles or the substrate fibers, the different substances or structures can be maintained tightly together. Such bonds are not required to retain the hemostatic particles in or on the substrate fibers because the alginate binder's internal crosslinking sufficiently holds these materials together.

In some embodiments, crosslinks can be formed by chemical reactions that are initiated by heat, pressure, change in pH, or radiation. For example, mixing of an unpolymerized or partially polymerized resin with specific chemicals called crosslinking reagents can result in a chemical reaction that forms crosslinks. Crosslinking can also be induced in materials that are normally thermoplastic through exposure to a radiation source, such as electron beam exposure, gamma-radiation, or UV light. For example, electron beam processing is used to crosslink the C type of cross-linked polyethylene. Other types of crosslinked polyethylene are made by addition of peroxide during extruding or by addition of a crosslinking agent (e.g., vinylsilane) and a catalyst during extruding and then performing a post-extrusion curing.

Calcium chloride, a reagent used in some of the embodiments disclosed herein, provides an example of a simple ionic bond. When calcium (Ca) and chlorine (Cl) are combined, the calcium atoms each lose two electrons, forming cations ($Ca^{2+}$), and the chlorine atoms each gain an electron to form anions (CF). These ions are then attracted to each other in a 1:2 ratio to form calcium chloride ($CaCl_2$). Other cation to anion ratios are also possible depending on the materials used. In some embodiments, cations other than calcium and anions other than alginate may be used. The use of calcium alginate as a binder in hemostatic devices of the present disclosure is just one example of a suitable material that binds a hemostatic agent to substrate or other suitable structure in part to substantially retain the hemostatic agent on the substrate when exposed to fluids such as saline and/or blood.

In some embodiments, calcium salts other than calcium chloride could be used as well as other suitable metals such as other multivalent cations. Similarly, alginates other than sodium alginate may be used such as potassium and ammonium alginates. Moreover, crosslinking could be used with materials (e.g., polysaccharides) other than alginate. In some embodiments, a material that electrostatically cross-links to form a suitable binding material for hemostatic applications can be used. In some embodiments, it may be desirable to utilize converted alginate, i.e., a substance that is primarily calcium alginate with a partial sodium content, so that at least a portion of the alginate is water-soluble.

Some methods of applying a calcium alginate or other suitable binder to a substrate include, but are not limited to, the techniques of spraying and slot die. Some methods can be used to apply a suitable binder to one or both sides of a substrate. These techniques can be adjusted to affect the extent of penetration into to the substrate material. For example, the amount of material sprayed onto a substrate can limit penetration or perfusion into the substrate. More material could be sprayed to ensure that binder and/or hemostatic material substantially permeate the substrate. Moreover, spraying could be applied to more than one side of a substrate to achieve a similar or different distribution of binder and/or hemostatic material. Similarly, a slot die technique or other methods could be modified to produce similar or different distributions of binder and/or hemostatic agent within or on a substrate. In some embodiments, a slot die technique involves applying or injecting a liquid onto or into a substrate at close range, such as when a substrate is positioned in close proximity with, or even in contact with, a structure in which there is an aperture or slot through which the liquid is dispelled onto or into the substrate. A slot-die process may utilize less liquid because it involves low or no appreciable evaporation of the liquid during application, as compared to a spraying process, and/or a slot-die process may result in low maintenance steps or expense because the liquid is substantially contained within the application system or on the product and not in the surrounding air, as with a spraying process.

Sodium alginate is a polyanionic copolymer. Calcium ions used to crosslink the alginate are anionic. However, calcium alginate (the crosslinked material) has a net negative charge. The surface charge on kaolin is negative and it has been known that the intrinsic blood clotting pathway is initiated by negatively charged surfaces. An anionic binder may not neutralize the charge on the surface of kaolin, which can affect its function as a hemostatic agent. Furthermore, calcium can act as a catalyst in the blood coagulation cascade.

Using calcium alginate to bind a hemostatic material to a substrate can be implemented by various methods including, but not limited to, immersing the substrate in the various liquids or solutions, sequentially spraying the various liquids onto the substrate, using a slot die technique, or any combination of these and other methods. Many other binders besides calcium alginate may be used instead of or used in combination with calcium alginate. Other suitable binders can include, but are not limited to, polyols such as glycerol, chitosan, and carboxymethylcellulose.

In some embodiments, virtually no crosslinking occurs either between a hemostatic agent and a crosslinked binder and/or a substrate and a crosslinked binder. Thus, the binding that results between a crosslinking binder and either a hemostatic agent or a substrate can be the result of the binder simply "trapping" one or more substances (such as one or more hemostatic agents and/or one or more portions of the substrate itself) in its immediate vicinity when crosslinking occurs, without requiring the formation of a chemical bond between the binder and such "trapped" substances.

In some embodiments, other binders capable of forming crosslinks may be used. Some suitable binders include, but are not limited to, acid soluble collagen, polysaccharides such as hyaluronan, cellulose derivatives such as carboxymethylcellulose, and polyols such as polyvinyl alcohol. In some embodiments, it may be desirable to select a binder that itself exhibits hemostatic properties. Examples of such binders include chitosan and at least some alginates particularly calcium alginate.

In embodiments in which a polyol is used, the polyol may be a glycerol (e.g., glycerin, glycerine, glyceritol, glycyl alcohol, and by its chemical name propane-1,2,3-triol, etc.). Glycerol can be a lubricious, hygroscopic, water-soluble liquid that is compatible with biological tissue. Other glycerol-based compounds can be used, including glycerol alcohols (e.g. propylene glycols), glycerol-based esterified fatty acids (e.g., glyceryl triacetates), and other materials having humectant properties and the like (as well as combinations of the foregoing). Furthermore, other polyols can be used, such as sorbitol, xylitol, maltol, combinations of the foregoing, and the like as well as polymeric polyols (e.g., polydextrose).

In some embodiments, a release agent may be used to facilitate removal of a hemostatic device from a wound. In some embodiments, the release agent is disposed on the surface or surfaces of the hemostatic device. In some embodiments, the release agent is disposed on a wound-contacting side of the hemostatic device and/or on a non-wound-contacting side. Suitable release agents include, but are not limited to, crosslinked calcium alginate, polyvinyl alcohol, glycerol, carboxymethyl cellulose, silicone, gelatinized starches, chitosan, hyaluronan, acid soluble collagen, gelatin, and the like. In some embodiments, the binder can serve as a release agent (such as in a hemostatic device comprising a low-G alginate). In some embodiments, the release agent is configured to be substantially retained on the gauze even when exposed to fluids such as blood. In some embodiments, the release agent is applied to the hemostatic material. In some embodiments, the release agent is applied to a substrate containing the hemostatic material.

Consistent with the present disclosure, a hemostatic material and a binder can be applied to any number of suitable surfaces, materials, or substrates. In some embodiments, a suitable substrate or surface comprises a mesh material comprising multiple openings or pores. In some embodiments, a suitable substrate comprises a gauze or gauze-like material comprising a porous or fibrous structure that readily absorbs liquid and/or allows liquid to pass from one side of the substrate to the other side. In some embodiments, a suitable substrate or surface comprises a sponge having applied to its surfaces or soaked within them a hemostatic agent and binder. Described below are various such embodiments involving any number of suitable substrates or surfaces. In some embodiments, kaolin is used as the hemostatic material; however, other hemostatic agents may be used in place of or in addition to kaolin. In some embodiments, calcium alginate is used as the binder; however, other binders—crosslinked or not—may be used of in place of or in addition to calcium alginate.

According to some embodiments, the amount of binder used in the device can exceed the water content of the device. Where substantial amounts of water are used to manufacture the hemostatic device, it may be necessary to subject the device to one or more drying processes. For example, a device could be heated, baked, subjected to hot air, or blow dried in order to remove at least some of the water used in one or more of the coating steps in which a hemostatic material and/or binder was applied to the device.

According to some embodiments of the present disclosure, a component that imparts a radiopaque characteristic to a hemostatic device may be used. In some embodiments, barium sulfate may be incorporated into a slurry that includes the hemostatic agent and/or binder that is applied to the hemostatic device. In some embodiments, the radiopaque component is incorporated onto one or more surfaces of a hemostatic device.

According to some embodiments, a hemostatic device comprises a pouch or other container made of permeable material. In some embodiments, a mesh material is used to form a pouch that contains a first hemostatic material in particle form. Moreover, in some embodiments, the mesh material or other suitable permeable material further comprises a second hemostatic material and binder. The binder adheres the second hemostatic material to the mesh and substantially retains it thereto even when exposed to a liquid such as blood. In this manner, both the first and second hemostatic agents are retained in and on the device and can be readily removed from a wound.

In some embodiments, the openings defined by a mesh are sized to retain a particlized hemostatic material but permit the flow of blood therethrough. In some embodiments, the size of the openings is configured to correspond to the size and shape of the particlized hemostatic material to allow at least a portion of at least some of the particlized hemostatic material to protrude through the holes while still being substantially retained in the mesh of the hemostatic device. Such a configuration can allow the hemostatic material to directly contact a wound surface and/or achieve greater contact with blood.

To apply a pouch-like hemostatic device to a bleeding wound, the device is removed from the packaging, which may comprise sterilized packaging, and placed on the bleeding wound. The first and second hemostatic materials then contact the wound and/or blood emanating from the wound. Such contact can induce clotting of the blood and/or reduce the healing time of the wound. Moreover, in some embodiments, the pouch-like hemostatic devices consistent with the present disclosure are sufficiently flexible to conform to the shape of the bleeding wound and to retain that shape upon application.

Referring now to FIG. 1, an embodiment according to the present disclosure is illustrated being applied to a bleeding wound. In some embodiments, the hemostatic device 100 is packed into the wound 120 to substantially occupy the wound. In some embodiments, a care giver uses her thumb to press a portion of the device 100 into a corner or edge of or deep into the wound 120. More material of the hemostatic device 100 is then unwound or unpacked, and the care giver pushes more of the device 100 into the wound on top of or next to the portion already pressed into the wound 120. In some cases, this process is described at "Z-folding" the material of the device 100 into the wound 120. In some embodiments, the wound 120 packed with the hemostatic device 100 is then covered or wrapped with another hemostatic device or a simple gauze. In some embodiments, the hemostatic device 100 is a hemostatic gauze according to the present disclosure. In some embodiments, the device 100 is a hemostatic sponge or pouch according to the present disclosure.

As used in this disclosure, the term "sponge" is used in accordance with its ordinary meaning in this field. In some embodiments, a sponge is a porous material that can be compressed from a first, natural or original thickness to a second, substantially smaller thickness, and that can substantially or entirely rebound after compression to its natural or original thickness. In some examples, the natural or original thickness of a sponge in the form of a sponge matrix can be substantially thicker than a bandage dressed textile such as a gauze (e.g., at least about 5 times or at least about 10 time thicker). In some examples, the natural or original thickness of a sponge matrix can be at least about one-sixth or at least about one-fifth of its width and/or length dimension. The compressed thickness can be very thin, such as about the same size as or slightly greater than a bandage dressing textile such as a gauze. In some embodiments, sponges are made of cellulose wood fibers or foamed plastic polymers. In some embodiments, the term "sponge" can refer to any absorbable material such as a gauze-type material or a foam. The features, structures, and steps described herein relating to any particular type of substrate (e.g., a sponge, a sponge matrix, a gauze, etc.) can each be applied to any other substrate described herein or otherwise.

Many different types of materials can be used to form a sponge matrix. For example, suitable polymers include one or more of polyurethanes, polyethylene foams, PHEMA foams (such as poly(2-hydroxyethyl methacrylate) hydrogel), polyacrylic acid foams, low-density polyethers, polyvinyl alcohols ("PVA"), polyhydroxybutyrate ("PHB") methyl methacrylate, poly methylmethacrylate (PMMA), and/or polyesters, etc. Some sponges can comprise double-blown polyester. Some sponges can be generally stiff after initial formation and can be reticulated (artificially broken-in by manipulation before use) to enable the sponges to closely conform to the contours of a wound. Some sponges have a high water retention ability, including some sponges with large visible pores.

As used in this disclosure, the term "foam" is used in accordance with its ordinary meaning in this field. In some embodiments, foam can include a substance that is formed by producing a numerous plurality of consecutive or adjacent large open regions in a medium in three dimensions, such as by temporarily or permanently trapping pockets of gas in a liquid or solid during formation of the foam. The trapped gas can form a coarse or irregular matrix-like structure within the sponge capable of absorbing and retaining one or more therapeutic materials such as hemostatic agents, binders, release agents, antiseptics, antibiotics, antimicrobial agents, anti-inflammatory agents, analgesics, antifungal agents, antihistamines, compounds containing silver or copper ions, combinations thereof, etc. while also being able to absorb liquids such as blood, or exudate, in some embodiments.

In some foams, the volume of gas is relatively large with thin films of liquid or solid separating the regions of gas. Some foams are known as closed-cell, and some are known as open-cell. In some embodiments of a foam comprising closed-cell foam, the gas can form a plurality of discrete pockets, each completely surrounded by the solid or liquid material. In some embodiments of a foam comprising open-cell foam, a plurality of the gas pockets can connect with each other. In some open-cell foams, liquids such as water or blood can easily flow through virtually the entire structure, displacing the air or other gas within the foam. The size of the bubbles or air pockets in a foam can vary widely. In some embodiments, the volume of air or other gas within a sponge matrix can be generally the same as or greater than the volume of foam structural material comprising the sponge matrix.

Figure 2A:
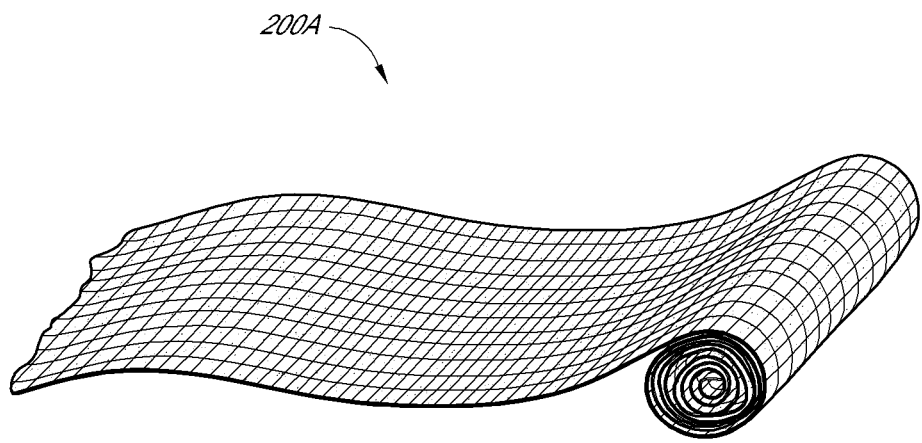
FIG. 2A is a perspective view of a roll of a hemostatic device.

Referring now to FIG. 2A, some embodiments comprise a hemostatic gauze 200A. A hemostatic material such as kaolin is coated onto a gauze substrate using any suitable method to result in the gauze 200A. One exemplary method of coating a hemostatic material onto the gauze substrate is to immerse the substrate in a hemostat/water slurry or a hemostat/water/binder slurry. Other application methods can include slot die techniques, spraying, or a combination of various methods could also be used. The hemostatic material used for the slurry in some embodiments is preferably finely ground powder such as kaolin powder, although some embodiments may also or instead employ particles, flakes, chips, beads, rods, granules, or the like.

According to some embodiments, immersion of the substrate in a slurry containing the hemostatic agent ensures that multiple outer surfaces of the substrate (e.g., a top surface and a bottom surface) are coated with the hemostatic agent. In some embodiments, immersion may also ensure that at least some hemostatic agent is embedded within the material that comprises the substrate. Similarly, other application techniques such as spraying and slot die can be used to ensure that a hemostatic agent is applied to one or more surfaces of the substrate. According to some embodiments it may even be beneficial to position the hemostatic agent primarily on or near the surface or surfaces of a substrate as compared to being located throughout the substrate. In some embodiments, it may be desirable to position the hemostatic agent primarily within the substrate as compared to on the surface of the substrate. This may be accomplished by any number of means including scraping the substrate's surface to remove exposed hemostatic agent.

According to some embodiments of the present disclosure, a hemostatic device is designed to be highly absorbent of one or more liquids such as blood, water, or exudate. In some embodiments, such as those utilizing a gauze substrate, the raw, untreated substrate is capable of absorbing at least about 3, or at least about 10, or at least about 20, times its weight in water, as compared to the initial substantially dry weight of the substrate immediately after the initial phase of manufacturing and/or drying. In some cases, a substrate can absorb at least about 12 times its weight. In some embodiments, such as those utilizing a sponge matrix, the raw untreated substrate is highly absorbent. For example, the sponge matrix may be capable of absorbing at least about 20, or at least about 40, times its weight in water, as compared to the initial substantially dry weight of the sponge substrate.

In some embodiments, the amount or weight of water that a treated gauze or a treated sponge can absorb will be different than the same gauze or sponge could absorb before being treated with a hemostatic agent. In some embodiments, the presence of one or more hemostatic agents and—in some cases—the presence of one or more binders may diminish the amount of liquid—such as water or blood—that the gauze or sponge can absorb. However, in some embodiments, the materials comprising the hemostatic agent(s), the binder(s), or both are themselves capable of absorbing liquids. Thus, although the presence of the hemostatic agent(s) and binder(s) may limit the absorption capacity of the substrate itself or sponge itself, the actual amount or weight of liquid able to be absorbed may actually be greater than the could have been absorbed by the raw, untreated gauze or sponge.

The gauze 200A is shown in FIG. 2A as a roll of gauze material. It is possible to package, ship, and sell gauze 200A in a roll form as shown. However, referring to FIG. 2B, it also possible, and in some contexts more desirable, to package a gauze in a folded configuration by "Z-folding" the material. Accordingly, a Z-fold of gauze 200B can be placed in packaging and shipped to a user. Once opened, a user or, more likely, a care giver can easily and quickly pack the gauze 200B into a wound or bleeding wound. Often, in such contexts, whether in a hospital or in the field, it is desirable to pack a wound with layers of material. In such contexts, a Z-folded gauze may be more easily applied in a layered fashion than a rolled gauze.

The gauze substrate may be any suitable woven or non-woven fibrous material including, but not limited to, cotton, silk, wool, plastic, cellulose, rayon, polyester, combinations of the foregoing, and the like. The present invention is not limited to woven or non-woven fibrous materials as the gauze substrates, however, as many other types of substrates can be used.

As used herein, the term "gauze" is used in accordance with its ordinary meaning in this field. In some embodiments, gauze includes a light, thin, open-meshed fabric of muslin or similar material used in bandages, dressings, and surgical sponges. In some embodiments, the thickness of the gauze from a top surface to a bottom surface thereof is less than or equal to about 2 mm. Some embodiments employ gauze or another substrate for internal use that can be absorbed by the body over time, without requiring removal after application and use, which may be especially useful when applied to internal organs or structures, to control bleeding, and/or absorb fluid. Some embodiments employ substrates for internal or external that is not absorbable by the body. In some embodiments, the substrate is highly absorbent, drawing liquids into the hemostatic device and/or allowing fluid to pass from a first side (e.g., a bottom surface) of the substrate through to a second side (e.g., a top surface). According to some embodiments, the gauze is a loose material characterized as porous. In some embodiments, the gauze comprises strands of material. In some embodiments, the strands are formed into a gauze prior to the application of a hemostatic material to the gauze. In some embodiments, the strands are substantially free of hemostatic material prior to being formed into a gauze. In some embodiments, the gauze strands initially exist separately from a hemostatic material before the gauze strands and the hemostatic material are combined. In some embodiments, a hemostatic material is disposed on the strands before the strands are formed into a gauze. In some embodiments, a hemostatic material is incorporated into the strands when they are formed before they are incorporated into a gauze.

According to some embodiments, the gauze material readily allows blood and other liquids to pass into and/or through the gauze. In some embodiments, the gauze is configured to readily absorb blood, which may result from the gauze being substantially porous, from the nature of the gauze material itself or from the capability of the fibers of the gauze readily absorbing liquid, and/or from the gauze having been subjected to a drying process, thereby providing the gauze with a water or moisture content lower than its saturation point and/or lower than that of a bleeding wound such that the blood and other exudate from a wound readily migrates into and/or through the gauze.

In some embodiments, more than just the gauze or substrate is configured to absorb blood. For example, a hemostatic agent may also be configured to absorb blood, and, in some case, a binder such as calcium alginate can itself be configured to absorb blood. Thus, in some embodiments, each component or at least one component of a hemostatic device is configured to absorb blood or other fluids.

Figure 2B:
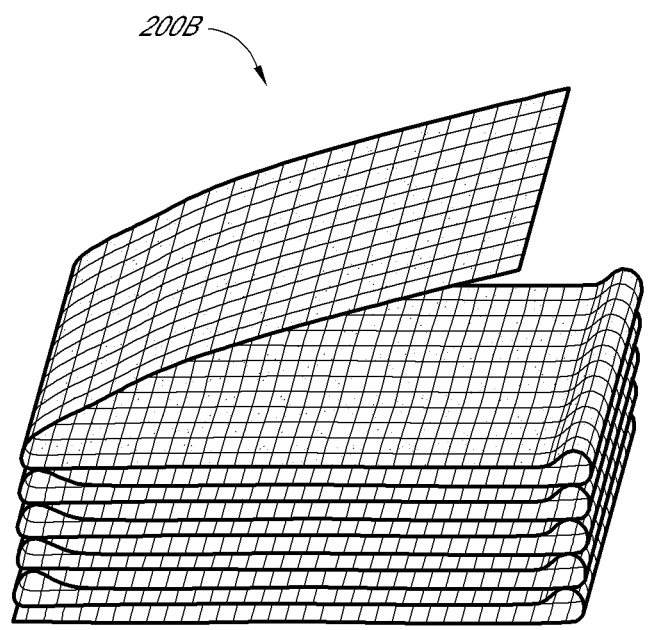
FIG. 2B is a perspective view of a hemostatic device folded in a Z-fold configuration.

In some embodiments, once a hemostatic material such as kaolin and binder are dried onto or applied to the gauze substrate to form the gauze 300A or 300B, the gauze is sufficiently flexible to allow the gauze to be folded, rolled, or otherwise manipulated for packaging as illustrated in both FIGS. 2A and 2B. The flexibility of the substrate of the gauze 200A or 200B allows the gauze to form to a shape of the bleeding wound and to retain the shape of the bleeding wound upon application. For some wounds or surgical incisions, it is very beneficial to fill the entire wound with gauze without leaving any air pockets or other open space. Thus, according to some embodiments, the treated gauze is substantially as flexible and/or as soft and compliant as untreated gauze. Even after the clay or kaolin or hemostatic agent is applied to the gauze, the treated gauze can be capable of being tightly folded, generally balled up, crumpled, and/or packed into a bleeding wound or surgical incision. A highly flexible substrate can permit the hemostatic device to be wrapped or packed tightly and closely adjacent to bleeding wounds having non-flat, irregular, and/or compliant surfaces without producing voids, puckers, gaps, and/or other regions in the treated region to help resist blood flow outside of the wound area and to resist ingress of foreign substances into the wound. Some embodiments are configured to be applied to a wound or incision using Z-folds, which is achieved by packing a layer of the gauze in the wound, then folding a second layer over the first, and continuing that with third, fourth, fifth layers, etc. until desired.

In some embodiments, a drying process may be used to achieve varying levels of water content within the gauze, the hemostatic material, or both. For example, it may be desirable to subject the gauze to an extensive drying process so as to achieve a substantially dry product having a water content of less than or equal to about 5%. It may also be desirable to achieve a water content of greater than about 5%. In some embodiments, it is desirable to achieve a water content lower than the binder content. Accordingly, the amount of drying or the particular method of drying may be modified to achieve the desired water content.

Another manner of depositing a hemostatic coating on the substrate includes applying the hemostat in slurry form, with or without a binder, on one side of a gauze substrate using a spraying technique, a slot die technique, or a combination thereof. In using any technique, the amount of slurry applied to the substrate may be limited to avoid or at least minimize or reduce the saturation of the substrate. In some embodiments, a slurry is substantially applied to only one side of the substrate and the amount of slurry applied is controlled so as to limit the migration or perfusion of the slurry through to the other side of the substrate. In some embodiments, a slurry is applied to multiple sides of the substrate and the amount of slurry applied is controlled so as to limit the migration of the slurry substantially beyond the surface or surfaces of the substrate. A colloidal form of the hemostatic material can be used to provide a stable suspension of the material with suitable viscosity for application using the slot die technique.

In some embodiments, once sprayed or applied using the slot die technique, the coated gauze substrate is then rolled or scraped to further embed a hemostatic material such as kaolin into the material of the substrate. In some embodiments, the substrate is not scraped so as to maintain at least some hemostatic material on the substrate's surface. According to some embodiments, the hemostatic material may be applied in such a way as to result in the hemostatic material being located substantially on the exterior or surface region of the substrate. In some embodiments, the hemostatic material is located throughout the substrate both on its surface and within its interior. Hemostatic material located on the surface or exterior of the substrate or hemostatic device is then able to contact blood in a wound more quickly and may further contact the wound surface itself. Direct contact with the wound surface can aid in the blood clotting process of the wound and/or in the short and long-term healing process of the wound.

Once the hemostatic material is adequately applied to the gauze substrate or other applicable substrate or device, the device or gauze is then subjected to a drying process. In some embodiments, it may be necessary to dry the device and the hemostatic material to lower its water content to a certain amount. In some embodiments, it may be necessary to achieve a water content less than about 20% or about 10% by weight. Any number of bases could be used for a water content determination including, but not limited to, the water content of just the hemostatic material, the water content of the hemostatic material and the binder combined, or even the water content of the entire hemostatic device.

According to some embodiments, a hemostatic composition is applied to a sponge. In some embodiments, a sponge comprising a foamed plastic polymer may have either an open or a closed cell configuration or a mixture of both. Some embodiments utilizing an open cell configuration are especially well suited to absorb large quantities of liquids such as blood as well as to absorb hemostatic solution applied thereto. Similar to the methods used to apply a hemostatic agent to a gauze outlined above, a sponge may also be soaked, sprayed, coated, etc. Some embodiments utilizing an open-cell configuration are capable of absorbing greater amounts of hemostatic agent than closed-cell configurations, particularly if the sponge material is squeezed or compressed and then released while subjected to a slurry of a hemostatic agent.

According to some embodiments, a binder is used in conjunction with a hemostatic agent. Suitable binders can include any of those listed herein, including crosslinked materials, some of which may also exhibit hemostatic properties. For example, in some embodiments, a sponge may be coated with a crosslinked material such as a calcium alginate either before, concurrent with, or after the application of a hemostatic agent such as a clay (e.g., kaolin). Moreover, in some embodiments, the sponge is thoroughly soaked or saturated with the binding agent while the hemostatic agent is only superficially applied to the sponge or applied to only the outer regions of the sponge. In some embodiments, particularly open cell configurations, hemostatic agents (e.g., kaolin, zeolite, etc.) can more easily penetrate into the sponge. A binder may be applied before, concurrently with, or after the application of the hemostatic agent in order to trap the hemostatic agent within the sponge or within the open cells of the foam material as it may be.

A crosslinked binder/hemostatic agent combination can be applied to a sponge in the same or a similar manner as it can be applied to a gauze. Also like a gauze, a sponge can be dried or subjected to a drying process. In some embodiments, removing at least some of the water content from the sponge by drying the sponge or subjecting it to a drying process, produces a sponge that is capable of better absorbing blood from a bleeding wound than a sponge that has not been subjected to a drying process. In some embodiments, the sponge, gauze, or other substrate is not saturated with water. In some embodiments, the device comprising the sponge, gauze, or other substrate is can permit a liquid to pass or soak through from a first outer side through the device to a second outer side, without an impermeable layer or other substantial blockage resisting the transfer of liquid through the substrate.

In some embodiments, a drying or partial drying process may comprise the application of pressure to all or a portion of the sponge so as to press out at least some of the absorbed liquid from the sponge. Various regions of a sponge may be selectively pressed to achieve one or more areas having less hemostatic agent and/or liquid present. In some cases, it may be desirable to reduce the amount of a hemostatic agent at the edges of a sponge while maintaining more of the agent toward a center region, in which case the edges are pressed to remove at least some of the hemostatic slurry.

According to some embodiments, selectively removing or reducing the amount of hemostatic agent may be beneficial to control the areas of the sponge where hemostasis is initiated and to reduce materials costs, such as when it is known that certain portions of the sponge will never or are unlikely to contact blood. Materials costs could be reduced by reusing those portions of the hemostatic slurry that are pressed out of the sponge.

Figure 3A:
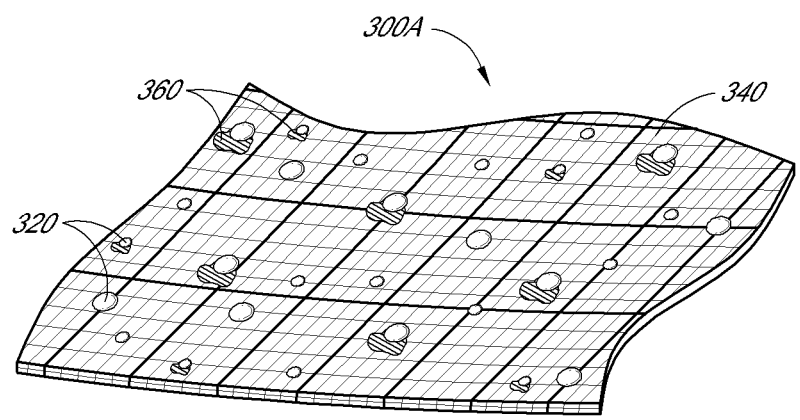
FIG. 3A is a schematic perspective view of an embodiment of a gauze having hemostatic properties.

FIG. 3A is a perspective view of a hemostatic device 300A comprising a hemostatic material 320 applied to a substrate 340. In some embodiments, the substrate 340 comprises multiple fibers in which the hemostatic material is enmeshed or bound using a binder 360. As illustrates, at least some of the hemostatic material 320 is positioned to be exposed on the surface of the substrate 340. This could be accomplished by achieving a relatively homogenous mixture of hemostatic agent and binder such that when applied to the substrate 340 at least some of the hemostatic agent 320 is exposed on the exterior of the device 300 while at least some of the hemostatic agent 320 is embedded within the binder 360 and/or within the matrix or web of fibers of the substrate 340. In some embodiments, at least some of the hemostatic agent 320 can be enmeshed in the fibers of the substrate 340 unbound by any or substantially any binder 360. When such embodiments are applied to blood or a bleeding wound, the hemostatic agent 320 may readily contact the blood to initiate the clotting process as compared to requiring the blood to soak into the hemostatic device 300 or into the fibers 340 to contact the hemostatic agent 320.

Figure 3B:
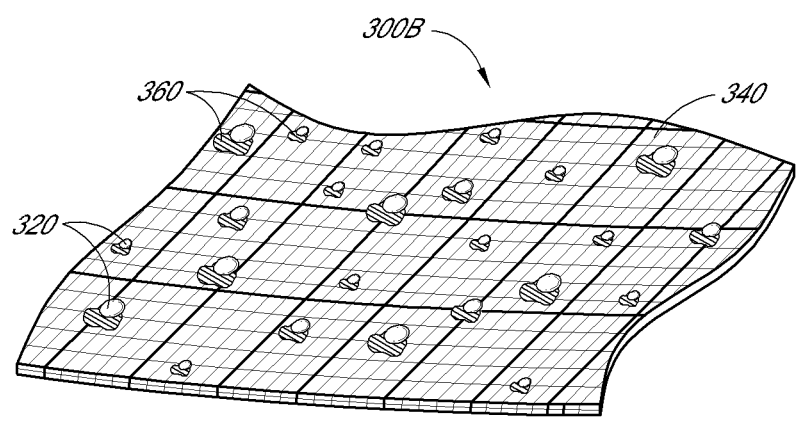
FIG. 3B is a perspective view of another embodiment of a gauze having hemostatic properties.

Referring now to FIG. 3B, an embodiment of a hemostatic device 300B is illustrated in which a hemostatic material 320 has been applied to a substrate 340 using a binder 360. In this embodiment, substantially all of the hemostatic material 320 is bound or adhered to the substrate 340 and its fibers using the binder 360. This result can be accomplished by subjecting the hemostatic device 300B to extra washing to remove any excess or unbound hemostatic material. In some embodiments, a mechanical process could be used to loosen and separate unbound hemostatic material from the hemostatic device. A hemostatic device with little or substantially no unbound hemostatic agent may be advantageous in that little or no hemostatic agent will come off the device when exposed to blood or placed in a bleeding wound.

Of course, as discussed here, the location of the binder and/or the hemostatic agent may be controlled by the methods of application as well as the extent to which those methods are used to perfuse or saturate the hemostatic device 300A. In some cases, the hemostatic material 320 is substantially distributed equally throughout the device 300A, while in some embodiments it may be desirable to limit the distribution. Selective distribution can be achieved by selectively subjecting portions of the hemostatic device 300A to pressure or other treatments to remove at least some hemostatic agent even where a hemostatic agent was first applied equally.

Figure 3C:
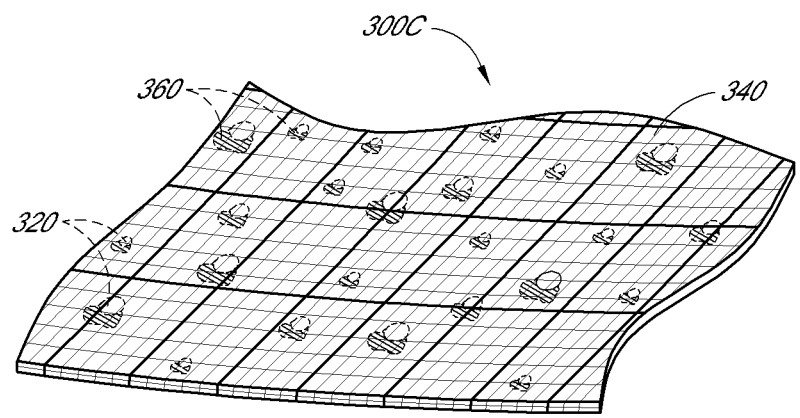
FIG. 3C is a perspective view of another embodiment of a gauze having hemostatic properties.

In some embodiments in which one or more binders are used in combination with a hemostatic agent, the position of the hemostatic agent relative to the substrate used, the binder or binders, or both the substrate and the binder may be modified depending on the desired characteristics of the hemostatic device. For example, FIG. 3C is a perspective view of a substrate such as a fibrous gauze material that comprises a hemostatic device 300C. In some embodiments, at least some portion of a hemostatic material 320 may be positioned substantially within fibers of the substrate 340 or gauze so that blood is required to first migrate through or past the surface fibers 340 and/or a binder 360 to contact the hemostatic material 320. In some embodiments, it may be desirable to maintain some separation between the clotting process and a bleeding wound, which may aid in the eventual removal of the hemostatic device 300C. In some embodiments the binder 360 may also function as a release agent. In some embodiments, as is illustrated in FIG. 3C, the hemostatic material 320 may be positioned substantially within the fibers of the substrate 340 of the hemostatic device 300A. The binder 360 may also be positioned within the fibers of the substrate 340, though in some cases at least some or virtually all of the binder 360 is positioned on the exterior of the hemostatic device 300A. Such exterior positioning may be beneficial in that it may allow the binder 360 to also act as a release agent.

Some methods for the production of a hemostatic device may comprise one or more of the steps of: providing a pre-formed gauze comprising strands; unwinding the gauze from a roll; immersing the gauze in a slurry of hemostatic material or spraying the gauze with a slurry of hemostatic material, a cross-linkable binder, and water; applying a crosslinking agent; permitting crosslinking to occur during a suitable crosslinking period; embedding the binder into the material of the gauze (which in some embodiments may itself comprise multiple steps, as described below) such as by applying pressure to the gauze by rolling the wet gauze under high pressure to incorporate the hemostatic material; rinsing the gauze with saline, water, or other liquid to remove components that are unbound and/or soluble in saline, water, or blood (or alternatively permitting the soluble components to remain on the gauze to help produce a release agent); subjecting the wet gauze to a drying process (e.g., thereby removing some or nearly all of the water content in some embodiments); removing dust from the gauze (e.g., via blasting with air knives or air nozzles, through the use of electrostatic energy, vacuuming, or brushing with direct contact brushes). Following the removal of dust from the gauze, the gauze may be wound back onto a roll, cut into sheets for individual packaging, or Z-folded, sterilized, and/or placed into sterilized packaging. Sterilization may occur after packaging the gauze. According to some methods, the binder and hemostatic agent could be applied in different steps. In some methods, the binder could be applied in multiple steps, and the hemostatic agent could be applied during one of the multiple steps or in an independent step.

Similarly, a hemostatic device comprising a sponge may comprise one or more of the steps of: providing a pre-formed sponge comprising a matrix such as a foamed polymer; immersing the sponge in a slurry of hemostatic material or spraying the sponge with a slurry of hemostatic material, a cross-linkable binder, and water; compressing the sponge while immersing it or coating it so that it can absorb more hemostatic agent and/or binder when released; applying a crosslinking agent; permitting crosslinking to occur during a suitable crosslinking period; embedding the binder into the material of the sponge (which in some embodiments may itself comprise multiple steps, as described below) such as by applying pressure to the sponge by rolling the wet sponge gauze under high pressure to incorporate the hemostatic material; rinsing the sponge with saline, water, or other liquid to remove components that are unbound and/or soluble in saline, water, or blood (or alternatively permitting the soluble components to remain on the sponge to help produce a release agent); subjecting the wet sponge to a drying process (e.g., thereby removing some or nearly all of the water content in some embodiments); removing dust from the sponge (e.g., via blasting with air knives or air nozzles, through the use of electrostatic energy, vacuuming, or brushing with direct contact brushes). Following the removal of dust from the sponge, the sponge may be folded, cut into sheets or segments for individual packaging, folded or Z-folded, sterilized, and/or placed into sterilized packaging. Sterilization may occur after packaging the sponge. According to some methods, the binder and hemostatic agent could be applied in different steps. In some methods, the binder could be applied in multiple steps, and the hemostatic agent could be applied during one of the multiple steps or in an independent step.

According to the present disclosure, some embodiments once manufactured are not substantially saturated with a liquid. The term "not substantially saturation" is used in this context to mean that the final product that is any one of devices 300A, 300B, or 300C, or any other suitable embodiment disclosed herein is capable of absorbing liquid such as blood. In some embodiments, the application of a hemostatic agent and a binder to a substrate does not saturate the substrate to the point that the substrate is unable to absorb blood from a bleeding wound. Because some embodiments are substantially soaked with slurries or solutions during fabrication, it may be necessary to subject them to a drying process. In some embodiments, the gauze or sponge is subjected to a drying process where the amount of drying depends on the desired characteristics of the hemostatic device. For example, some embodiments are dried to a greater extent to achieve a relatively low water content such as less than or about 10% water by weight relative to the hemostatic material, the hemostatic material and the binder, or the entire hemostatic device. Some embodiments are completely or partially dried to achieve a higher water content such as greater than or equal to about 10% by weight. Embodiments having a lower water content such as less than or equal to about 10% generally do not require a backing material to package or apply the device to a bleeding wound. In other words, in such embodiments, the device and its associated hemostatic agent with or without binder will not substantially smear or come off on a user's hands.

One or more variables may be adjusted to increase the amount and integrity of the hemostatic agent retained on the gauze or sponge. These variables can include, but are not limited to, slurry mixing time, slurry temperature, immersion time, the slurry agitation method, the binder used, how the binder is applied in relation to the hemostatic material, coating application technique, concentration of crosslinking agent, crosslinking time, water wash, and whether and to what extent compression is applied to a submerged substrate or sponge. The agitation may be effected by forcing air or other gas through nozzles, stirring, bubbling, boiling, or ultrasonic vibration.

The liquid used for the slurry may also be something other than water. For example, the liquid may be an aqueous ammonia solution. Aqueous ammonia has been found to induce swelling in certain fibrous materials, such as the materials typically utilized to fabricate gauze. In some methods, multiple steps are used to apply the hemostatic agent and/or the binder to the hemostatic device. For example, in some embodiments where calcium alginate is used as a binder and kaolin is used as the hemostatic material, a multi-step process can be used as disclosed herein. One multi-step process involves the use of a sodium alginate solution and a calcium chloride solution. In some embodiments, the concentration of a crosslinkable binder, such as sodium alginate in solution, is at least about 0.1% and/or less than or equal to about 2%. In some embodiments the concentration is at least about 0.25% and/or less than or equal to about 1%.

In some embodiments, the ratio of hemostatic agent (e.g., clay) to crosslinkable binder (e.g., sodium alginate) is at least about 1:2 and/or less than or equal to about 10:1. In some embodiments, this ratio is at least about 1:1 and/or less than or equal to about 8:1. In some embodiments, the calcium chloride concentration used to crosslink the alginate is at least about 1% and/or less than or equal to about 20%. In some embodiments, the calcium chloride concentration used to crosslink the alginate is at least about 3% and/or less than or equal to about 10%. In some embodiments, the crosslinking time is at least about 1 minute and/or less than or equal to about 20 minutes. In some embodiments, the crosslinking time is at least about 2 minutes and/or less than or equal to about 5 minutes.

In some embodiments, the percentage of weight gain of the finished hemostatic dressing as compared to the initial dry gauze is at least about 3% and/or less than about 34%. In some embodiments, the increased dressing weight of the resulting hemostatic device is at least about 6% and/or less than about 26%. In some embodiments, the increased dressing weight of the resulting hemostatic device is at least about 10% and/or less than about 20%.

The above method of utilizing calcium alginate to bind a hemostatic material to a gauze or a sponge can be implemented by various known methods including, but not limited to, immersing the gauze or the sponge in the various solutions, sequentially spraying the various solutions onto the gauze or the sponge, a slot die technique, or any combination of these and other methods. In some embodiments, the hemostatic agent is incorporated into a substrate directly. The hemostatic agent may be added during the substrate fabrication. If the substrate is a non-woven gauze material containing rayon and polyester, then the hemostatic agent may be incorporated into or onto the fibers of rayon and polyester. For example, a hemostatic material may be in powder form and applied to molten polyester, and polyester fibers may be drawn from the polyester/hemostatic material melt. Similarly, a hemostatic material in powder form can be applied to a sponge-forming material before or as the sponge is being made, such as to a molten polymer material that is subsequently formed into a foamed matrix or sponge, thereby incorporating the hemostatic material directly into the matrix of the sponge. If the substrate is a woven gauze (e.g., cotton), the hemostatic material in powder form may be incorporated into the cotton threads during formation of the threads.

According to some embodiments, at least some of the fibers of the substrate comprise a plurality of discrete macrocomponents or macrolayers. By way of comparison between components or layers in a fiber, one or more of these components or layers may comprise a material that has higher tensile strength, higher flexural modulus, higher durability, more consistent thickness, higher tear resistance, and/or can be reliably manufactured by way of fiber extrusion, fiber spinning, or fiber drawing, etc. Another of the one or more components or layers of a fiber may comprise a material that consists of or comprises a hemostatic or wound-healing agent. In some embodiments, the hemostatic or wound-healing agent or layer is applied or produced by a method that is different from fiber extrusion, fiber spinning, and/or fiber drawings.

In some embodiments, a multicomponent fiber can comprise two or more polymeric segments wherein at least one of the polymeric segments comprises a macromolecular host material and an additive hemostatic agent and/or a wound-healing agent. In some embodiments, the additive material can comprise a hemostatic mineral such as a molecular sieve (e.g., zeolite) or a clay. In some embodiments, the clay material is a refined clay additive material. In some embodiments, the refined clay material may comprise refined kaolin. The additive material can be coated with another material to facilitate processing, application to a wound, sterilization and/or improved binding of the one or more components of the fiber. Examples of macromolecular host materials include rayon, polyester, and even fibers of or a matrix of calcium alginate. With respect to structure of the fibrous material, the fibrous material may comprise a plurality of individual fibers at least some of which are multicomponent fibers. At least one component can contain a hemostatic agent or additive. The hemostatic additive in the fibers may be dispersed throughout the interior of the fibers and affixed to the surface of the fibers. In some embodiments, the surface may have a greater hemostatic additive loading level than the interior. The substrate may also be contained within the sterilized packaging.

Figure 4:
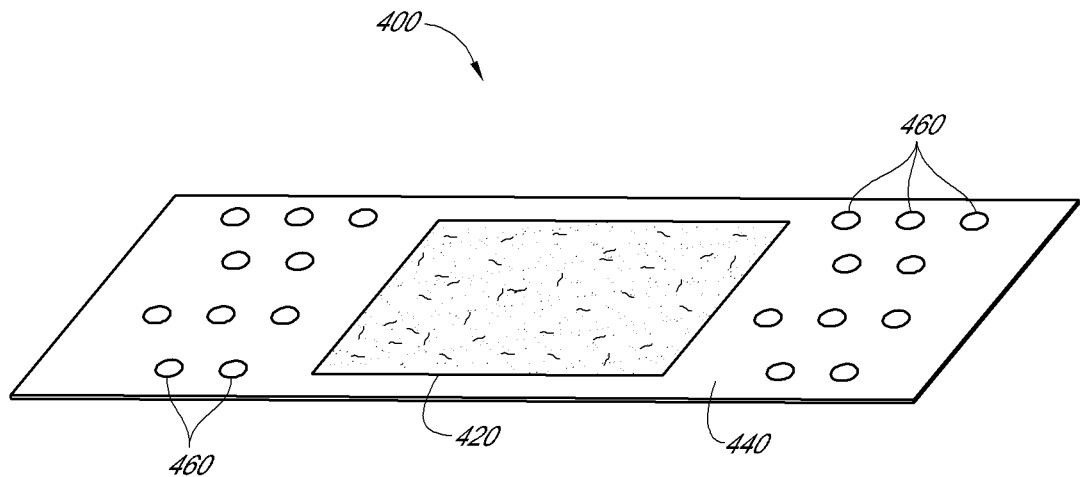
FIG. 4 is a perspective view of an adhesive bandage incorporating the hemostatic material into a gauze substrate for application to a bleeding wound.

Referring now to FIG. 4, an embodiment of a bandage is shown at 400. The bandage 400 comprises a hemostatic agent and binder applied to an absorbent substrate 420 that is mounted to a flexible substrate 440 that can be applied to a wound (for example, using a pressure-sensitive adhesive disposed over substantially all of a skin-contacting surface of the flexible substrate 440 to adhere the bandage 400 to the skin of a wearer). The absorbent substrate 420 may comprise a gauze material, a mesh material, a fibrous material, or any other suitable porous material capable of retaining a hemostatic material and a binder. The absorbent substrate 420 is stitched, glued, or otherwise mounted to the flexible substrate 440, which may be a plastic or cloth member that may include holes 460 for breathability. A release agent may be disposed over or within the absorbable substrate 420

Figure 5A:
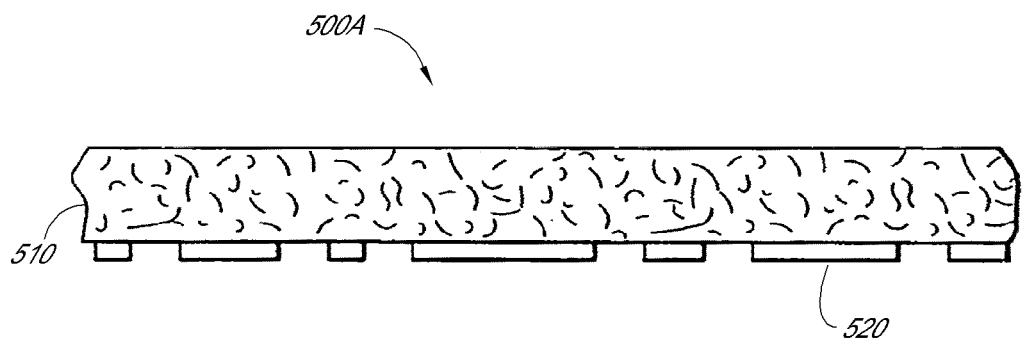
FIG. 5A is a schematic representation of a substrate having hemostatic capabilities.

FIG. 5A illustrates a sponge, shown at 500A, which comprises a substrate 520. A hemostatic agent, particlized or otherwise may be disposed on one or more surfaces of the substrate 520. In some embodiments, the hemostatic agent is disposed within the sponge 500A. In some embodiments, a release agent is disposed on one or more surfaces such as a wound-contacting surface or within the sponge 500A.

The substrate 520 is an absorbent material that defines a matrix. In some embodiments, the matrix is formed from any one of or a combination of the following: polyurethane foam, polyethylene foam, cellulose foam, PHEMA foam, polyacrylic acid foam, etc. The matrix may comprise either an open or a closed-cell configuration.

Other materials from which the substrate 520 may be fabricated include woven fabric, non-woven fabric, paper (e.g., Kraft paper and the like), and cellulose material (e.g., cotton in the forms of balls, swabs, and the like). Any material from which the substrate 520 may be fabricated may have an elastic quality. When elastic materials are used as the substrate 520, the sponge 500A becomes both a hemostatic device and a pressure bandage, particularly in embodiments in which a surface cohesive agent or mechanical fastener is added to secure the sponge in place over a wound.

In some embodiments, a release agent 540 is disposed on the substrate 510 to facilitate the easy removal of the sponge 500A from the wound tissue after the formation of blood clots. The release agent 520 may be disposed on the wound-contacting side of the substrate 510, and, in some embodiments, the release agent 540 may comprise the same material used to bind a hemostatic material to the sponge 500A. The release agent 520 may be a continuous film, or it may be discontinuous on the surface of the substrate 510. Where a release agent and binder comprise the same material, it is not necessary to separately apply any additional material to function as a release agent. In some embodiments, however, the same material may be applied in a separate step from the binder so as to form a film or separate layer on the sponge 500A.

In some embodiments, the release agent 520 may be applied to the non-wound contacting surface of the substrate 510 as a slurry of clay and release agent. In some embodiments where a polyol serves as a release agent, the concentration of the polyol is such that at least some of the alcohol component thereof seeps to the wound-contacting surface of the substrate 510 while the hemostatic material remains on or near the non-wound contacting surface.

In some embodiments where calcium alginate serves as the release agent 520, the release agent 520 is applied to either the wound-contacting side or the non-wound-contacting side of the hemostatic device. When exposed to blood or other liquid, the calcium alginate is substantially retained on the device rather than seeping further into the device or through the device and possibly into the wound. In some embodiments, the hemostatic agent may be applied to or located on either side of the hemostatic device irrespective of where the calcium alginate is located. The sponge 500A may further include water or alcohol, thereby allowing the sponge to be used as a wipe.

Figure 5B:
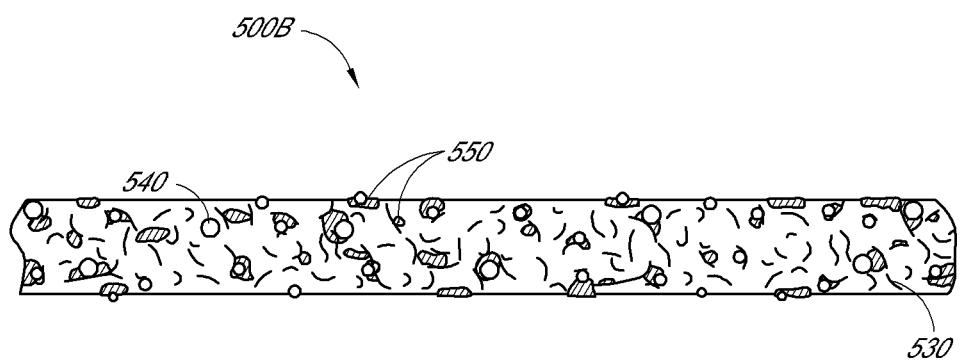
FIG. 5B is a schematic representation of another substrate having hemostatic capabilities.

Referring now to FIG. 5B, an embodiment of a sponge 500B is illustrated in which the substrate of the sponge 500B resembles woven or non-woven fibers 530. In some embodiments, a sponge comprises a thick matrix 530 such as a foamed polymer or other suitable foam material. Enmeshed within and/or bound to the fibers/matrix 530 is a hemostatic material 540 that may be in particle or powder form within and on the fibers/matrix 530. To help retain the hemostatic material 540 within and on the fibers/matrix 530, a binder 550 is used. Suitable binders include calcium alginate and other binders disclosed herein. FIG. 5B illustrates that at least some of the hemostatic material is exposed on the surface. This positioning allows at least a portion of the hemostatic material 540 to directly contact at least a portion of blood from a wound to facilitate in the clotting of the blood and healing of the wound. The sponge 500B is configured to absorb liquids such as blood. Thus, in some embodiments, the fibers/matrix 530 are not packed tightly together, and the binder 550 does not saturate the matrix that the fibers 530 define. This ensures that the sponge 500B remains porous.

Figure 5C:
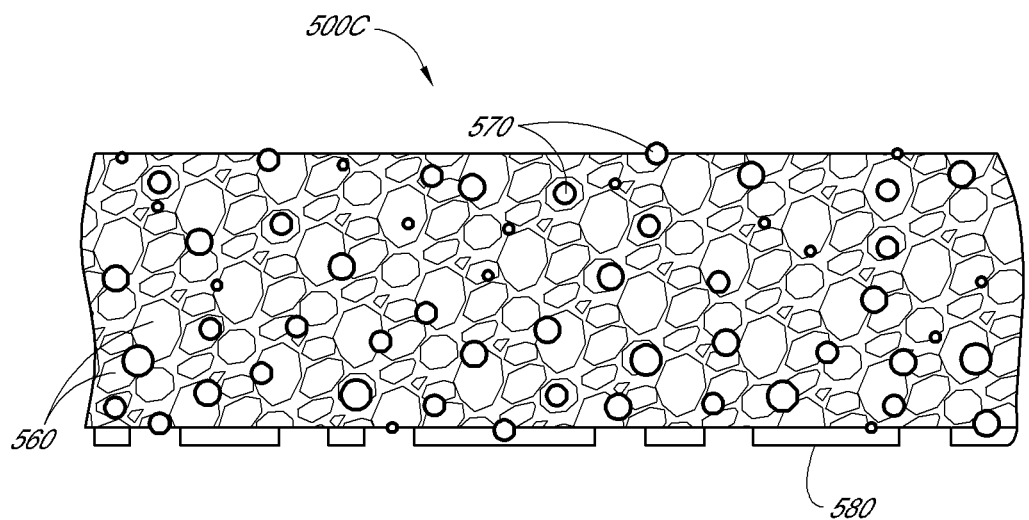
FIG. 5C is a schematic representation of an embodiment of a sponge matrix having hemostatic capabilities.

Referring now to FIG. 5C, an embodiment of a sponge 500C is illustrated in which the void spaces 560 characteristic of a sponge material or a foamed polymer is more visually apparent. In some embodiments, the void spaces 560 takes on an open or closed-cell configuration depending on the nature of the materials used as well as the desired features of the sponge 500C. In some embodiments, the open or closed-cell configuration may be referred to as a matrix. FIG. 5C also illustrates a hemostatic material 570 distributed generally evenly and/or generally completely throughout the void spaces 560. In some embodiments, at least some of the hemostatic material 570 is located on at least one of the top and bottom surfaces of the sponge 500C. In some embodiments, a release agent 580 is also applied to at least one surface of the sponge 500C, preferably a wound-contacting surface.

While the embodiment illustrated in FIG. 5C includes a hemostat material 570 distributed throughout the matrix of the sponge 500C as well as on both a top and bottom surface of the sponge 500C, some embodiments can achieve different distributions of the hemostatic material. For example, in some embodiments, a sponge with a hemostatic agent or material already applied can be subjected to a treatment or process to remove at least some of the hemostatic material. In some embodiments, an uneven distribution of the material can be achieved during the application process, such as where a spraying process is used and only a portion of the sponge substrate is subjected to the spray.

Disclosed herein are multiple methods of manufacturing a hemostatic device. Generally, these methods results in a hemostatic material bound to or contained within a substrate or porous material. Also disclosed herein are multiple methods of treating a bleeding wound. Generally, these methods involve the application of a hemostatic device directly to a wound surface to achieve direct contact with the wound surface and/or the blood emanating from the wound. Also disclosed is the ability to maintain a hemostatic material on or in the hemostatic device during the application to the wound and/or when the device is removed from the wound.

According to some embodiments, a method of manufacturing a hemostatic device comprises the application of a slurry of a hemostatic material and a binding material to a suitable substrate. In some embodiments, a suitable substrate is a gauze material or a porous substrate such as a sponge material that readily allows for blood or other liquids to flow through or be absorbed into the substrate. According to some embodiments, the application of a slurry or a solution to a substrate involves the application of multiple compositions possibly in multiple and distinct application steps. In some embodiments, the application of a slurry involves the application of a first material mixed with the hemostatic agent and the application of a second material in solution that interacts with the first material to bind the hemostatic material to the substrate. In some embodiments, a substrate is washed with water, deionized water, and/or saline after the application of either the second or first materials or after both. In some embodiments, a substrate that has been subjected to a slurry or a solution of hemostatic agent and binding material is also subjected to a drying process where the quantity of water in the device is reduced to a desired water content. In some embodiments, the substrate is subjected to a drying process after a slurry is applied, after a second material in solution is applied and washed, or both. In some embodiments, the desired water content is at least about 3% by weight. In some embodiments, the desired water content is less than or equal to about 20% by weight.

According to some embodiments, the application of a slurry and/or a material in solution to a substrate is achieved by immersing the substrate in the slurry and/or solution. In some embodiments, the application is achieved by spraying the various materials onto one or more surfaces of a substrate. In some embodiments, a slot die technique is used to apply various materials to a substrate. In some embodiments, a combination of application methods is used in a multi-step application. According to some embodiments, the gauze or hemostatic device undergoes further processing prior to packaging. In some embodiments, further processing includes scraping of the exterior surface or surfaces, compression of the gauze or device to compact it or press into the hemostatic agent and binder materials, and/or the addition of further components such antibacterial agents, antimicrobial agents, antiseptics, etc.

Figure 6:
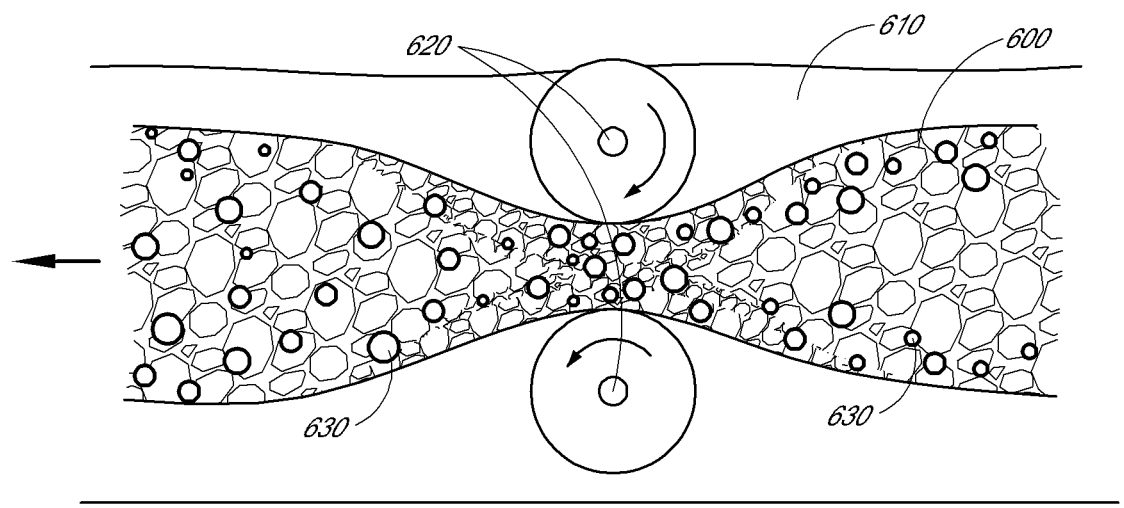
FIG. 6 illustrates an example of an application process for applying a slurry containing a hemostatic agent to a sponge substrate.

An example of a method of application is illustrated in FIG. 6, in which a portion of a substrate, in this case a sponge substrate 600, is immersed or submerged in a slurry 610 containing a hemostatic agent. In some embodiments, the substrate is fully immersed, and in some embodiments only a portion is immersed. FIG. 6 illustrates that, in addition to being submerged, the substrate 600 can be compressed, such as by using rollers 620. The substrate 600 is compressed between the rollers 620 while submerged in the slurry 610 so that the subsequent expansion of the substrate 600 draws the slurry 610 further into the matrix comprising the substrate 600. This or a similar process has the capability of achieving a high quantity of hemostatic material (much higher than without compression) within the sponge 600 because the slurry 610 is able to penetrate deeper into the substrate 600 after the rollers 620 have removed air from void space that would otherwise have limited the penetration of the slurry 610, thus producing a temporary vacuum effect within the sponge.

An example of this compression effect is illustrate in FIG. 6 in which hemostatic particles 630 are seen within the sponge substrate 600 prior to being compressed by the rollers 610 but not thoroughly distributed throughout the substrate 600. It can be seen that with the expansion of the sponge substrate 600 subsequent to compression between the rollers 620, the slurry 610 and the particles 630 are able to penetrate deeply into the interior region of the substrate 600 to achieve a thorough and uniform distribution of slurry 610 within and/or throughout the substrate.

In some embodiments, only a single roller is necessary to achieve a desired level of compression. In some embodiments, less than maximum compression is used to achieve only a partial penetration of the slurry and, therefore, the hemostatic material. In some embodiments, submersion time is also controlled either in conjunction with a compression step to control the level or depth of penetration within the substrate. In some embodiments, a substrate such as a sponge or a gauze is compressed while subjected to an application method other than or in addition to immersion such as spraying or a slot die technique.

According to some embodiments of the present disclosure, a method of treating a bleeding wound comprises the application of a hemostatic device to the wound such that the device directly contacts the blood emanating from the wound and/or the surface of the wound itself to accelerate hemostasis. In some embodiments, a method of treating a bleeding wound comprises the application of a substrate coated with or containing therein a hemostatic material bound to the substrate with a binder. In some embodiments, the hemostatic material is a clay material, and in some embodiments, the binder is a cross-linked material such as a cross-linked alginate. In some embodiments, a bleeding wound is treated by applying hemostatic gauze directly to the wound where the gauze comprises kaolin bound to the gauze with calcium alginate. In some embodiments, the calcium alginate substantially retains the kaolin on or in the gauze during application of the gauze to the wound, while blood from the wound interacts with the gauze, and/or when the gauze is removed from the wound.

In some embodiments, a bleeding wound is treated by applying a hemostatic sponge directly to the bleeding surface of the wound where the sponge comprises a hemostatic agent such as clay (e.g., kaolin) that is bound to or within the sponge with a binder, such as a cross-linking binder (e.g., calcium alginate). In some embodiments, the binder substantially retains the hemostatic agent on or in the sponge during application of the sponge directly to blood emanating from the wound, while a substantial amount of blood from the wound is drawn into the sponge (e.g., in a volume corresponding to the values or ranges of water absorption capability of sponges as described herein) so that the blood can interact with the hemostatic agent within or on the sponge. The sponge can be removed from the wound following hemostatis.

In some embodiments, a method of treating a bleeding wound comprises the application of a gauze containing kaolin and later removing the gauze from the wound while also minimizing or appreciably diminishing the release of hemostatic agent from the gauze. In some embodiments, the gauze is removed when the bleeding has stopped or when the bleeding has been reduced or substantially reduced. In some embodiments, the gauze or hemostatic device is first removed from sterilized packaging before application to a wound.

In some embodiments, a method of treating a bleeding wound comprises the application of a sponge containing clay (e.g., kaolin) and later removing the sponge from the wound while also retaining substantially all of the hemostatic agent on the sponge (e.g., minimizing or appreciably diminishing the release of hemostatic agent from the sponge). In some embodiments, the sponge is removed when the bleeding has stopped or when the bleeding has been reduced or substantially reduced. In some embodiments, the sponge is first removed from sterilized packaging before application to a wound.

According to some embodiments, a method of treating a wound comprises the application or repeated application of a hemostatic dressing. In some embodiments, a hemostatic device comprising kaolin and calcium alginate bound to a gauze dressing or a sponge is applied to a wound once or for as many times as needed and for whatever duration is required to reduce the healing time of the wound. In some embodiments, a wound may still be bleeding or may still contain exudate when a hemostatic device is applied. In such instances, it is believed that application of a hemostatic device according to the present disclosure aids in wound healing by removing the exudate or blood and/or helping the blood to clot. In some embodiments, a method of reducing the healing time of a wound further comprises removal of scabs or cellular formations from the wound between one or more applications of a hemostatic device to the wound surface. In some embodiments, a hemostatic device according to the present disclosure is applied to a wound for a duration of about one hour and the removed. In some cases, a hemostatic device is again applied immediately or after a period of time. In some cases, a hemostatic device is applied for a duration of at least about 24 hours before being removed and a clean hemostatic device being put in its place.

Example 1—Acceleration of Clot Time and Retention of Hemostatic Materials

The table below shows the compositions and clot test data for some examples of hemostatic dressings made according to the present disclosure. As in some embodiments disclosed herein, the dressings of this experiment contain a high-G alginate. This alginate is comprised of about 68% G and about 32% M monomers. (For more information on some methods of determining the composition of an alginate sample, see Example 3 below).

| 1 Sample | 2 Na Alg. (SA) % | 3 Kaolin:SA Ratio in Slurry (x:1) | 4 CaCl$_2$ % | 5 Cross-link Time (minutes) | 6 Final Weight Gain (%) | 7 Clot Time (seconds) |
|---|---|---|---|---|---|---|
| 1 | 1 | 2 | 5 | 2 | 15.8 | 143 |
| 2 | 1 | 2 | 5 | 10 | 16.07 | 147 |

-continued

| 1 Sample | 2 Na Alg. (SA) % | 3 Kaolin:SA Ratio in Slurry (x:1) | 4 CaCl$_2$ % | 5 Cross-link Time (minutes) | 6 Final Weight Gain (%) | 7 Clot Time (seconds) |
|---|---|---|---|---|---|---|
| 3 | 1 | 2 | 5 | 2 | 19.61 | 119 |
| 4 | 0.8 | 2 | 5 | 2 | 19.37 | 117 |
| 5 | 1.5 | 1 | 5 | 2 | 18.76 | 117 |
| 6 | 0.5 | 1 | 5 | 2 | 3.92 | 117 |
| 7 | 0.5 | 3 | 5 | 2 | 11.10 | 117 |
| 8 | 0.6 | 1 | 5 | 2 | 5.29 | 132 |
| 9 | 0.6 | 3 | 5 | 2 | 14.47 | 117 |
| 10 | 0.7 | 1 | 5 | 2 | 5.9 | 129 |
| 11 | 0.7 | 2 | 5 | 2 | 12.81 | 114 |

Explanation of Column Headings:
Column 2: concentration of sodium alginate in water prior to the introduction of kaolin.
Column 3: ratio of kaolin to sodium alginate in the slurry prior to the introduction of a gauze substrate.
Column 4: concentration of calcium chloride in solution with water that is used to crosslink the sodium alginate and kaolin on and in the gauze substrate.
Column 5: the amount of time in minutes that the gauze substrate was exposed to the calcium chloride solution.
Column 6: the percentage weight gain of each sample. These values were obtained by weighing each sample first as a dry, untreated gauze substrate and then after the kaolin/alginate mixture had been applied, cross-linked, washed, and the resulting product had been subjected to a drying process.
Column 7: the in-vitro clot time according to the Lee-White method.

This example illustrates the reduced clot time achieved using a cross-linked binder such as alginate. Other methods may also or alternatively be used to demonstrate or determine clot time or another characteristic of a hemostatic device. As shown, in some embodiments, the average in-vitro clot time under standardized testing using a hemostatic device made in accordance with some embodiments as described herein can be less than or equal to about 150 seconds or less than or equal to about 130 seconds or less than or equal to about 120 seconds.

Example 2—One Form of Measurement of Hemostatic Material Released from a Hemostatic Device In this example, the amount of hemostatic agent released from a hemostatic device that has been prepared according to the present disclosure was measured; however, other examples, tests, or methods may also or alternatively be used to make this or a similar determination. As in some embodiments, a dressing was prepared using a hemostatic agent (kaolin). Specifically, the dressing for this experiment was prepared according to the present disclosure. This measurement comprised the following steps:
A piece of dressing was immersed in saline (0.90% w/v of NaCl) and shaken periodically for 24 hours.
The saline/solids suspension was then filtered using a 0.2 micron Nylon filter to capture all the solids.
The filter was analyzed using the Proton Induced X-ray Emission (PIXE) method to determine the amount of Si and Al present.
The quantity of kaolin on the filter was calculated from the measured Si and Al determined in the previous step.

Preliminary analysis on prototypes showed that 0.15 mg of hemostatic agent per 1 square inch of dressing was released and detected by this method. The amount of released hemostatic agent was 4.5% of the total hemostatic agent on the dressing prior to the test. This is a significant reduction of hemostatic agent released when compared to a dressing which uses a saline-soluble material to bind the hemostatic agent to the dressing (in which a majority of hemostatic agent will be released by this method). Such saline-soluble materials may include alginates having a low-G content, meaning a ratio of G to M that may be less than 1:1.

Example 3—One Form of Determination of the Relative Amounts of G and M Monomers in an Alginate Sample—Using—$^1$H NMR Spectroscopy An analysis to determine the relative amounts of guluronate and mannuronate monomers using High temperature $^1$H NMR was conducted on two samples of calcium alginate (Alginate A and Alginate B). It should be noted that methods other than those described below can be used to determine the relative or absolute amounts of guluronate and mannuronate in an alginate sample. The relative amounts of guluronate and mannuronate in the sodium alginate samples are shown in the table below.

| Source | Composition Fractions | | Doublet Frequencies | | | | M/G |
|---|---|---|---|---|---|---|---|
| | $F_M$ | $F_G$ | $F_{MM}$ | $F_{MG}$ | $F_{GM}$ | $F_{GG}$ | |
| Alginate A | 0.32 | 0.68 | 0.21 | 0.11 | 0.16 | 0.52 | 0.47 |
| Alginate B | 0.34 | 0.66 | 0.20 | 0.13 | 0.12 | 0.55 | 0.52 |

Experimental Methods

The experimental conditions were obtained from Thomas A. Davis et al., *$^1$H-NMR Study of Na Alginates Extracted from Sargassum spp. in Relation to Metal Biosorption,* 110 Applied Biochemistry and Biotechnology 75 (2003). The samples were dissolved in $D_2O$ and dried several times prior to the NMR data acquisition. For the Alginate A sample, the NMR experiments were performed using the VT unit at 70° C. and 90° C. employing the Bruker Avance 500 FT-NMR spectrometer equipped with a 5 mm BBOF probe. For the Alginate B sample, values were obtained only at 90° C. Quantitative $^1$H NMR data without the use of the decoupler was acquired using an 80° C. pulse and a 5 second relaxation delay. Sodium 3-trimethylsilylpropionate-2, 2, 3, 3, d4 was used as an internal reference. The chemical shift scale was referenced to the solvent peak.

Figure 7:
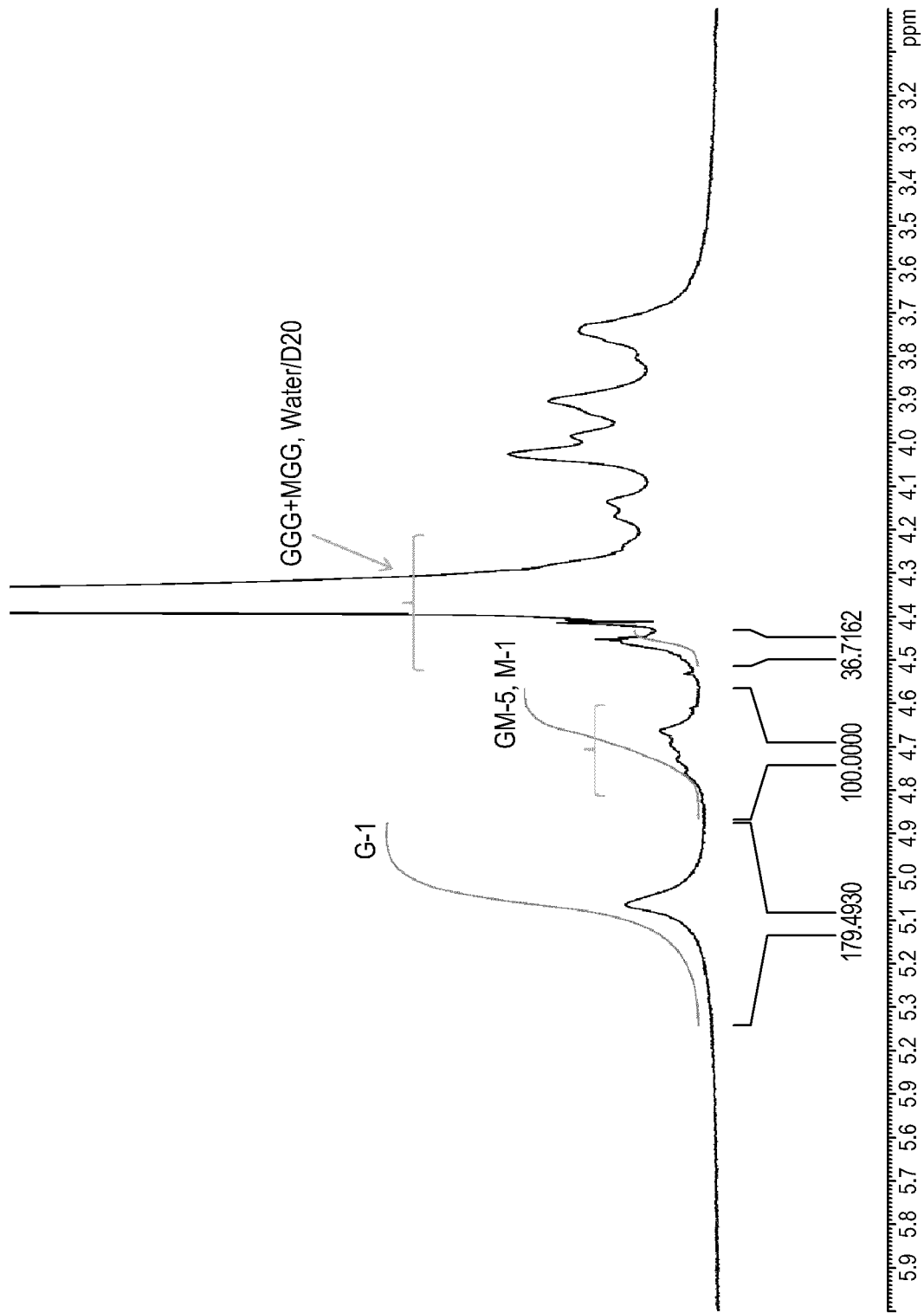
FIG. 7 is a compositional analysis of an alginate sample using $^1$H-NMR.
Figure 8:
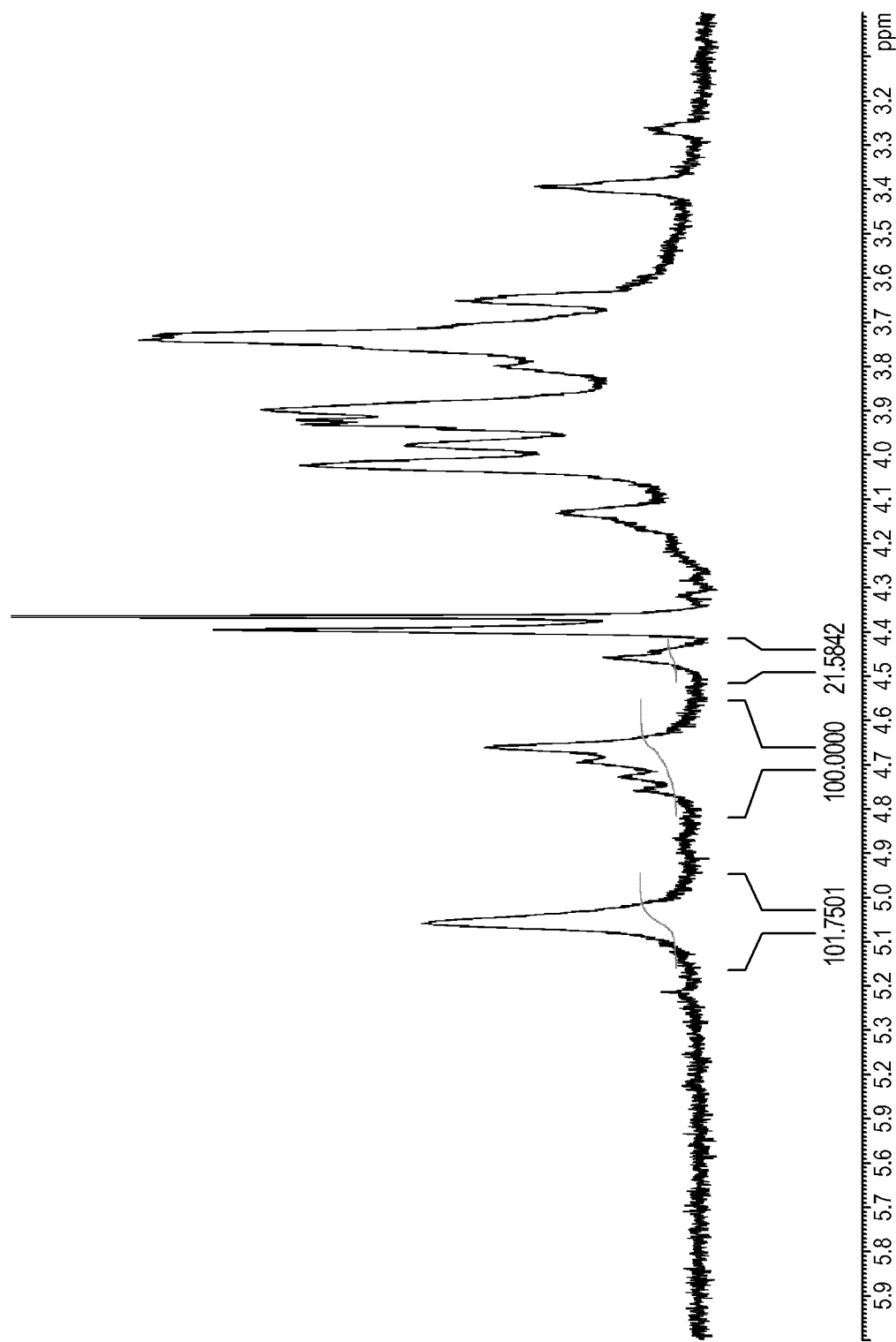
FIG. 8 is another compositional analysis of an alginate sample using $^1$H-NMR.
Figure 9:
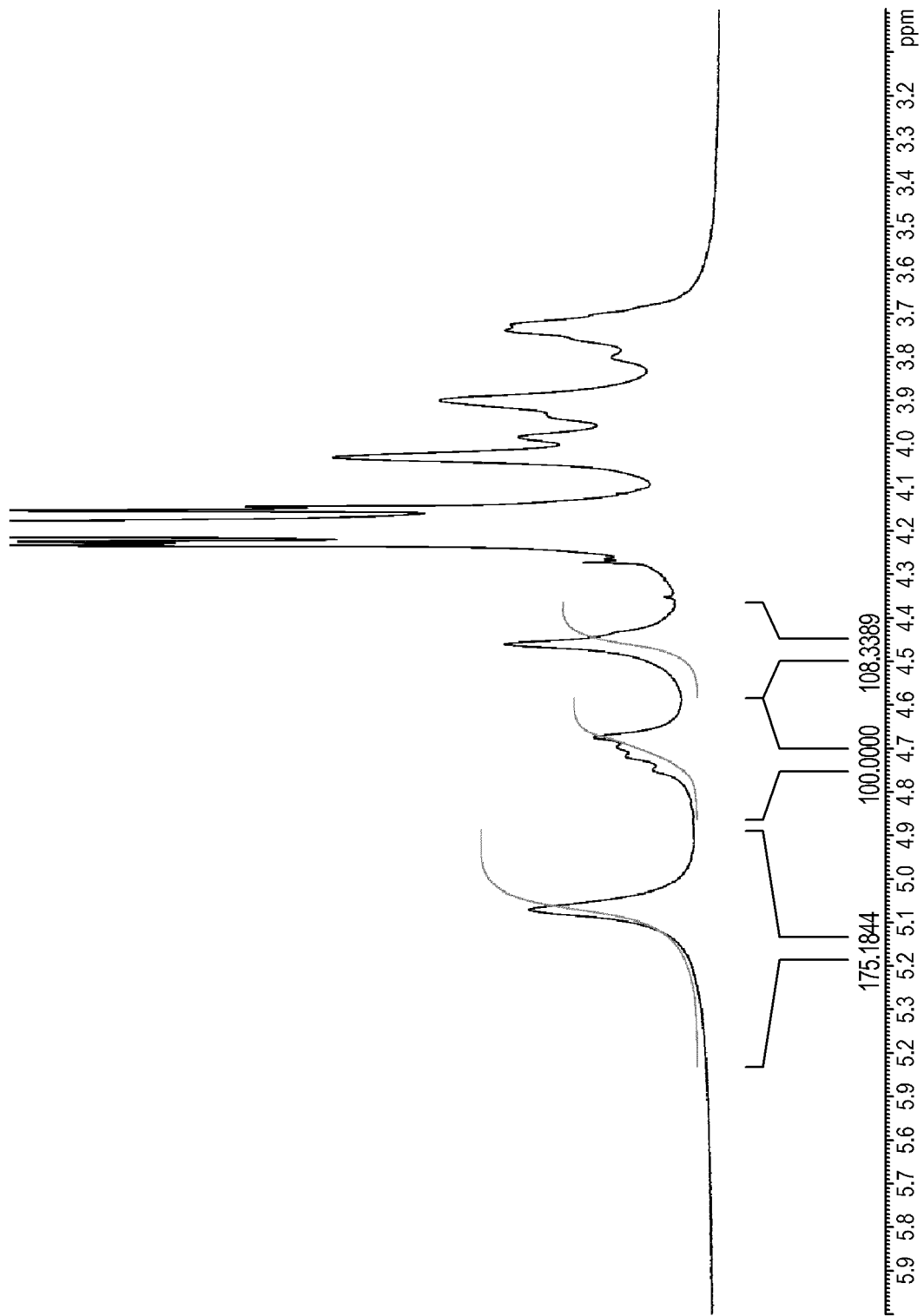
FIG. 9 is another compositional analysis of an alginate sample using $^1$H-NMR.
Figure 10:
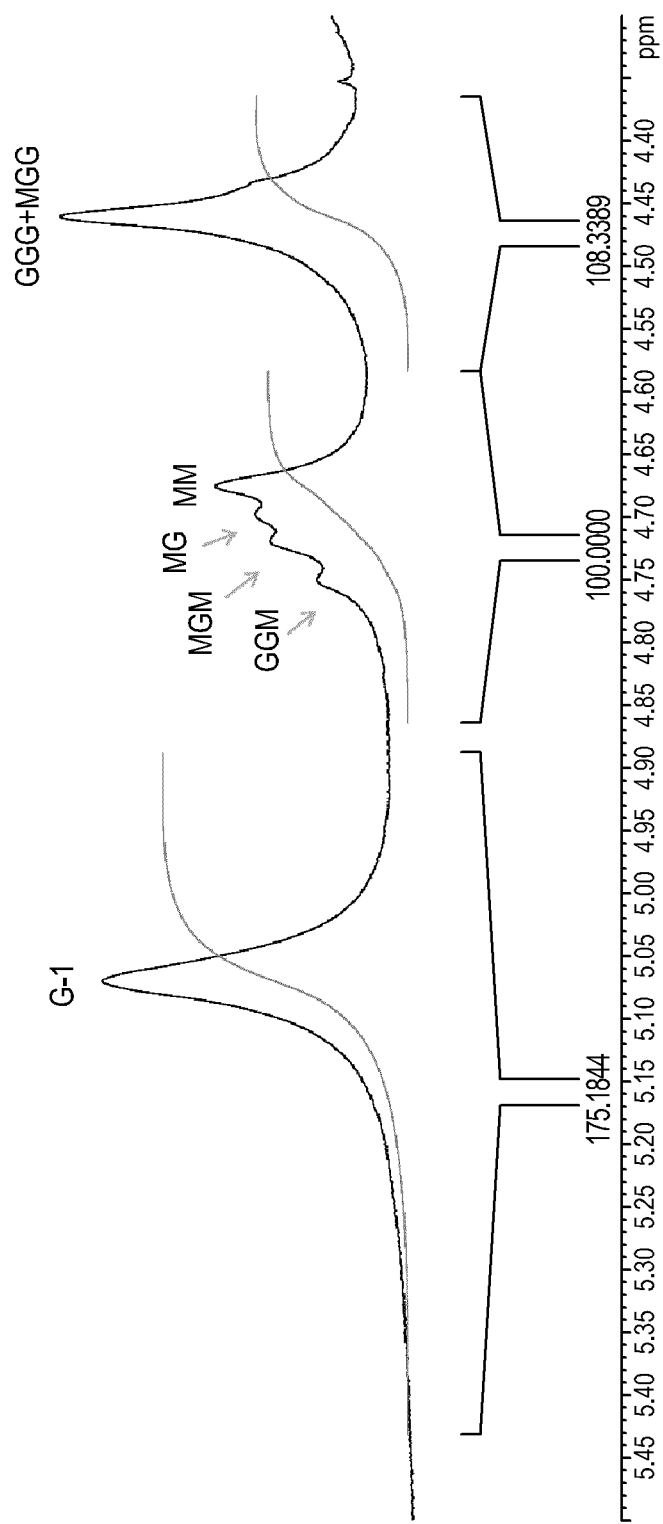
FIG. 10 illustrates a portion of the analysis shown in FIG. 9.
Figure 11:
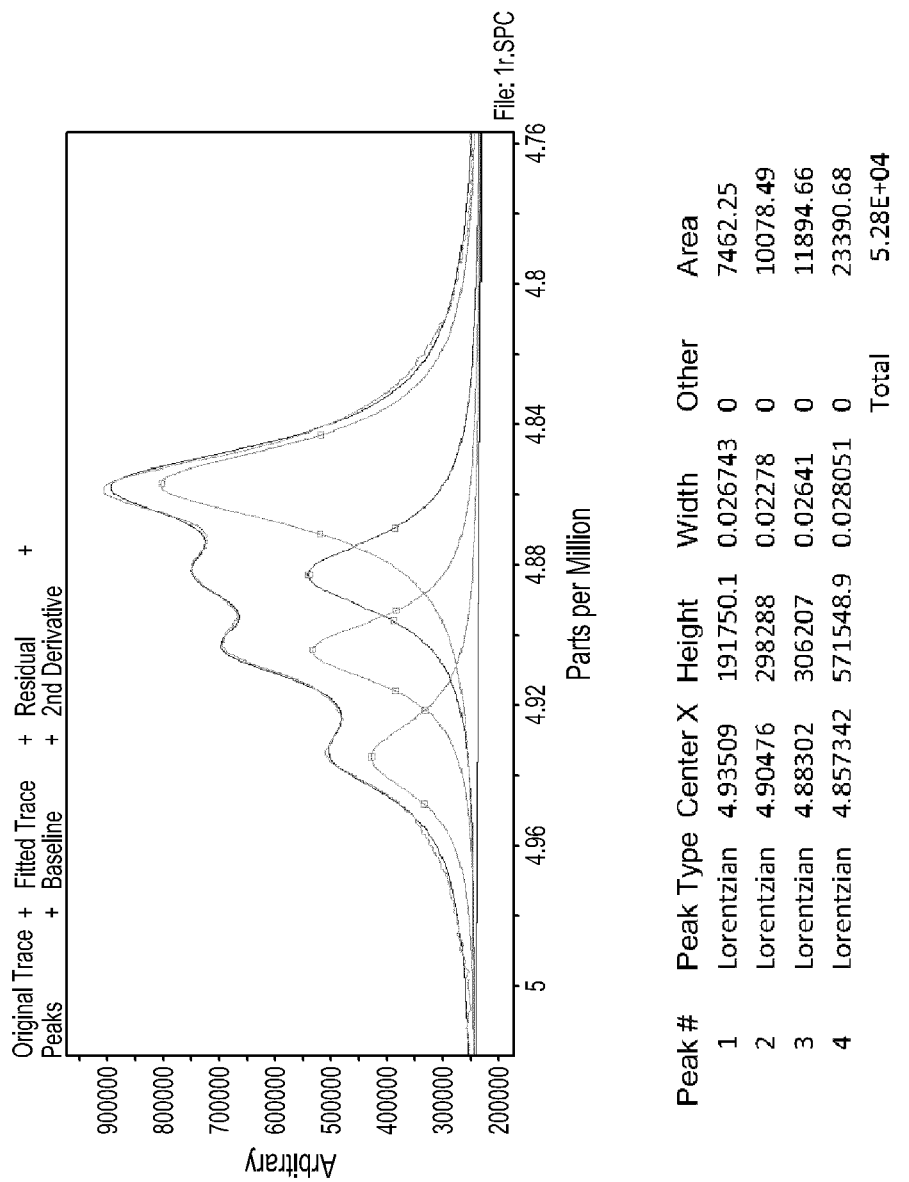
FIG. 11 is peak-fitting data for the analysis shown in FIG. 9.
Figure 12:
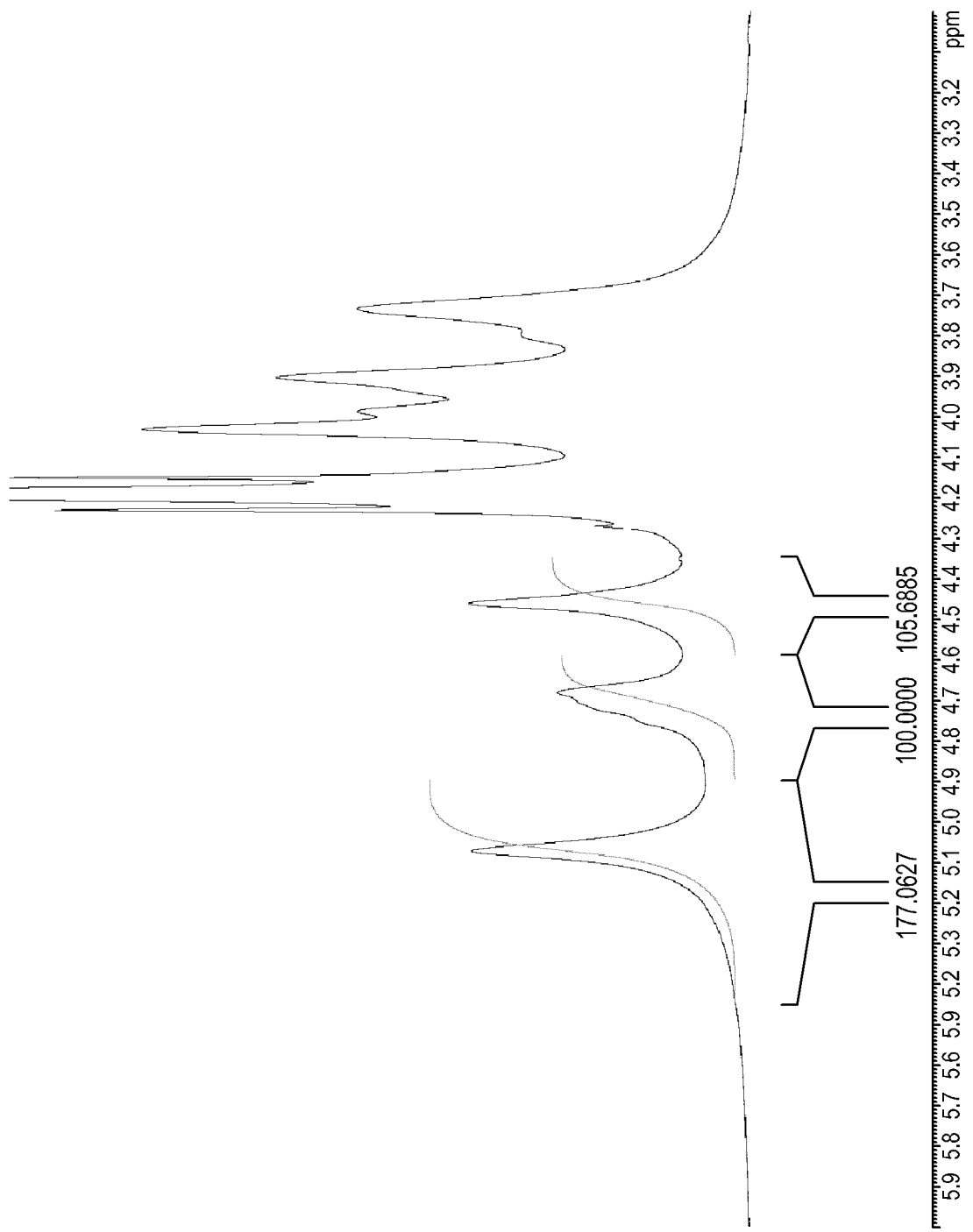
FIG. 12 is another compositional analysis of an alginate sample using $^1$H-NMR.
Figure 13:
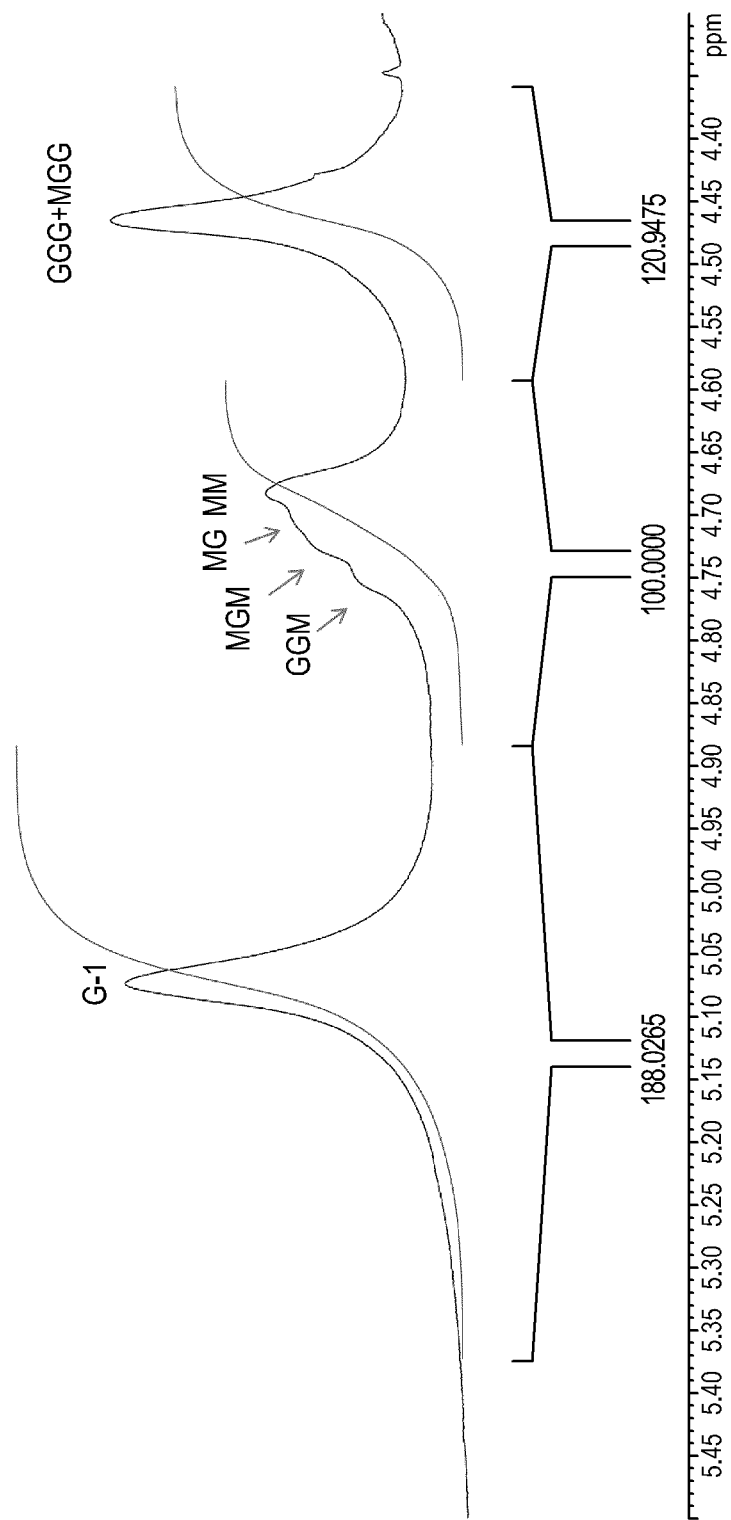
FIG. 13 is another compositional analysis of a second alginate sample using $^1$H-NMR.
Figure 14:
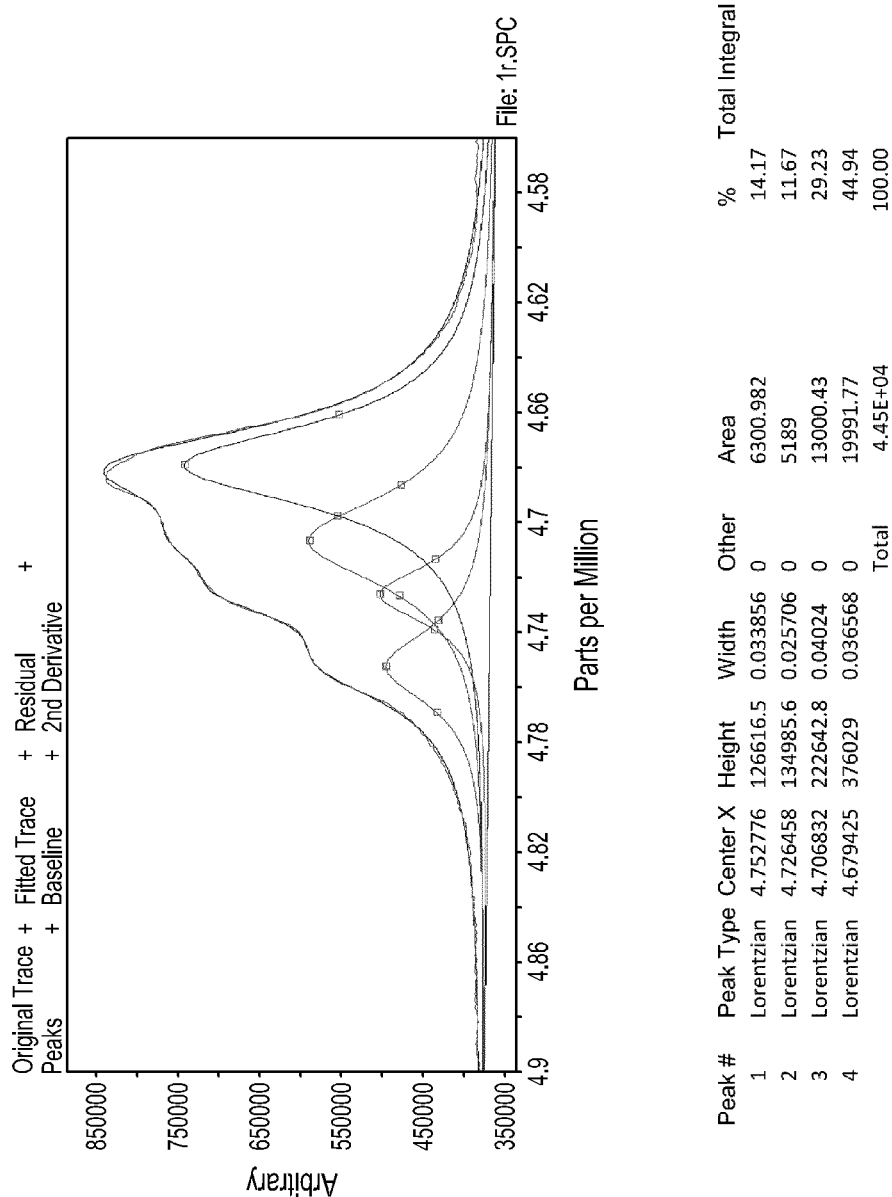
FIG. 14 is peak-fitting data for the analysis shown in FIG. 13.

The relative amounts of guluronate and mannuronate were based on $^1$H NMR data acquired at 70° C. using the decoupler to suppress the solvent peak which was overlapping with the GGG+MGG peak. It is believed that the use of the decoupler did not affect the integration of the peaks of interest; however, the results of this example did show a difference in the integral values in the $^1$H NMR data acquired at 70° C. without the decoupler as compared to the $^1$H NMR data acquired at 70° C. with the decoupler. The spectrum in FIG. 7 was acquired at 70° C. without decoupling and shows, as noted in the article, the peaks of interest and specifically the overlapping GGG+MGG and solvent/water peaks. The spectrum in FIG. 8 was acquired at 70° C. using the decoupler and shows the solvent/water peak has somewhat shifted, but also shows the integral values are not the same as the integral values obtained in the experiment without the use of the decoupler. The reference article also noted that additional experiments were performed at 90° C. without decoupling which resulted in shifting the solvent/water peak further upfield and away from the peaks of interest without affecting the integrity of the sample. So additional experiments were performed at 90° C. without decoupling, and the results were consistent with the reference article's results. To further confirm these results, a new sample solution was prepared using the same conditions as the first prepared solution and similar results were obtained similar. The spectra in FIGS. 8-9 were acquired on the first sample solution at 90° C. without decoupling, and FIG. 12 was acquired on a second sample solution using the same parameters. Since it was necessary to have quantitative results in order to calculate the relative amounts of guluronate and mannuronate in the sodium alginate sample and the data for the experiments performed at 70° C. were not consistent with the data shown in the reference article, the results shown in the table above are based on the data acquired at 90° C. without decoupling. FIG. 11 shows the peak fitting data for the spectra shown in FIGS. 9-10. The spectrum in FIG. 13 was acquired from the Alginate B sample at 90° C. without decoupling, and FIG. 14 illustrates peak fitting data for the same sample. The compositional values shown in the table above for Alginate A alginate are derived from the peak fitting data illustrated in FIG. 11. Similarly, the compositional values shown for Alginate B are derived from the peak-fitting data illustrated in FIG. 14.

Example 4—One Form of Determining the Relative Amounts of G and M Monomers in Alginate Using Dry Weight The following test was performed on various samples of hemostatic dressings prepared according to some embodiments of the present disclosure. As in some of the embodiments disclosed herein, the dressings of this example have an alginate binder. The purpose of this example was to determine whether the alginate used in any particular embodiment is a high-G or a low-G alginate; however, other experiments, tests, or methods may also be employed to make this or a similar determination. The premise of this experiment is that in some embodiments a high-G alginate will generally dissolve in a saline solution to a lesser extent than some embodiments having a low-G alginate such that a high-G dressing generally exhibits a greater dry weight than a low-G dressing after having been soaked in a saline solution. Accordingly, the following steps were applied to each sample:
(1) A sample of each dressing was cut from the dressing.
(2) The samples were dried at about 90° C. for about 10 minutes to substantially drive off moisture.
(3) The samples were weighed immediately after drying (before the dressing could absorb ambient moisture).
(4) Each sample was soaked for 24 hours in a tube containing 12 milliliters of saline. While soaking, each tube was shaken vigorously three times within the 24-hour period.
(5) The samples were then removed from the tubes, and excess saline was gently squeezed back into the tubes.
(6) The samples were dried at approximately 90° C. for 30 minutes.
(7) After the drying process, each sample was weighed again.

| Sample Type | Sample No. | Initial Dry Wt (mg) | Dry Wt after 24 hr saline soak (mg) | Weight Change after saline soak (%) |
|---|---|---|---|---|
| High-G Alginate Samples | 1 | 76.4 | 80.3 | 5.10% |
| | 2 | 86.6 | 93.4 | 7.85% |
| | 3 | 92.1 | 96.5 | 4.78% |
| | 4 | 87.2 | 89.7 | 2.87% |
| | 5 | 89.3 | 94.6 | 5.94% |
| | 6 | 95.4 | 99.5 | 4.30% |
| | | | Average | 5.14% |
| Low-G Alginate Samples | 7 | 85.4 | 80.4 | −5.85% |
| | 8 | 80.1 | 75.1 | −6.24% |
| | 9 | 79.6 | 74.4 | −6.53% |
| | 10 | 80.2 | 76.3 | −4.86% |
| | 11 | 81.5 | 76.9 | −5.64% |
| | 12 | 71.5 | 68.2 | −4.62% |
| | | | Average | −5.63% |

It should be noted that the salt from the saline added some weight to each sample such that the high-G samples show a net weight gain. Thus, the low-G samples in which the weight change was only about −5% may have lost as much as 10% of their original dry weight if the amount of salt absorbed is assumed to be the same between the high-G and low-G samples. The results of this experiment illustrate that according to some embodiments of the present disclosure, use of a high-G alginate in a hemostatic device can be determined in a post-manufacturing setting by comparing the dry weight change from before and after a saline soak. Generally, the weight change of hemostatic devices utilizing a high-G alginate may result in a net weight gain as compared to the net weight loss of hemostatic devices utilizing a low-G alginate. In some embodiments, the average weight of a hemostatic device after exposure to saline and subsequent drying can be greater than the average weight of the hemostatic device before exposure to fluids such as saline or blood. In some embodiments, the average amount of hemostatic agent separated from the hemostatic device during exposure to blood or saline is less than or equal to about 50%, less than or equal to about 10%, or less than or equal to about 5%. These data illustrate that, in some embodiments, a device utilizing a high-G alginate experiences a net weight gain when subjected to the above test and a low-G alginate experiences a net weight loss using the same test. Thus, in some situations, a sample of an alginate of unknown guluronate concentration or proportion that experiences a net weight gain or no appreciable weight loss in accordance with the steps of this test may be likely to be a high-G alginate. Conversely, an unknown alginate used in a previously-untested sample that experiences a net weight loss may be likely to be a low-G alginate. Thus, it is not always necessary to know or determine the guluronate composition by way of a composition test in order to determine whether it is either a high-G alginate or a low-G alginate.

Example 5—Elemental Analysis of a Hemostatic Device Having a Crosslinked Binder

Three samples of a hemostatic device manufactured according to some embodiments of the present disclosure were subjected to an elemental analysis. A cross-linked binder such as an alginate was used to produce two of the three test samples with the third sample having no alginate so as to act as a control. Even though a different alginate was used in each sample, each alginate was a high-G alginate. In this experiment, the respective quantities of calcium and sodium were determined for each sample.

| Sample Number | Description |
|---|---|
| 1 | Uncoated dressing (control) |
| 2 | Dressing coated with Alginate B |
| 3 | Dressing coated with Alginate A |

Approximately seven square inches of each sample were sectioned from each sample for testing. The calcium and sodium were determined according to EPA 6010B. The instrumentation used was a Teledyne-Leeman Labs Profile ICP-OES (inductively coupled plasma optical emission spectrometer). A piece of each sample was sectioned to approximately seven square inches to a total mass of ~0.5 grams. Each massed sample was mixed with nitric acid to a 1:1 ratio (by mass). The mixture was heated in a boiling water bath for 2 hours. Two milliliters of HCL were added, and the volume increased to 50 milliliters with DI water. The results for the element analysis are shown in the following table.

| Element | Units | Sample 1 Results | Sample 1 Lower limit of detection | Sample 2 Results | Sample 2 Lower limit of detection | Sample 3 Results | Sample 3 Lower limit of detection |
|---|---|---|---|---|---|---|---|
| Calcium | mg/kg | 89.6 | 1.5 | 5000.0 | 23.3 | 4130.0 | 20.4 |
| Sodium | mg/kg | 245.0 | 0.6 | 112.0 | 0.7 | 99.4 | 0.8 |

The amount of calcium relative to the sodium contained in each sample indicates the extent of crosslinking within the alginate contained in each sample. The data for Sample 1—the control—indicates that even an uncoated or untreated piece of gauze can contain at least some calcium and sodium in some embodiments. However, once coated or treated with an alginate binder, some embodiments such as Samples 2 and 3 above contain much more calcium than sodium. Without being bound to any particular theory, it is believed that the crosslinking reaction between calcium and alginate previously described proceeds to a greater extent if a high-G alginate is used resulting in a greater quantity of calcium ions displacing sodium ions. The data from Samples 2 and 3 appear to support this theory.

Example 6—One Form of Measuring Degree of Retention of Hemostatic Agent from Substrate Using a Crosslinked Binder Various samples of hemostatic gauzes with a hemostatic material (e.g., kaolin), and a binder (e.g., a crosslinked binder such as calcium alginate), were produced using some of the methods described herein. As in some embodiments of the present disclosure, the alginate used in this experiment is a low-G alginate. The concentrations of the various components and the dry times were independently varied to produce each sample shown below. The samples were then subjected to a visual turbidity test and a clot time test. The table below contains the data gathered from these tests. As in some embodiments of the present disclosure, the alginate used in this experiment is a low-G alginate. Thus, the table below illustrates at least some of the benefits of using an alginate having a lower G content; however, other benefits may also be achieved by using a low-G alginate, benefits not readily apparent from the results of this experiment.

| 1. Sample | 2. Na Alg. (SA) % | 3. Kaolin:SA Ratio in Slurry (x:1) | 4. CaCl2 % | 5. Cross-link Time (minutes) | 6. Turbidity (Y or N) | 8. Clot Time (seconds) |
|---|---|---|---|---|---|---|
| Group 1 ||||||| 
| 312 F-2 | .5 | 5 | 5 | 2 | N | 126 |
| 312 F-5 | .5 | 5 | 5 | 5 | N | 129 |
| 712 V | .5 | 3 | 5 | 5 | N | 135 |
| 712 W | .5 | 5 | 5 | 5 | N | 117 |
| 712 X | .25 | 3 | 5 | 5 | N | 138 |
| 712 Y | .25 | 5 | 5 | 5 | N | 125 |
| 712 Z | .25 | 8 | 5 | 5 | N | 135 |
| 912 P | .5 | 5 | 3 | 5 | N | 116 |
| 912 N | .5 | 5 | 5 | 5 | N | 132 |
| 912 Q | .5 | 5 | 8 | 2 | N | 135 |
| 912 R | .5 | 5 | 8 | 5 | N | 129 |
| 912 T | .5 | 5 | 10 | 5 | N | 135 |
| 912 U | 1 | 1 | 5 | 5 | N | 128 |
| 912 V | 1 | 3 | 5 | 5 | N | 132 |
| Group 2 |||||||
| 012 F | .25 | 20 | 5 | 2 | Y | 117 |
| 012 H | .25 | 20 | 5 | 2 | Y | 106 |
| 312 B-2 | .25 | 10 | 5 | 2 | Y | 117 |
| 312 B-5 | .25 | 10 | 5 | 5 | Y | 129 |
| 312 C-2 | .25 | 20 | 5 | 2 | Y | 129 |
| 312 C-5 | .25 | 20 | 5 | 5 | Y | 132 |
| 312 D-5 | .25 | 30 | 5 | 5 | Y | 135 |
| 312 G-2 | .5 | 10 | 5 | 2 | Y | 129 |
| 312 G-5 | .5 | 10 | 5 | 5 | Y | 132 |
| 312 H-2 | .5 | 15 | 5 | 2 | Y | 135 |
| 312 H-5 | .5 | 15 | 5 | 5 | Y | 132 |
| 912 K | .5 | 5 | 1 | 2 | Y | 132 |
| 912 L | .5 | 5 | 1 | 5 | Y | 132 |
| 912 O | .5 | 5 | 3 | 2 | Y | 132 |
| 912 M | .5 | 5 | 5 | 2 | Y | 138 |
| 912 S | .5 | 5 | 10 | 2 | Y | 129 |
| 912 W | 1 | 5 | 5 | 5 | Y | 126 |
| Group 3 |||||||
| 312 A-2 | .25 | 0 | 5 | 2 | N | 219 |
| 312 A-5 | .25 | 0 | 5 | 5 | N | 249 |
| 312 E-2 | .5 | 0 | 5 | 2 | N | 207 |
| 312 E-5 | .5 | 0 | 5 | 5 | N | 210 |
| 712 U | .5 | 1 | 5 | 5 | N | 150 |

The explanation of Columns 1-6 and 8 provided in Example 1 applies in this example as well. In this table, the data in Column 7 represents a visual detection of turbidity while the respective samples were immersed and agitated in water.

A shorter clot time can be very desirable in stopping bleeding. However, another goal of some embodiments is to substantially retain the hemostatic agent on the hemostatic device during manufacture, packaging, transport, and the eventual application to and removal from a bleeding wound. The turbidity test is a qualitative test in which a sample product is considered to have passed the test or to have achieved a "No" in the above table if, when submersed in water, there was a visible absence of particles as seen by the naked eye under natural lighting conditions, in other words, if the water remained clear. Thus, a turbidity test indicates how well the calcium alginate binder retains the hemostatic agent in or on the gauze substrate when subjected to a liquid environment; however, other tests, experiments, or analyses may also or alternatively be used to determine this or similar information about embodiments of hemostatic devices of the present disclosure or similar products.

The samples in the above table have been divided into three general groups. Group 1 includes those samples that exhibited a clot time less than 150 seconds, and also exhibited minimal or no turbidity when immersed in liquid.

In other words, these samples had a favorable effect on bleeding, and the binder material substantially retained the hemostatic material on or in the gauze substrate when the samples were immersed in water. Group 2 includes those samples that exhibited a clot time less than 150 seconds, but also exhibited some turbidity when immersed in liquid. In other words, despite having a favorable effect on a bleeding wound, the binder did not substantially retain the hemostatic agent, in this case kaolin, when immersed in water. Group 3 includes those samples whose clot time equaled or exceeded 150 seconds irrespective of whether the samples also retained the hemostatic agent on the gauze substrate.

Although some embodiments of the invention have been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the scope thereof. Therefore, it is intended that the invention not be limited to the particular embodiments disclosed in the above detailed description, but that the invention will include all embodiments falling within the scope of the appended claims.

The invention claimed is:

1. A hemostatic device comprising:
   a gauze substrate;
   a hemostatic clay material; and
   a water-insoluble, crosslinkable, biocompatible, polymeric binder configured to immobilize the hemostatic clay material on the substrate such that the hemostatic clay material does not visibly separate from the substrate in the presence of water;
   wherein the hemostatic device is not saturated before use;
   wherein the binder resists dissolving in blood;
   wherein the device is configured such that when treating bleeding, application of the device is capable of causing blood to be absorbed into the gauze substrate and causing at least a portion of the hemostatic clay material to come into direct contact with blood to assist in accelerating clotting, but the device resists releasing the hemostatic material into a bleeding wound.

2. The hemostatic device of claim 1, wherein the water-insoluble, crosslinkable, biocompatible, polymeric binder is a crosslinked binder.

3. The hemostatic device of claim 2, wherein the water-insoluble, biocompatible, polymeric crosslinked binder includes covalent crosslinks.

4. The hemostatic device of claim 2, wherein the water-insoluble, biocompatible, polymeric crosslinked binder includes ionic crosslinks.

5. The hemostatic device of claim 2, wherein the water-insoluble, biocompatible, polymeric crosslinked binder includes ionic and covalent crosslinks.

6. The hemostatic device of claim 1, wherein there is virtually no cross-linking between the hemostatic clay material and the binder.

7. The hemostatic device of claim 1, wherein the hemostatic device is flexible to allow the hemostatic device to form to a shape of the bleeding wound and to retain a shape of the bleeding wound.

8. The hemostatic device of claim 1, wherein the binder is applied to the gauze substrate by a spraying process.

9. The hemostatic device of claim 1, wherein the binder is applied to the gauze substrate by immersing the gauze substrate in a liquid comprising the binder.

10. The hemostatic device of claim 1, wherein the binder is applied to the gauze substrate using a roller.

11. The hemostatic device of claim 1, the binder is applied to the gauze substrate using a slot die.

12. A hemostatic device comprising:
    a substrate;
    a hemostatic clay material disposed on at least one side of the substrate; and
    a water-insoluble, crosslinkable, biocompatible, polymeric binder configured to entrap the hemostatic clay material on the substrate such that the hemostatic clay material does not visibly separate from the substrate in the presence of water;
    wherein the hemostatic device is subjected to a drying process;
    wherein the binder has an effect of substantially retaining the hemostatic clay material on the substrate when exposed to blood;
    wherein the device is configured such that when treating bleeding, application of the device is capable of causing blood to be absorbed into the substrate and causing at least a portion of the hemostatic clay material to come into direct contact with blood to assist in accelerating clotting.

13. The hemostatic device of claim 12, wherein the substrate comprises at least one of the following: a gauze material, a woven material, a sponge, a sponge matrix, woven fabric, non-woven fabric, or a foamed polymer.

14. The hemostatic device of claim 12, wherein the substrate comprises a material selected from the group consisting of cotton, silk, wool, plastic, cellulose, rayon, polyester, polyurethane, polyethylene foam, PHEMA foam, polyacrylic acid foam, low-density polyether, polyvinyl alcohol, polyhydroxybutyrate methyl methacrylate, poly methylmethacrylate, or combinations of the foregoing.

15. The hemostatic device of claim 12, wherein the water water-insoluble, crosslinkable, biocompatible, polymeric binder comprises crosslinks.

16. The hemostatic device of claim 15, wherein the crosslinks include covalent crosslinks.

17. The hemostatic device of claim 15, wherein the crosslinks include ionic crosslinks.

18. The hemostatic device of claim 15, wherein the crosslinks include ionic and covalent crosslinks.

19. The hemostatic device of claim 12, wherein the hemostatic device is flexible to allow the hemostatic device to form to a shape of the bleeding wound and to retain a shape of the bleeding wound.

* * * * *